United States Patent
Kim et al.

(10) Patent No.: US 10,851,177 B2
(45) Date of Patent: Dec. 1, 2020

(54) METHOD FOR INHIBITING INTRACELLULAR ACTIVATED RAS USING INTACT IMMUNOGLOBULIN-TYPE ANTIBODY HAVING CYTOSOL-PENETRATING ABILITY AND USE THEREOF

(71) Applicant: ORUM THERAPEUTICS INC., Daejeon (KR)

(72) Inventors: Yong-Sung Kim, Gyeonggi-do (KR); Dong-Ki Choi, Gyeonggi-do (KR); Seung-Min Shin, Seoul (KR); Sung-Hoon Kim, Seoul (KR)

(73) Assignee: ORUM THERAPEUTICS INC., Daejeon (KR)

( * ) Notice: Subject to any disclaimer, the term of this patent is extended or adjusted under 35 U.S.C. 154(b) by 140 days.

(21) Appl. No.: 15/327,539

(22) PCT Filed: Jul. 22, 2015

(86) PCT No.: PCT/KR2015/007627
§ 371 (c)(1),
(2) Date: Jan. 19, 2017

(87) PCT Pub. No.: WO2016/013871
PCT Pub. Date: Jan. 28, 2016

(65) Prior Publication Data
US 2017/0158777 A1 Jun. 8, 2017

(30) Foreign Application Priority Data

Jul. 22, 2014 (KR) .................. 10-2014-0092687
Jul. 21, 2015 (KR) .................. 10-2015-0103214

(51) Int. Cl.
| | | |
|---|---|---|
| C07K 16/32 | (2006.01) | |
| C07K 16/40 | (2006.01) | |
| C07K 16/42 | (2006.01) | |
| A61K 39/00 | (2006.01) | |
| C07K 17/08 | (2006.01) | |
| G01N 33/566 | (2006.01) | |
| C07K 16/44 | (2006.01) | |
| G01N 33/574 | (2006.01) | |
| C07K 7/06 | (2006.01) | |
| G01N 33/68 | (2006.01) | |

(52) U.S. Cl.
CPC .............. *C07K 16/40* (2013.01); *C07K 7/06* (2013.01); *C07K 16/32* (2013.01); *C07K 16/44* (2013.01); *C12Y 306/05002* (2013.01); *G01N 33/566* (2013.01); *G01N 33/5748* (2013.01); *G01N 33/6854* (2013.01); *A61K 2039/505* (2013.01); *C07K 2317/21* (2013.01); *C07K 2317/24* (2013.01); *C07K 2317/30* (2013.01); *C07K 2317/56* (2013.01); *C07K 2317/565* (2013.01); *C07K 2317/569* (2013.01); *C07K 2317/73* (2013.01); *C07K 2317/76* (2013.01); *C07K 2317/77* (2013.01); *C07K 2317/92* (2013.01); *C07K 2319/00* (2013.01); *G01N 2333/914* (2013.01); *G01N 2500/04* (2013.01)

(58) Field of Classification Search
None
See application file for complete search history.

(56) References Cited

U.S. PATENT DOCUMENTS

| | | |
|---|---|---|
| 9,815,866 B2 | 11/2017 | Shiba et al. |
| 2005/0288492 A1 | 12/2005 | Rabbitts et al. |
| 2011/0189206 A1 | 8/2011 | Barbas |
| 2011/0263829 A1 | 10/2011 | Kim et al. |
| 2013/0266570 A1 | 10/2013 | Weisbart et al. |
| 2014/0179543 A1 | 6/2014 | Rabbitts et al. |
| 2015/0246945 A1 | 9/2015 | Shiba et al. |
| 2016/0229892 A1 | 8/2016 | Hazlehurst et al. |
| 2017/0218084 A1 | 8/2017 | Kim et al. |
| 2019/0144566 A1 | 5/2019 | Kim et al. |
| 2019/0231872 A1 | 8/2019 | Kwon et al. |
| 2019/0389910 A1 | 12/2019 | Kim et al. |

FOREIGN PATENT DOCUMENTS

| | | |
|---|---|---|
| CN | 1241574 A | 1/2000 |
| CN | 101402675 A | 4/2009 |
| CN | 102209726 A | 10/2011 |
| CN | 103874710 A | 6/2014 |
| JP | H 8-511162 A | 11/1996 |
| JP | 2006521088 A | 9/2006 |
| JP | 2006523086 A | 10/2006 |
| JP | 2011519370 A | 7/2011 |
| KR | 1020090008290 A | 1/2009 |
| KR | 10-2010-0045683 | 5/2010 |
| KR | 10-2010-0053466 A | 5/2010 |
| KR | 10-2016-0011598 A | 2/2016 |
| KR | 10-1790669 B1 | 10/2017 |
| KR | 10-2019-0056340 A | 5/2019 |
| WO | 03077945 A1 | 9/2003 |
| WO | WO 2004046186 A2 | 6/2004 |

(Continued)

OTHER PUBLICATIONS

Sapra et al. (Cancer Res. Dec. 15, 2002; 62 (24): 7190-4). (Year: 2002).*

(Continued)

*Primary Examiner* — Gary B Nickol
*Assistant Examiner* — Jegatheesan Seharaseyon
(74) *Attorney, Agent, or Firm* — Jones Day

(57) ABSTRACT

The present disclosure relates to a method for inhibiting intracellular activated (GTP-bound) RAS using an intact immunoglobulin-type antibody having the ability to penetrate the cytosol, and to the use thereof. The disclosure further relates to a heavy-chain variable region (VH) which induces an intact immunoglobulin-type antibody to penetrate the cytosol and bind to activated RAS in the cytosol, and to an antibody comprising the same. The disclosure correspondingly provides a method for inhibiting the growth of cancer or tumor cells using the antibody, and a method for treating cancer or tumor.

14 Claims, 29 Drawing Sheets
(23 of 29 Drawing Sheet(s) Filed in Color)
Specification includes a Sequence Listing.

(56) References Cited

FOREIGN PATENT DOCUMENTS

| WO | WO 2004046186 A3 | 6/2004 |
|---|---|---|
| WO | WO 2004046188 A2 | 6/2004 |
| WO | WO 2004046188 A3 | 6/2004 |
| WO | WO 2007133835 A2 | 11/2007 |
| WO | WO 2007133835 A3 | 11/2007 |
| WO | 2009-134025 | 11/2009 |
| WO | 2009134027 A2 | 11/2009 |
| WO | 2010-056043 | 5/2010 |
| WO | WO 2011026641 A1 | 3/2011 |
| WO | WO 2011026641 A9 | 3/2011 |
| WO | WO 2011140151 A1 | 11/2011 |
| WO | WO 2012135831 A1 | 10/2012 |
| WO | WO 2014042209 A1 | 3/2014 |
| WO | WO 2016013870 A1 | 1/2016 |
| WO | WO 2016161390 A1 | 10/2016 |
| WO | WO 2017204606 A1 | 11/2017 |

OTHER PUBLICATIONS

Yamaguchi et al. (Biochem. Biophys. Res. Commun. Nov. 1, 2014; 454 (4): 600-603). (Year: 2014).*
Stuible et al. (J. Biol. Chem. Mar. 7, 2014; 289 (10): 6498-512) (Year: 2014).*
Rudikoff et al. (Proc. Natl. Acad. Sci. USA. 1982; 79: 1979-1983) (Year: 1982).*
Mariuzza et al. (Annu. Rev. Biophys. Biophys. Chem. 1987; 16: 139-159) (Year: 1987).*
Gussow et al. (Methods in Enzymology. 1991; 203: 99-121) (Year: 1991).*
Giusti et al. (Proc. Natl. Acad. Sci. USA. May 1987; 84 (9): 2926-2930) (Year: 1987).*
Chien et al. (Proc. Natl. Acad. Sci. USA. Jul. 1989; 86 (14): 5532-5536) (Year: 1989).*
Caldas et al. (Mol. Immunol. May 2003; 39 (15): 941-952) (Year: 2003).*
Winkler et al. (J. Immunol. Oct. 15, 2000; 165 (8): 4505-4514) (Year: 2000).*
Vajdos et al. (J. Mol. Biol. Jul. 5, 2002; 320 (2): 415-428) (Year: 2002).*
De Pascalis et al. (J. Immunol. 2002; 169 (6): 3076-3084) (Year: 2002).*
Wu et al. (J. Mol. Biol. Nov. 19, 1999; 294 (1): 151-162) (Year: 1999).*
Casset et al. (Biochem. Biophys. Res. Commun. Jul. 18, 2003; 307 (1): 198-205). (Year: 2003).*
MacCallum et al. (J. Mol. Biol. Oct. 11, 1996; 262 (5): 732-745) (Year: 1996).*
XHolm et al. (Mol. Immunol. Feb. 2007; 44 (6): 1075-1084) (Year: 2007).*
Yu et al. (PLoS One. 2012; 7 (3): e33340; pp. 1-15) (Year: 2012).*
Chang et al. (Structure. Jan. 7, 2014; 22 (1): 9-21) (Year: 2014).*
Choi et al. (MAbs. 2014; 6 (6): 1402-14) (Year: 2014).*
Rudikoff et al., Proc Natl Acad Sci USA 79: 1979-1983 (Year: 1982).*
Colman, Research in Immunology 145: 33-36. (Year: 1994).*
Kussie et al., J. Immunol. 152: 146-152 (Year: 1994).*
Chen et al., EMBO J., 14: 2784-2794 (Year: 1995).*
T. Tanaka et al., "Single Domain Intracellular Antibodies: A minimal Fragment for Direct in Vivo Selection of Antigen-specific Intrabodies", Journal of Molecular Biology (JMB), Academic press, United Kingdom, vol. 331, No. 5, Aug. 29, 2003, pp. 1109-1120.
Y. Kim, "A General Strategy for Generating Intact, Full-length IgG Antibodies that Penetrate into The Cytosol of Living Cells", KSBB, IP306, Oct. 5, 2014, XP002776743.
S. Shin et al., "Antibody targeting intracellular oncogenic Ras mutants excerts anti-tumour effects after systemic administration", Nature Communications, May 10, 2017, vol. 8, pp. 1-14.
EPO, The extended European Search Report of EP15825508.3 dated Feb. 8, 2018.

Baek, D.S., et al., "Construction of a Large Synthetic Human Fab Antibody Library on Yeast Cell Surface by Optimized Yeast Mating", "Journal of Microbiology and Biotechnology", Jan. 7, 2014, pp. 408-420, vol. 24, No. 3.
Benatuil, L., et al., "An Improved Yeast Transformation Method for the Generation of Very Large Human Antibody Libraries", "Protein Engineering, Design & Selection", Jan. 4, 2010, pp. 155-159, vol. 23, No. 4.
Blundell, T.L., et al., "Structural Biology and Bioinformatics in Drug Design: Opportunities and Challenges for Target Identification and Lead Discovery", "Philosophical Transactions of the Royal Society B", Feb. 3, 2006, pp. 413-423, vol. 361.
Cao, L., et al., "Enhancement of Antitumor Properties of TRAIL by Targeted Delivery to the Tumor Neovasculature", "Molecular Cancer Therapeutics", Apr. 2008, pp. 851-861, vol. 7, No. 4.
Chauhan, A., et al., "The Taming of the Cell Penetrating Domain of the HIV Tat: Myths and Realities", "Journal of Controlled Release", Nov. 17, 2006, pp. 148-162, vol. 117.
Ehrenstein, M.R., et al., "Human IgG Anti-DNA Antibodies Deposit in Kidneys and Induce Proteinuria in SCID Mice", "Kidney International", May 1, 1995, pp. 705-711, vol. 48.
Falnes, P.O., et al., "Ability of the Tat Basic Domain and VP22 to Mediate Cell Binding, but Not Membrane Translocation of the Diphtheria Toxin A-Fragment", "Biochemistry", Jan. 3, 2001, pp. 4349-4358, vol. 40.
Gerber, H.P., et al., "The Antibody-Drug Conjugate: an Enabling Modality for Natural Product-Based Cancer Therapeutics", "The Royal Society of Chemistry 2013", Mar. 25, 2013, pp. DOI: 10.1039/c3np20113a, Publisher: RSC Publishing.
Horth, M., et al., "Theoretical and Functional Analysis of the SIV Fusion Peptide", "The EMBO Journal", May 27, 1991, pp. 2747-2755, vol. 10, No. 10.
Imai, K., et al., "Comparing Antibody and Small-Molecule Therapies for Cancer", "Nature Reviews", Sep. 2006, pp. 714-727, vol. 6.
Jenssen, H., et al, "Peptide Antimicrobial Agents", "Clinical Microbiology Reviews", Jul. 2006, pp. 491-511, vol. 19, No. 3.
Kabat, E.A., et al., "Sequences of Proteins of Immunological Interest", 1991, pp. 1-24, vol. 1.
Kim, S.J., et al., "Antibody Engineering for the Development of Therapeutic Antibodies", "Molecules and Cells", Aug. 18, 2005, pp. 17-29, vol. 20, No. 1.
Koivunen, E., et al., "Phage Libraries Displaying Cyclic Peptides with Different Ring Sizes: Ligand Specificities of the RGD-Directed Integrins", "Nature Biotechnology", Mar. 1995, pp. 265-270, vol. 13.
Lee, J., et al., "Functional Consequences of Complementarity-determining Region Deactivation in a Multifunctional Anti-nucleic Acid Antibody", "The Journal of Biological Chemistry", Dec. 13, 2013, pp. 35877-35885, vol. 288, No. 50.
Lin, C., et al., "Effect of Chemical Functionalities in Poly(Amido Amine)s for Non-viral Gene Transfection", "Journal of Controlled Release", Jul. 3, 2008, pp. 267-272, vol. 132.
Madaio, M.P., et al., "Spontaneously Produced Anti-DNA/DNase I Autoantibodies Modulate Nuclear Apoptosis in Living Cells", "European Journal of Immunology", Sep. 24, 2006, pp. 3035-3041, vol. 26.
Manikandan, J., et al., "Protein i: Interference at Protein Level by Intrabodies", "Fronteirs in Bioscience", Jan. 1, 2007, pp. 1344-1352, vol. 12.
Marschall, A.L.J., "Targeting Antibodies to the Cytoplasm", "mAbs", Jan. 2011, pp. DOI: 10.4161/mabs.3.1.14110, Publisher: Landes Bioscience.
Nakajima, O., et al., "Method for Delivering Radiolabeled Single-Chain Fv Antibody to the Brain", "Journal of Health Science", Jan. 5, 2004, pp. 159-163, vol. 50, No. 2.
Patel, L.N., et al., "Cell Penetrating Peptides: Intracellular Pathways and Pharmaceutical Perspectives", "Pharmaceutical Research", Apr. 19, 2007, pp. 1977-1992, vol. 24, No. 11.
Scheffzek, K., et al., "The Ras-RasGAP Complex: Structural Basis for GTPase Activation and Its Loss in Oncogenic Ras Mutants", "Science Magazine", Jul. 18, 1997, pp. 333-338, vol. 277.

(56) References Cited

OTHER PUBLICATIONS

Tanaka, T., et al., "Tumour Prevention by a Single Antibody Domain Targeting the Interaction of Signal Transduction Proteins with RAS", "The EMBO Journal", Jun. 14, 2007, pp. 3250-3259, vol. 26.
Tanaka, T., et al., "Intrabodies Based on Intracellular Capture Frameworks that Bind the RAS Protein with High Affinity and Impair Oncogenic Transformation", "The EMBO Journal", Jan. 10, 2003, pp. 1025-1035, vol. 22, No. 5.
Vargas-Madrazo, E., et al., "An Improved Model of Association for VH-VL Immunoglobulin Domains: Asymmetries Between VH and VL in the Packing of Some Interface Residues", "Journal of Molecular Recognition", Jan. 10, 2003, pp. 113-120, vol. 16.
Weisbart, R.H., et al., "A Cell-Penetrating Bispecific Antibody for Therapeutic Regulation of Intracellular Targets", "Molecular Cancer Therapeutics", Oct. 2012, pp. 2169-2173, vol. 11, No. 10.
Zack, D.J., et al., "Mechanisms of Cellular Penetration and Nuclear Localization of an Anti-Double Strand DNA Autoantibody", "The Journal of Immunology", Jun. 18, 1996, pp. 2082-2088, vol. 157.
Madaio, M.P., et al., "Spontaneously Produced Anti-DNA/DNase I Autoantibodies Modulate Nuclear Apoptosis in Living Cells", "European Journal of Immunology", 1996, pp. 3035-3041, vol. 26.
Al-Lazikani et al., 1997, "Standard conformations for the canonical structures of immunoglobulins," J Mol Biol, 273(4):927-948.
Altmann et al., 2017, "Identification of a Novel ITGαvβ6-Binding Peptide Using Protein Separation and Phage Display," Clin Cancer Res., 23(15):4170-4180.
Avrameas et al., 1998, "Polyreactive anti-DNA monoclonal antibodies and a derived peptide as vectors for the intracytoplasmic and intranuclear translocation of macromolecules," Proc Natl Acad Sci USA, 95(10):5601-5606.
Baek et al. 2014, "DNA Assembly Tools and Strategies for the Generation of Plasmids," Microbiol Spectr, 2(5), pp. 1-12.
Baek et al., 2015, "Humanization of a phosphothreonine peptide-specific chicken antibody by combinatorial library optimization of the phosphoepitope-binding motif," Biochem Biophys Res. Commun., 463(3):414-420.
Barbas et al., 2007, "Quantitation of DNA and RNA," Cold Spring Harb. Protoc., retreived from internet: http://cshprotocols.cshlp.org/content/2007/11/pdb.ip47.long on Nov. 1, 2019 (2 pages).
Barrette-Ng et al., 2013, "The structure of the SBP-Tag-streptavidin complex reveals a novel helical scaffold bridging binding pockets on separate subunits," Acta Crystallogr D Biol Crystallogr., 69(Pt 5):879-887.
Bissig et al., 2013, "Lipid sorting and multivesicular endosome biogenesis," Cold Spring Harb Perspect Biol., 5(10):a016816.
Bonvin et al., 2015, "De novo isolation of antibodies with pH-dependent binding properties," Mabs, 7(2):294-302.
Cabantous et al., 2005, "Protein tagging and detection with engineered self-assembling fragments of green fluorescent protein," Nat Biotechnol., 23(1):102-107.
Cross et al., 2001, "Mechanisms of Cell Entry by Influenza Virus," Expert Review in Molecular Medicine, Aug. 2001, pp. 1-18.
Devanaboyina et al., 2013, "The effect of pH dependence of antibody-antigen interactions on subcellular trafficking dynamics," Mabs, 5(6):851-859.
Di Paolo et al., 2003, "A recombinant immunotoxin derived from a humanized epithelial cell adhesion molecule-specific single-chain antibody fragment has potent and selective antitumor activity," Clin Cancer Res, 9(7):2837-2848.
Di Russo et al., 2012, "pH-Dependent conformational changes in proteins and their effect on experimental pK(a)s: the case of Nitrophorin 4," PLoS Comput Biol., 8(11):e1002761.
Dohi et al., 2001, "Elimination of colonic patches with lymphotoxin receptor-Ig prevents Th2 cell-type colitis," The Journal of Immunology, 167(5):2781-2790.
Du et al., 2011, "pK(a) coupling at the intein active site: implications for the coordination mechanism of protein splicing with a conserved aspartate," J Am Chem Soc., 133(26):10275-10282.
Dudgeon et al., 2012, "General strategy for the generation of human antibody variable domains with increased aggregation resistance," Proc Natl Acad Sci USA, 109(27):10879-10884.
Edman, 1959, "Chemistry of amino acids and peptides," Annu Rev Biochem, 28:69-96.
Ewert et al., 2004, "Stability improvement of antibodies for extracellular and intracellular applications: CDR grafting to stable frameworks and structure-based framework engineering," Methods, 34(2):184-199.
Extended European Search Report and Written Opinion of European Patent Application No. 15825418.5 dated Jan. 4, 2018 (8 pages).
Fernandes et al., 2016, "Context-dependent roles for lymphotoxin-β receptor signaling in cancer development," Biochim Biophys Acta., 1865(2):204-219.
Garrigues et al., 1993, "Ley specific antibody with potent anti-tumor activity is internalized and degraded in lysosomes," Am J Pathol., 142(2):607-622.
Gingis-Velitski et al., 2004, "Heparanase uptake is mediated by cell membrane heparan sulfate proteoglycans," J Biol Chem., 279(42):44084-44092.
Gouttefangeas et al., 2014, "Flow Cytometry in Cancer Immunotherapy: Applications, Quality Assurance, and Future," N. Rezaei (ed.), Cancer Immunology: A Translational Medicine Context, Springer-Verlag Berlin Heidelberg, Chapter 25, pp. 471-490.
Guglielmi et al., 2011, "Selection for intrabody solubility in mammalian cells using GFP fusions," Protein Eng Des Sel., 24(12):873-881.
Guidotti et al., 2017, "Cell-Penetrating Peptides: From Basic Research to Clinics," Trends in Pharmacological Sciences, 38(4):406-424.
Guillard et al., 2015, "Engineering therapeutic proteins for cell entry: the natural approach," Trends in biotechnology, 33(3):163-171.
Herce et al., 2009, "Arginine-rich peptides destabilize the plasma membrane, consistent with a pore formation translocation mechanism of cell-penetrating peptides," Biophys J., 97(7):1917-1925.
Holig et al., 2004, "Novel RGD lipopeptides for the targeting of liposomes to integrin-expressing endothelial and melanoma cells," Prot Eng Des Sel, 17(5):433-441.
Hollingshead, 2008, "Antitumor efficacy testing in rodents," J Natl Cancer Inst., 100(21):1500-1510.
Horton et al., 2002, "Exploring privileged structures: the combinatorial synthesis of cyclic peptides," J Comput Aided Mol Des., 16(5-6):415-430.
Hu et al., 2013, "Comparison of the inhibition mechanisms of adalimumab and infliximab in treating tumor necrosis factor α-associated diseases from a molecular view," J Biol Chem., 288(38):27059-27067.
International Search Report and Written Opinion dated Oct. 11, 2019 for International Patent Application No. PCT/IB2019/055193 (14 pages).
International Search Report and Written Opinion dated Oct. 7, 2015 for International Patent Application No. PCT/KR2015/007626 (published as WO 2016013870) (12 pages).
International Search Report and Written Opinion dated Sep. 29, 2017 for International Patent Application No. PCT/KR2017/005559 (published as WO 2017204606) (10 pages).
International Search Report and Written Opinion dated Sep. 30, 2015 for International Patent Application No. PCT/KR2015/007627 (published as WO 2016013871) (12 pages).
Jang et al., 2009, "A nucleic acid-hydrolyzing antibody penetrates into cells via caveolae-mediated endocytosis, localizes in the cytosol and exhibits cytotoxicity," Cell Mol Life Sci., 66(11-12):1985-1997.
Kamide et al., 2010, "Isolation of novel cell-penetrating peptides from a random peptide library using in vitro virus and their modifications," Int J Mol Med., 25(1):41-51.
Kim et al., 2006, "Heavy and light chain variable single domains of an anti-DNA binding antibody hydrolyze both double- and single-stranded DNAs without sequence specificity," J Biol Chem., 281(22):15287-15295.

(56) References Cited

OTHER PUBLICATIONS

Kim et al., 2012, "Interfering transbody-mediated Her2 gene silencing induces apoptosis by G0/G1 cell cycle arrest in Her2-overexpressing SK-BR-3 breast cancer cells," Biotechnology and Bioprocess Engineering, 17(2):413-419.
Kim et al., 2015, "Quantitative assessment of cellular uptake and cytosolic access of antibody in living cells by an enhanced split GFP complementation assay," Biochem Biophys Res Commun., 467(4):771-777.
Kim et al., 2016, "Endosomal acidic pH-induced conformational changes of a cytosol-penetrating antibody mediate endosomal escape," J Control Release, 235:165-175.
Korte et al., 1992, "ph-dependent hydrophobicity profile of hemagglutinin of influenza virus and its possible relevance in virus fusion," Biosci Rep., 12(5):397-406.
Lee et al., 2010, "Gene silencing by cell-penetrating, sequence-selective and nucleic-acid hydrolyzing antibodies," Nucleic Acids Res., 38(5):1596-1609.
Lee et al., 2011, "Generation of bivalent and bispecific kringle single domains by loop grafting as potent agonists against death receptors 4 and 5," J Mol Biol., 411(1):201-219.
Leem et al., 2016, "ABodyBuilder: Automated antibody structure prediction with data-driven accuracy estimation," MAbs, 8(7):1259-1268.
Leshchiner et al., 2015, "Direct inhibition of oncogenic KRAS by hydrocarbon-stapled SOS1 helices," Proc Natl Acad Sci USA, 112(6):1761-1766.
Li et al., 2014, "pH-Controlled two-step uncoating of influenza virus," Biophys J., 106(7):1447-1456.
Lonn et al., 2016, "Enhancing Endosomal Escape for Intracellular Delivery of Macromolecular Biologic Therapeutics," Sci Rep., 6:32301.
Madgdelaine-Beuzelin et al., 2007, "Structure-function relationships of the variable domains of monoclonal antibodies approved for cancer treatment," Crit Rev Oncol Hematol., 64(3):210-225.
Marchisio et al., 1984, "Immunofluorescence localization of phosphotyrosine containing proteins in RSV-transformed mouse fibroblasts," Exp Cell Res., 154(1):112-124.
Mauri et al., 1998, "LIGHT, a new member of the TNF superfamily, and lymphotoxin alpha are ligands," Immunity, 8(1):21-30.
Morita et al., 2011, "Lipid recognition propensities of amino acids in membrane proteins from atomic resolution data," BMC Biophys., 4:21 (12 pages).
Munyendo et al., 2012, "Cell penetrating peptides in the delivery of biopharmaceuticals," Biomolecules, 2(2):187-202.
Munz et al., 2009, "The emerging role of EpCAM in cancer and stem cell signaling," Cancer Res., 69(14):5627-5629.
NCBI, 2016, "Chain H, Heavy Chain of Fab Fragment Variable Region of Antibody D5," PDB: 3JAU_H, NCBI database, Feb. 10, 2016.
Patgiri et al., 2011, "An orthosteric inhibitor of the Ras-Sos interaction," Nat Chem Biol, 7(9):585-587.
Perchiacca et al., 2011, "Mutational analysis of domain antibodies reveals aggregation hotspots within and near the complementarity determining regions," Proteins, 79(9):2637-2647.

Perrimon et al., 2000, "Specificities of heparan sulphate proteoglycans in developmental processes," Nature, 404(6779):725-728.
Pimenta et al., 2014, "Role of tertiary lymphoid structures (TLS) in antitumor immunity: Potential tumor-induced cytokines/chemokines that regulate TLS formation in epithelial-derived cancers," Cancer, 6(2):969-997.
Qin et al., 1999, "Functional implications of structural differences between variants A and B of bovine beta-lactoglobulin," Protein Sci., 8(1):75-83.
Quadir et al., 2014, "PEG-polypeptide block copolymers as pH-responsive endosome-solubilizing drug nanocarriers," Mol Pharm., 11(7):2420-2430.
Rezai et al., 2006, "Testing the conformational hypothesis of passive membrane permeability using synthetic cyclic peptide diastereomers," J Am Chem Soc., 128(8):2510-2511.
Simon et al., 2013, "Epithelial cell adhesion molecule-targeted drug delivery for cancer therapy, Expert opinion on drug delivery," Expert Opin Drug Deliv., 10(4):451-468.
Singh et al., 2016, "A New Triglycyl Peptide Linker for Antibody-Drug Conjugates (ADCs) with Improved Targeted Killing of Cancer Cells," Mol Cancer Ther., 15(6):1311-1320.
Sudhamsu et al., 2013, "Dimerization of LTβR by LTα1β2 is necessary and sufficient for signal transduction," Proc Natl Acad Sci USA, 110(49):19896-19901.
Teicher, 2009, "In vivo/ex vivo and in situ assays used in cancer research: a brief review," Toxicol Pathol, 37(1):114-122.
Wang et al., 2001, "The regulation of T cell homeostasis and autoimmunity by T cell-derived LIGHT," J Clin Invest, 108(12):1771-1780.
Weinstein, 2015, "Lymphotoxin Therapeutic Lymphoid Organogenesis in the Tumor Microenvironment," Adv Cancer Res., 128:197-233.
Went et al., 2006, "Frequent high-level expression of the immunotherapeutic target Ep-CAM in colon, stomach, prostate and lung cancers," Br J Cancer, 94(1):128-135.
Xiong et al., 2002, "Crystal structure of the extracellular segment of integrin alpha Vbeta3 in complex with an Arg-Gly-Asp ligand," Science, 296(5565):151-155.
Min et al., 2016, "Cell-free production and streamlined assay of cytosol-penetrating antibodies," Biotechnol Bioeng, 113(10):2107-2112.
Williams et al., 2018, "Peptide ligands for targeting the extracellular domain of EGFR: Comparison between linear and cyclic peptides," Chem Biol Drug Des., 91(2):605-619.
Claro et al., 2017, "Chapter 4—Design and applications of cyclic peptides" in Peptide Applications in Biomedicine, Biotechnology and Bioengineering, Woodhead Publishing Series in Biomaterials, Nov. 27, 2017, pp. 87-129.
Kim et al., 2009, "Generation of Humanized anti-DNA Hydrolyzing Catalytic Antibodies by Complementarily Determining Region Grafting," Biochem Biophys Res Commun., 379(2):314-318 (Epub 2008).
Paul, 1993, "Fundamental immunology—Third Edition," New York: Raven Press, pp. 292-295.

* cited by examiner

Fig. 5A

```
                                      CDR1                              CDR2
                    10         20    abcdef   30           40           50
m3D8 VL(Vκ6)  DLVMSQSPSSLAVSAGEKVTMSC [KSSQSLFNSRTRKNYLA] WYQQKPGQSPKLLIY [WASTRES]
hT0 VL(Vκ3)   DIVLTQSPATLSLSPGERATLSC [KSSQSLFNSRTRKNYLA] WYQQKPGQAPRLLIY [WASTRES]
hT2 VL(Vκ3)   DLVMTQSPATLSLSPGERATLSC [KSSQSLFNSPTRKNYLA] WYQQKPGQAPRLLIY [WASTRES]
hT3 VL(Vκ1)   DLVMTQSPSSLSASVGDRVTITC [KSSQSLFNSPTRKNYLA] WYQQKPGKAPKLLIY [WASTRES]

CDR3
              60         70         80        90          100
m3D8 VL(Vκ6)  GVPDRFTGSGSGTDFTLTISSVQAEDLAVYYC [KQSYHMYT] FGSGTKLEIKR
hT0 VL(Vκ3)   GIPDRFSGSGSGTDFTLTISSLEPEDFAVYYC [KQSYHMYT] FGQGTKVEIKR
hT2 VL(Vκ3)   GIPDRFSGSGSGTDFTLTISSLEPEDFAVYYC [KQSYHMYT] FGQGTKVEIKR
hT3 VL(Vκ1)   GVPSRFSGSGSGTDFTLTISSLQPEDFATYYC [KQSYYHMYT] FGQGTKVEIKR
```

Fig. 5B

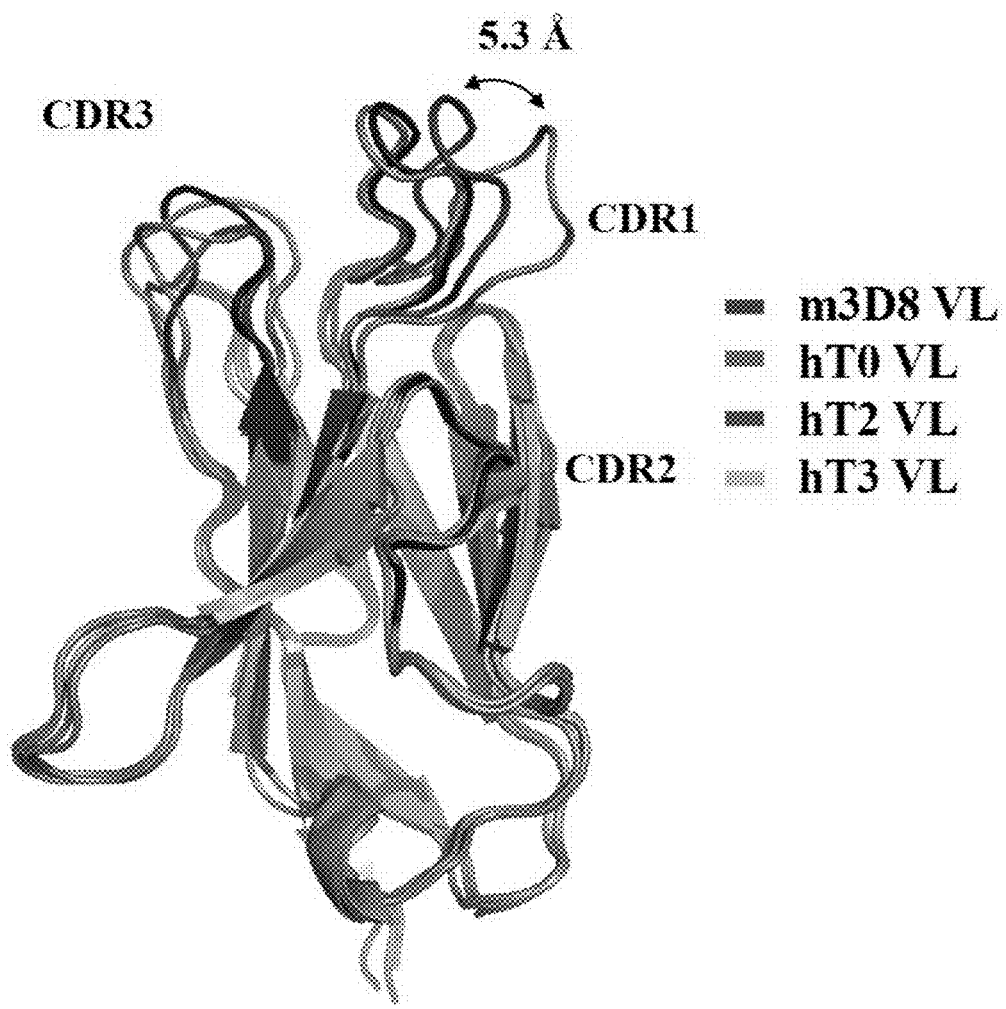

| KRas G12D·GTP | $k_a$ (M$^{-1}$S$^{-1}$) | $k_d$ (S$^{-1}$) | $K_D$ (M) |
|---|---|---|---|
| RT4 | $2.99 \times 10^4$ | $3.5 \times 10^{-3}$ | $1.1 \times 10^{-7}$ |

Image magnification, 630x; scale bar, 5 μm.

Image magnification, 630x; scale bar, 5 μm.

Image magnification, 630x; scale bar, 5 μm.

Fig. 22

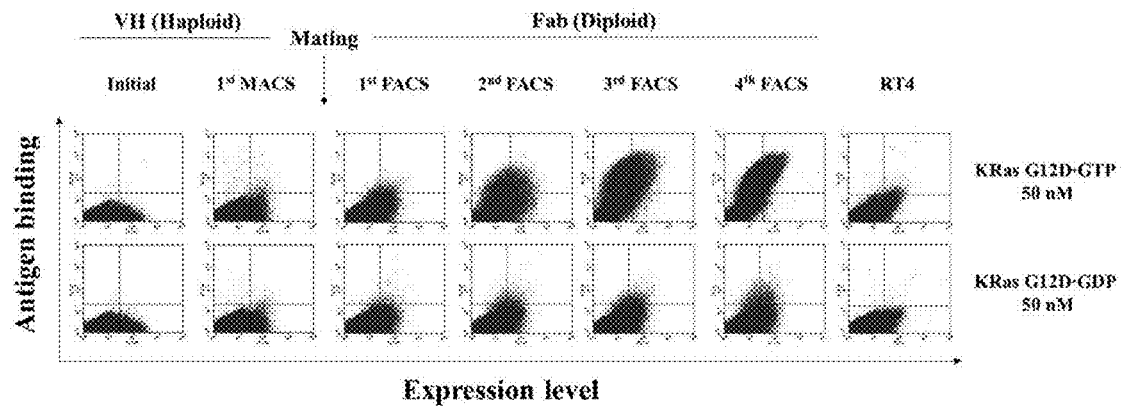

Fig. 23

| Kabat VH | | CDR1 | | CDR2 | |
|---|---|---|---|---|---|
| RT4 VH (library template) | EVQLVESGGGLVQPGGSLRLSCAASGFTFS | SYAMS | WVRQAPGKGLEWVSTISR | SGHSTYYADSVKGRF |
| RT11 VH | - - - - - - - - - - - - - - - - - - - - - - - - - - - - - - | SYSMS | - - - - - - - - - - - - - | YISR | TSHTTYYADSVKG - - |
| RT13 VH | - - - - - - - - - - - - - - - - - - - - - - - - - - - - - - | TFSMS | - - - - - - - - - - - - - | YISR | TSHTTYYADSVKG - - |
| RT14 VH | - - - - - - - - - - - - - - - - - - - - - - - - - - - - - - | TFSMS | - - - - - - - - - - - - - | YISR | TSHTTYYADSVKG - - |
| RT15 VH | - - - - - - - - - - - - - - - - - - - - - - - - - - - - - - | TFSMS | - - - - - - - - - - - - - | YISR | TSHTTYYADSVKG - - |
| RT16 VH | - - - - - - - - - - - - - - - - - - - - - - - - - - - - - - | TFSMS | - - - - - - - - - - - - - | YISR | TSHTTYYADSVKG - - |
| RT17 VH | - - - - - - - - - - - - - - - - - - - - - - - - - - - - - - | TFSMS | - - - - - - - - - - - - - | YISR | TSHTTYYADSVKG - - |

| Kabat VH | | CDR3 | |
|---|---|---|---|
| RT4 VH (library template) | TISRDNSKNTLYLQMNSLRAEDTAVYYCAK | RFGSIV | FDYWGQGTLVTVSS |
| RT11 VH | - - - - - - - - - - - - - - - - - - - - - - - - - - - - | GFF | MDY - - - - - - - - - |
| RT13 VH | - - - - - - - - - - - - - - - - - - - - - - - - - - - - | GTFG | FDY - - - - - - - - - |
| RT14 VH | - - - - - - - - - - - - - - - - - - - - - - - - - - - - | PRGW | FDY - - - - - - - - - |
| RT15 VH | - - - - - - - - - - - - - - - - - - - - - - - - - - - - | RFGS | FDY - - - - - - - - - |
| RT16 VH | - - - - - - - - - - - - - - - - - - - - - - - - - - - - | SSGRFV | FDY - - - - - - - - - |
| RT17 VH | - - - - - - - - - - - - - - - - - - - - - - - - - - - - | GRFGSV | FDY - - - - - - - - - |

|      | $k_a$ (M⁻¹S⁻¹) | $k_d$ (S⁻¹) | $K_D$ (M) |
|------|----------------|-------------|-----------|
| RT11 | $1.82 \times 10^4$ | $2.34 \times 10^{-4}$ | $1.29 \times 10^{-8}$ |

NIH3T3 – mCherry KRas G12V

Image magnification, 630x; scale bar, 5 μm.

NIH3T3 – mCherry KRas G12V

SEQUENCE LISTING

```
<160> NUMBER OF SEQ ID NOS: 46

<210> SEQ ID NO 1
<211> LENGTH: 118
<212> TYPE: PRT
<213> ORGANISM: Artificial Sequence
<220> FEATURE:
<223> OTHER INFORMATION: RT4

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser Thr Ile Ser Arg Ser Gly His Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Lys Arg Phe Gly Ser Ile Val Phe Asp Tyr Trp Gly Gln Gly Thr
            100                 105                 110

Leu Val Thr Val Ser Ser
            115

<210> SEQ ID NO 2
<211> LENGTH: 115
<212> TYPE: PRT
<213> ORGANISM: Artificial Sequence
<220> FEATURE:
<223> OTHER INFORMATION: RT11

<400> SEQUENCE: 2

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
            35                  40                  45

Ser Tyr Ile Ser Arg Thr Ser His Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Arg Gly Phe Phe Met Asp Tyr Trp Gly Gln Gly Thr Leu Val Thr
            100                 105                 110

Val Ser Ser
            115

<210> SEQ ID NO 3
<211> LENGTH: 116
<212> TYPE: PRT
<213> ORGANISM: Artificial Sequence
<220> FEATURE:
<223> OTHER INFORMATION: RT13

<400> SEQUENCE: 3

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Thr Phe
            20                  25                  30

Ser Met Ser Trp Val Arg Gln Ala Pro Gly Lys Gly Leu Glu Trp Val
            35                  40                  45

Ser Tyr Ile Ser Arg Thr Ser His Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Arg Gly Thr Phe Gly Phe Asp Tyr Trp Gly Gln Gly Thr Leu Val
            100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: RT14

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Ser Met Ser Trp Val Arg Gln Ala Pro Gly Lys Gly Leu Glu Trp Val
        35                  40                  45

Ser Tyr Ile Ser Arg Thr Ser His Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Gly Trp Phe Asp Tyr Trp Gly Gln Gly Thr Leu Val
            100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: RT15

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Ser Met Ser Trp Val Arg Gln Ala Pro Gly Lys Gly Leu Glu Trp Val
        35                  40                  45

Ser Tyr Ile Ser Arg Thr Ser His Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Phe Gly Ser Phe Asp Tyr Trp Gly Gln Gly Thr Leu Val
            100                 105                 110

Thr Val Ser Ser
        115

<210> SEQ ID NO 6
<211> LENGTH: 118
<212> TYPE: PRT
<213> ORGANISM: Artificial Sequence

<220> FEATURE:
<223> OTHER INFORMATION: RT16

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Ser Met Ser Trp Val Arg Gln Ala Pro Gly Lys Gly Leu Glu Trp Val
        35                  40                  45

Ser Tyr Ile Ser Arg Thr Ser His Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Gly Arg Phe Val Phe Asp Tyr Trp Gly Gln Gly Thr
            100                 105                 110

Leu Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: RT17

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Ser Met Ser Trp Val Arg Gln Ala Pro Gly Lys Gly Leu Glu Trp Val
        35                  40                  45

Ser Tyr Ile Ser Arg Thr Ser His Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Phe Gly Ser Val Phe Asp Tyr Trp Gly Gln Gly Thr
            100                 105                 110

Leu Val Thr Val Ser Ser
        115

<210> SEQ ID NO 8
<211> LENGTH: 5
<212> TYPE: PRT
<213> ORGANISM: Artificial Sequence
<220> FEATURE:
<223> OTHER INFORMATION: RT4 CDR1

<400> SEQUENCE: 8

Ser Tyr Ala Met Ser
1               5

```
<210> SEQ ID NO 9
<211> LENGTH: 17
<212> TYPE: PRT
<213> ORGANISM: Artificial Sequence
<220> FEATURE:
<223> OTHER INFORMATION: RT4 CDR2

<400> SEQUENCE: 9

Thr Ile Ser Arg Ser Gly His Ser Thr Tyr Tyr Ala Asp Ser Val Lys
1               5                   10                  15

Gly

<210> SEQ ID NO 10
<211> LENGTH: 9
<212> TYPE: PRT
<213> ORGANISM: Artificial Sequence
<220> FEATURE:
<223> OTHER INFORMATION: RT4 CDR3

<400> SEQUENCE: 10

Arg Phe Gly Ser Ile Val Phe Asp Tyr
1               5

<210> SEQ ID NO 11
<211> LENGTH: 5
<212> TYPE: PRT
<213> ORGANISM: Artificial Sequence
<220> FEATURE:
<223> OTHER INFORMATION: RT11 CDR1

<400> SEQUENCE: 11

Ser Tyr Ser Met Ser
1               5

<210> SEQ ID NO 12
<211> LENGTH: 17
<212> TYPE: PRT
<213> ORGANISM: Artificial Sequence
<220> FEATURE:
<223> OTHER INFORMATION: RT11 CDR2

<400> SEQUENCE: 12

Tyr Ile Ser Arg Thr Ser His Thr Thr Tyr Tyr Ala Asp Ser Val Lys
1               5                   10                  15

Gly

<210> SEQ ID NO 13
<211> LENGTH: 6
<212> TYPE: PRT
<213> ORGANISM: Artificial Sequence
<220> FEATURE:
<223> OTHER INFORMATION: RT11 CDR3

<400> SEQUENCE: 13

Gly Phe Phe Met Asp Tyr
1               5

<210> SEQ ID NO 14
<211> LENGTH: 5
<212> TYPE: PRT
<213> ORGANISM: Artificial Sequence
<220> FEATURE:
<223> OTHER INFORMATION: RT13 CDR1
```

```
<400> SEQUENCE: 14

Thr Phe Ser Met Ser
1               5

<210> SEQ ID NO 15
<211> LENGTH: 17
<212> TYPE: PRT
<213> ORGANISM: Artificial Sequence
<220> FEATURE:
<223> OTHER INFORMATION: RT13 CDR2

<400> SEQUENCE: 15

Tyr Ile Ser Arg Thr Ser His Thr Thr Tyr Tyr Ala Asp Ser Val Lys
1               5                   10                  15

Gly

<210> SEQ ID NO 16
<211> LENGTH: 7
<212> TYPE: PRT
<213> ORGANISM: Artificial Sequence
<220> FEATURE:
<223> OTHER INFORMATION: RT13 CDR3

<400> SEQUENCE: 16

Gly Thr Phe Gly Phe Asp Tyr
1               5

<210> SEQ ID NO 17
<211> LENGTH: 5
<212> TYPE: PRT
<213> ORGANISM: Artificial Sequence
<220> FEATURE:
<223> OTHER INFORMATION: RT14 CDR1

<400> SEQUENCE: 17

Thr Phe Ser Met Ser
1               5

<210> SEQ ID NO 18
<211> LENGTH: 17
<212> TYPE: PRT
<213> ORGANISM: Artificial Sequence
<220> FEATURE:
<223> OTHER INFORMATION: RT14 CDR2

<400> SEQUENCE: 18

Tyr Ile Ser Arg Thr Ser His Thr Thr Tyr Tyr Ala Asp Ser Val Lys
1               5                   10                  15

Gly

<210> SEQ ID NO 19
<211> LENGTH: 7
<212> TYPE: PRT
<213> ORGANISM: Artificial Sequence
<220> FEATURE:
<223> OTHER INFORMATION: RT14 CDR3

<400> SEQUENCE: 19

Pro Arg Gly Trp Phe Asp Tyr
1               5

<210> SEQ ID NO 20
<211> LENGTH: 5
<212> TYPE: PRT
<213> ORGANISM: Artificial Sequence
```

```
<220> FEATURE:
<223> OTHER INFORMATION: RT15 CDR1

<400> SEQUENCE: 20

Thr Phe Ser Met Ser
1               5

<210> SEQ ID NO 21
<211> LENGTH: 17
<212> TYPE: PRT
<213> ORGANISM: Artificial Sequence
<220> FEATURE:
<223> OTHER INFORMATION: RT15 CDR2

<400> SEQUENCE: 21

Tyr Ile Ser Arg Thr Ser His Thr Thr Tyr Tyr Ala Asp Ser Val Lys
1               5                   10                  15

Gly

<210> SEQ ID NO 22
<211> LENGTH: 7
<212> TYPE: PRT
<213> ORGANISM: Artificial Sequence
<220> FEATURE:
<223> OTHER INFORMATION: RT15 CDR3

<400> SEQUENCE: 22

Arg Phe Gly Ser Phe Asp Tyr
1               5

<210> SEQ ID NO 23
<211> LENGTH: 5
<212> TYPE: PRT
<213> ORGANISM: Artificial Sequence
<220> FEATURE:
<223> OTHER INFORMATION: RT16 CDR1

<400> SEQUENCE: 23

Thr Phe Ser Met Ser
1               5

<210> SEQ ID NO 24
<211> LENGTH: 17
<212> TYPE: PRT
<213> ORGANISM: Artificial Sequence
<220> FEATURE:
<223> OTHER INFORMATION: RT16 CDR2

<400> SEQUENCE: 24

Tyr Ile Ser Arg Thr Ser His Thr Thr Tyr Tyr Ala Asp Ser Val Lys
1               5                   10                  15

Gly

<210> SEQ ID NO 25
<211> LENGTH: 9
<212> TYPE: PRT
<213> ORGANISM: Artificial Sequence
<220> FEATURE:
<223> OTHER INFORMATION: RT16 CDR3

<400> SEQUENCE: 25

Ser Ser Gly Arg Phe Val Phe Asp Tyr
1               5
```

```
<210> SEQ ID NO 26
<211> LENGTH: 5
<212> TYPE: PRT
<213> ORGANISM: Artificial Sequence
<220> FEATURE:
<223> OTHER INFORMATION: RT17 CDR1

<400> SEQUENCE: 26

Thr Phe Ser Met Ser
1               5

<210> SEQ ID NO 27
<211> LENGTH: 17
<212> TYPE: PRT
<213> ORGANISM: Artificial Sequence
<220> FEATURE:
<223> OTHER INFORMATION: RT17 CDR2

<400> SEQUENCE: 27

Tyr Ile Ser Arg Thr Ser His Thr Thr Tyr Tyr Ala Asp Ser Val Lys
1               5                   10                  15

Gly

<210> SEQ ID NO 28
<211> LENGTH: 9
<212> TYPE: PRT
<213> ORGANISM: Artificial Sequence
<220> FEATURE:
<223> OTHER INFORMATION: RT17 CDR3

<400> SEQUENCE: 28

Gly Arg Phe Gly Ser Val Phe Asp Tyr
1               5

<210> SEQ ID NO 29
<211> LENGTH: 114
<212> TYPE: PRT
<213> ORGANISM: Artificial Sequence
<220> FEATURE:
<223> OTHER INFORMATION: hT2 VL

<400> SEQUENCE: 29

Asp Leu Val Met Thr Gln Ser Pro Ala Thr Leu Ser Leu Ser Pro Gly
1               5                   10                  15

Glu Arg Ala Thr Leu Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Val Tyr Tyr Cys Lys Gln
                85                  90                  95

Ser Tyr Tyr His Met Tyr Thr Phe Gly Gln Gly Thr Lys Val Glu Ile
            100                 105                 110

Lys Arg

<210> SEQ ID NO 30
<211> LENGTH: 114
<212> TYPE: PRT
<213> ORGANISM: Artificial Sequence
```

```
<220> FEATURE:
<223> OTHER INFORMATION: hT3 VL

<400> SEQUENCE: 30

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Tyr His Met Tyr Thr Phe Gly Gln Gly Thr Lys Val Glu Ile
            100                 105                 110

Lys Arg

<210> SEQ ID NO 31
<211> LENGTH: 114
<212> TYPE: PRT
<213> ORGANISM: Artificial Sequence
<220> FEATURE:
<223> OTHER INFORMATION: hT4 VL

<400> SEQUENCE: 31

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Tyr His Met Tyr Thr Phe Gly Gln Gly Thr Lys Val Glu Ile
            100                 105                 110

Lys Arg

<210> SEQ ID NO 32
<211> LENGTH: 17
<212> TYPE: PRT
<213> ORGANISM: Artificial Sequence
<220> FEATURE:
<223> OTHER INFORMATION: hT2 VL CDR1

<400> SEQUENCE: 32

Lys Ser Ser Gln Ser Leu Phe Asn Ser Arg Thr Arg Lys Asn Tyr Leu
1               5                   10                  15

Ala
```

```
<210> SEQ ID NO 33
<211> LENGTH: 7
<212> TYPE: PRT
<213> ORGANISM: Artificial Sequence
<220> FEATURE:
<223> OTHER INFORMATION: hT2 VL CDR2

<400> SEQUENCE: 33

Trp Ala Ser Thr Arg Glu Ser
1               5

<210> SEQ ID NO 34
<211> LENGTH: 9
<212> TYPE: PRT
<213> ORGANISM: Artificial Sequence
<220> FEATURE:
<223> OTHER INFORMATION: hT2 VL CDR3

<400> SEQUENCE: 34

Lys Gln Ser Tyr Tyr His Met Tyr Thr
1               5

<210> SEQ ID NO 35
<211> LENGTH: 17
<212> TYPE: PRT
<213> ORGANISM: Artificial Sequence
<220> FEATURE:
<223> OTHER INFORMATION: hT3 VL CDR1

<400> SEQUENCE: 35

Lys Ser Ser Gln Ser Leu Phe Asn Ser Arg Thr Arg Lys Asn Tyr Leu
1               5                   10                  15

Ala

<210> SEQ ID NO 36
<211> LENGTH: 7
<212> TYPE: PRT
<213> ORGANISM: Artificial Sequence
<220> FEATURE:
<223> OTHER INFORMATION: hT3 VL CDR2

<400> SEQUENCE: 36

Trp Ala Ser Thr Arg Glu Ser
1               5

<210> SEQ ID NO 37
<211> LENGTH: 9
<212> TYPE: PRT
<213> ORGANISM: Artificial Sequence
<220> FEATURE:
<223> OTHER INFORMATION: hT3 VL CDR3

<400> SEQUENCE: 37

Lys Gln Ser Tyr Tyr His Met Tyr Thr
1               5

<210> SEQ ID NO 38
<211> LENGTH: 17
<212> TYPE: PRT
<213> ORGANISM: Artificial Sequence
<220> FEATURE:
<223> OTHER INFORMATION: hT4 VL CDR1
```

```
<400> SEQUENCE: 38

Lys Ser Ser Gln Ser Leu Phe Asn Ser Arg Thr Arg Lys Asn Tyr Leu
1               5                   10                  15

Ala

<210> SEQ ID NO 39
<211> LENGTH: 7
<212> TYPE: PRT
<213> ORGANISM: Artificial Sequence
<220> FEATURE:
<223> OTHER INFORMATION: hT4 VL CDR2

<400> SEQUENCE: 39

Trp Ala Ser Thr Arg Glu Ser
1               5

<210> SEQ ID NO 40
<211> LENGTH: 9
<212> TYPE: PRT
<213> ORGANISM: Artificial Sequence
<220> FEATURE:
<223> OTHER INFORMATION: hT4 VL CDR3

<400> SEQUENCE: 40

Gln Gln Tyr Tyr Tyr His Met Tyr Thr
1               5

<210> SEQ ID NO 41
<211> LENGTH: 9
<212> TYPE: PRT
<213> ORGANISM: Artificial Sequence
<220> FEATURE:
<223> OTHER INFORMATION: RGD4C

<400> SEQUENCE: 41

Cys Asp Cys Arg Gly Asp Cys Phe Cys
1               5

<210> SEQ ID NO 42
<211> LENGTH: 13
<212> TYPE: PRT
<213> ORGANISM: Artificial Sequence
<220> FEATURE:
<223> OTHER INFORMATION: RGD10

<400> SEQUENCE: 42

Asp Gly Ala Arg Tyr Cys Arg Gly Asp Cys Phe Asp Gly
1               5                   10

<210> SEQ ID NO 43
<211> LENGTH: 114
<212> TYPE: PRT
<213> ORGANISM: Artificial Sequence
<220> FEATURE:
<223> OTHER INFORMATION: m3D8 VL

<400> SEQUENCE: 43

Asp Leu Val Met Ser Gln Ser Pro Ser Ser Leu Ala Val Ser Ala Gly
1               5                   10                  15

Glu Lys Val Thr Met Ser Cys Lys Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45
```

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                    85                  90                  95

Ser Tyr Tyr His Met Tyr Thr Phe Gly Ser Gly Thr Lys Leu Glu Ile
                100                 105                 110

Lys Arg

<210> SEQ ID NO 44
<211> LENGTH: 114
<212> TYPE: PRT
<213> ORGANISM: Artificial Sequence
<220> FEATURE:
<223> OTHER INFORMATION: hT0 VL

<400> SEQUENCE: 44

Asp Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Phe Asn Ser
                20                  25                  30

Arg Thr Arg Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Val Tyr Tyr Cys Lys Gln
                    85                  90                  95

Ser Tyr Tyr His Met Tyr Thr Phe Gly Gln Gly Thr Lys Val Glu Ile
                100                 105                 110

Lys Arg

<210> SEQ ID NO 45
<211> LENGTH: 108
<212> TYPE: PRT
<213> ORGANISM: Artificial Sequence
<220> FEATURE:
<223> OTHER INFORMATION: Adalimumab VL

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                    85                  90                  95

Thr Phe Gly Gln Gly Thr Lys Val Glu Ile Lys Arg
                100                 105

```
<210> SEQ ID NO 46
<211> LENGTH: 108
<212> TYPE: PRT
<213> ORGANISM: Artificial Sequence
<220> FEATURE:
<223> OTHER INFORMATION: Bevacizumab VL

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
                100                 105
```

METHOD FOR INHIBITING INTRACELLULAR ACTIVATED RAS USING INTACT IMMUNOGLOBULIN-TYPE ANTIBODY HAVING CYTOSOL-PENETRATING ABILITY AND USE THEREOF

CROSS-REFERENCE TO RELATED APPLICATIONS

This application is a U.S. national phase under the provisions of 35 U.S.C. § 371 of International Patent Application No. PCT/KR15/07627 filed Jul. 22, 2015, which in turn claims priority of Korean Patent Application No. 10-2014-0092687 filed Jul. 22, 2014 and Korean Patent Application No. 10-2015-0103214 filed Jul. 21, 2015. The disclosures of such international patent application and Korean priority patent applications are hereby incorporated herein by reference in their respective entireties, for all purposes.

TECHNICAL FIELD

The present invention relates to a method for inhibiting intracellular activated (GTP-bound) RAS using an intact immunoglobulin-type antibody having the ability to penetrate the cytosol, and to the use thereof.

Moreover, the present invention relates to a heavy-chain variable region (VH) which induces an intact immunoglobulin-type antibody to penetrate the cytosol and bind to activated RAS in the cytosol, and to an antibody comprising the same.

Also, the present invention relates to a method for inhibiting the growth of cancer or tumor cells using the antibody, and to a method for treating cancer or tumor.

Also, the present invention relates to a method for screening a heavy-chain variable region which binds specifically to RAS in the cytosol.

Also, the present invention relates to a biological active molecule fused to the antibody and selected from the group consisting of peptides, proteins, small-molecule drugs, nanoparticles and liposomes.

Also, the present invention relates to a composition for prevention, treatment or diagnosis of cancer, comprising: the antibody; or a biological active molecule fused to the antibody and selected from the group consisting of peptides, proteins, small-molecule drugs, nanoparticles and liposomes.

Also, the present invention relates to a polynucleotide that encodes the light-chain variable region and the antibody.

BACKGROUND ART

Intact immunoglobulin-type antibody has a highly stable Y-shaped structure (molecular weight: 150 kDa) composed of two heavy-chain (50 kDa) proteins and two light-chain (25 kDa) proteins. The antibody light-chain and heavy-chain are divided into variable regions whose amino acid sequences differ between antibodies, and constant regions whose amino acid sequences are the same between antibodies. The heavy-chain constant region includes CH1, hinge, CH2 and CH3 domains, and the light-chain constant region includes a Cκ or Cλ a domain. Antibody heavy-chain and light-chain variable regions have portions whose amino acid sequences particularly differ between antibodies, and these portions constitute antigen-binding sites, and thus are also called "complementarity determining regions (CDRs)". When the three-dimensional structures of antibodies are examined, these CDRs form a loop on the antibody surface. Below the loop, a framework region that structurally supports the loop exists. In each of the heavy chain and the light chain, three loop structures exist, and these six loop structures are combined with one another and come into direct contact with antigen. The heavy-chain constant region (Fc) of antibody guarantees a long half-life in blood by its binding to FcRn (neonatal Fc receptor), and due to this characteristic, the antibody can be long-lasting in the body, unlike small-molecule drugs. Furthermore, the binding of antibody to FcγR (Fc gamma receptor) or the like makes it possible to specifically induce the death of cells which overexpress a target substance, through antibody-dependent cellular cytotoxicity and complement-dependent cellular cytotoxicity. Antibodies recently developed in various species for the purpose of treating various diseases can exhibit improved therapeutic effects through various humanization methods such as a method of CDR-grafting with a human antibody FR (framework) in order to overcome immunogenicity.

Conventional antibodies cannot directly penetrate living cells due to their large size and hydrophilic nature. Thus, most conventional antibodies specifically target extracellularly secreted proteins or cell membrane proteins (Kim S J et al., 2005). General antibodies and macromolecular bio-drugs have limitations in that they cannot pass the hydrophobic cell membrane, and thus cannot bind to and inhibit various disease-related substances. Generally, commercial antibodies binding specifically to intracellular substances, which are used in experiments for studies on mechanisms such as the growth, specific inhibition, etc. of cells, cannot be used directly to treat living cells, and in order for these antibodies to bind to intracellular substances, a pretreatment process for forming pores in the cell membrane by a cell membrane permeabilization process using the amphipathic glycoside saponin is necessarily required. Small-molecule substances, nucleic acids or nanoparticles, etc., can be transported into living cells by use of various reagents or methods such as electroporation or heat shock, but proteins or antibodies can lose their activity, because the above-described most reagents and experimental conditions adversely affect the characteristic three-dimensional structures of the proteins or antibodies. Intracellular antibodies (intrabodies), which bind specifically to intracellular proteins and inhibit their activity, have been developed, but these antibodies also have no ability to penetrate the membrane of living cells, and thus may be applied only for gene therapy, and the applicability thereof in future is very limited (Manikandan J et al., 2007).

Unlike various types of antibody fragments, including intact immunoglobulin-type antibodies as described above, macromolecular substances such as recombinant proteins, etc., small-molecule substances easily and effectively penetrate living cells due to their small size and hydrophobic nature. However, in order for small-molecule drugs to bind specifically to various disease-related substances in cells, the surface of target substances is required to have a hydrophobic pocket. Target substances having this hydrophobic pocket form only about 10% of total disease-related substances in cells, and for this reason, small-molecule drugs cannot specifically target most pathogenic proteins in cells (Imai K et al., 2006).

In various diseases, including cancer, there occur the mutation and abdominal overexpression of either proteins that play an important role in intracellular protein-protein interactions (PPIs) or various proteins related to transcription or signaling. Among such proteins, particularly disease-related substances that show complex interactions through their large and flat surface are difficult to specifically inhibit by small-molecule drugs as described above (Blundell et al., 2006). As an example, RAS, which is one of cytosolic important tumor-related factors (therapeutic agents for which do not currently exist), acts as a molecular switch that transmits an extracellular signal through a cell membrane receptor to the intracellular signaling system. In about 30% of human cancers, particularly colorectal cancer and pancreatic cancer, RAS is always activated in cells due to cancer-related mutations, and such carcinogenesis-related mutations are known as major tumor-related factors that impart strong resistance to conventional anticancer therapy (Scheffzek K et al., 1997).

In an attempt to overcome current technical limitations, various studies have been conducted to impart cell-penetrating ability to antibody fragments or macromolecular substances, which can effectively inhibit protein-protein interactions. It was found that protein transduction domains (PTDs) having basic amino acid sequences and a hydrophobic or amphipathic nature have the ability to penetrate living cells (Leena N et al., 2007). Furthermore, many attempts have been made to fuse the protein transduction domains to various types of antibody fragments by genetic engineering methods in order to recognize specific intracellular proteins. However, most fusion proteins are not secreted from animal cells or are released into supernatants in only very small amounts (NaKajima O et al., 2004), and fusion proteins with a protein transduction domain rich in arginine have problems in that they are weak against host Furin protease during production (Chauhan A et al., 2007). In addition, there is a problem in that the cell-penetrating efficiency of fusion proteins is poor, making it difficult to develop these fusion proteins into therapeutic antibodies (Falnes P et al., 2001). In an attempt to overcome expression-associated problems, studies have been conducted to fuse cell-penetrating domains by chemical covalent bonds or biotin-streptavidin bonds after protein purification, but these methods result in the structural detypeion of proteins.

In addition, studies conducted using some autoantibodies reported that antibodies and short-chain variable region (scFv) antibody fragments can penetrate into cells by endocytosis. Autoantibodies are anti-DNA antibodies that are found mainly in humans and mice with autoimmune disease, and some of these autoantibodies have the property of penetrating living cells (Michael R et al., 1995; Michael P et al., 1996; Jeske Zack D et al., 1996). Cell-penetrating autoantibodies reported to date mostly localize to the nucleus after their introduction into cells, and studies have been actively conducted to fuse these cell-penetrating autoantibodies with specific proteins showing effects in the nucleus (Weisbart et al., 2012). However, protein penetration into living cells by use of autoantibodies has limitations in that the protein finally localize to the nucleus, and thus cannot bind specifically to various disease-related substances in the intracellular cytosol and cannot inhibit the activity thereof.

Among naturally occurring macromolecular substances, typical substances having the property of penetrating cells include viruses (HIV, HSV), toxins (cholera toxin, diphtheria toxin), etc. It is known that these substances penetrate cells by endocytosis that is an active intracellular transport mechanism. This endocytosis is largely classified into three pathways: endocytosis by clathrin that is involved in the internalization of a receptor by ligand binding; endocytosis by caveolae that are found in some toxins such as cholera toxin; and macropinocytosis that is found in dextran, Ebola virus, etc. Endocytosis in which clathrin and caveolae are involved mainly begins when receptors distributed on the cell membrane bind to specific ligands. Clathrin localizes to the inner surface of the cell membrane. When a substance binds to a receptor, the clathrin protein makes a fibrous shell to form a vesicle which moves into cells. Caveolae form an oligomer by action of caveolin-1 protein while forming a stable vesicle (caveosome) which moves into the cytosol. In macropinocytosis, a portion of the cell membrane protrudes to surround a substance to thereby form a macropinosome which moves into the cytosol (Gerber et al., 2013). Substances that penetrated the cytosol through such endocytosis pathways are mostly degraded through a lysosomal pathway in the absence of an additional endosomal escape mechanism.

In order to avoid from being degraded through the lysosomal pathway, viruses, toxins and the like have a mechanism by which they escape from the endosome into the cytosol. Although the endosomal escape mechanism has not yet been clearly found, three hypotheses for the endosomal escape mechanism are known to date. The first hypothesis is a mechanism by which a pore is formed in the endosomal membrane. In this hypothesis, substances such as cationic amphiphilic peptides in the endosomal membrane bind to a negatively charged cellular lipid bilayer to cause internal stress or inner membrane contraction to thereby form a barrel-stave pore or a toroidal channel (Jenssen et al., 2006). The second hypothesis is a mechanism by which the endosome bursts as a consequence of the proton-sponge effect. In this hypothesis, due to the high buffering effect of a substance having a protonated amino group, the osmotic pressure of the endosome can be increased so that the endosomal membrane can be degraded (Lin and Engbersen, 2008). In the third hypothesis, a specific motif, which maintains a hydrophilic coil shape in a neutral environment but is changed into a hydrophobic helical structure in an acidic environment such as endosome, escapes from the endosome by fusion to the endosomal membrane (Horth et al., 1991). However, studies conducted to demonstrate endosome escape mechanisms for a variety of naturally occurring substances based on the above-described hypotheses are still insufficient.

Accordingly, the present inventors have construct a heavy-chain variable region (VH) library to select a heavy-chain variable region (VH) having the ability to bind specifically to activated RAS, and have co-expressed a light chain having a humanized light-chain variable region (VL), which penetrates living cells and localizes in the cytosol, with the selected heavy-chain variable region (VH), thereby constructing an intact immunoglobulin-type anti-RAS cytosol-penetrating antibody (iMab (internalizing & interfering monoclonal antibody)) that can penetrate living cells and bind specifically to activated RAS in the cytosol.

Moreover, the present inventors have developed a humanized light-chain variable (VL) single domain that penetrates cells and localizes in the cytosol to discover an intact immunoglobulin-type antibody which penetrates living cells and localizes in the cytosol. Furthermore, in order to construct a stable intact immunoglobulin-type monoclonal antibody, the present inventors have improved a light-chain variable single domain (VL) antibody fragment having cytosol-penetrating ability so as to easily interact with and bind to various human heavy-chain variable regions (VH) while maintaining its ability to penetrate cells and localize in the cytosol, thereby developing an intact immunoglobulin-type monoclonal antibody that penetrates cells and localize in the cytosol.

Furthermore, the present inventors have found that the anti-RAS cytosol-penetrating monoclonal antibody penetrates various RAS-dependent cancer cell lines and inhibits cell growth by specifically neutralization of RAS in the cytosol, and have found that, even when the antibody is fused with a peptide for imparting tumor tissue specificity, it exhibits an activity of specifically inhibiting activated RAS in RAS-dependent tumors without adversely affecting the ability to penetrate the cytosol and neutralize activated RAS, thereby completing the present invention.

DISCLOSURE OF INVENTION

Technical Problem

Therefore, it is an object of the present invention to provide a method for inhibiting intracellular activated RAS using an intact immunoglobulin-type antibody having the ability to penetrate the cytosol.

Another object of the present invention is to provide a heavy-chain variable region (VH) which induces an intact immunoglobulin-type antibody to penetrate the cytosol and bind to activated RAS in the cytosol, and to an antibody comprising the same.

Still another object of the present invention is to provide a method for inhibiting the growth of cancer or tumor cells using the antibody, and to a method for treating cancer or tumor Still another object of the present invention is to provide a method for screening a heavy-chain variable region which binds specifically to RAS in the cytosol.

Still another object of the present invention is to provide a biological active molecule fused to the antibody and selected from the group consisting of peptides, proteins, small-molecule drugs, nanoparticles and liposomes.

Yet another object of the present invention is to provide a composition for prevention, treatment or diagnosis of cancer, comprising: the antibody; or a biological active molecule fused to the antibody and selected from the group consisting of peptides, proteins, small-molecule drugs, nanoparticles and liposomes.

Yet another object of the present invention is to provide a polynucleotide that encodes the light-chain variable region and the antibody.

Technical Solution

To achieve the above object, the present invention provides a method for inhibiting intracellular activated RAS using an intact immunoglobulin-type antibody which actively penetrates the cytosol of living cells through endocytosis and endosomal escape, wherein the antibody binds specifically to activated RAS in the cytosol.

Hereinafter, the present invention will be described in detail.

The method of the present invention inhibits intracellular activated RAS through a heavy-chain variable region (VH) which induces an intact immunoglobulin-type antibody to penetrate the cytosol and bind to activated RAS in the cytosol.

According to the present invention, a light-chain variable region (VL), which can induce an intact immunoglobulin-type antibody to permeate the membrane of living cells through endocytosis and to be localized in the cytosol through endosomal escape, allows the intact immunoglobulin-type antibody to penetrate the cell membrane and to localize in the cytosol.

Namely, the method of the present invention provides a method of inducing an antibody to penetrate the cytosol and to bind specifically to activated (GRP-bound) RAS (tumor-related factor) in the cytosol and to inhibit the activity of the RAS.

The antibody may be a chimeric, human or humanized antibody.

The antibody may be IgG, IgM, IgA, IgD, or IgE. For example, the antibody may be IgG1, IgG2, IgG3, IgG4, IgM, IgE, IgA1, IgA5, or IgD, and may be most preferably IgG type monoclonal antibody.

In the present invention, an intact immunoglobulin-type antibody has a structure with two full-length light chains and two full-length heavy chains, and each light chain is linked to each heavy chain by a disulfide bond (SS-bond). A constant region of the antibody is divided into a heavy-chain constant region and a light-chain constant region, and the heavy-chain constant region has γ, μ, α, δ, and ε types, and γ1, γ2, γ3, γ4, α1 and α2 subclasses. The light-chain constant region has κ and λ types.

The term "heavy chain" as used herein may be interpreted to include a full-length heavy chain including variable region domain VH including an amino acid sequence having a variable region sequence sufficient to confer antigen-specificity and three constant region domains CH1, CH2 and CH3, and a fragment thereof. Also, the term "light chain" as used herein may be interpreted to include a full-length light chain including a variable region domain VL including an amino acid sequence having a variable region sequence sufficient to confer antigen-specificity and a constant region domain CL, and a fragment thereof.

In an embodiment of the present invention, the antibody may be an antibody that targets and binds specifically to activated RAS in the cytosol. The activated RAS may be a GTP-bound tumor-related factor, and the RAS may be mutated RAS. Mutations of the RAS may be various mutations related to diseases, and examples thereof include, but are not limited to, substitution mutations at glycine 12, glycine 13 and glutamine 61 of KRas, HRas or NRas.

The binding of the intact immunoglobulin-type antibody to intracellular activated RAS is caused by the heavy-chain variable region (VH) which binds specifically to activated RAS in the cytosol.

In one aspect of the present invention, the heavy-chain variable region (VH) which binds specifically to activated RAS in the cytosol may comprise:

a CDR1 comprising an amino acid sequence, which has at least 90% homology with an amino acid sequence selected from the group consisting of as set forth in SEQ ID Nos: 8, 11, 14, 17, 20, 23, and 26;

a CDR2 comprising an amino acid sequence, which has at least 90% homology with an amino acid sequence selected from the group consisting of as set forth in SEQ ID Nos: 9, 12, 15, 18, 21, 24, and 27; and a CDR3 comprising an amino acid sequence, which has at least 90% homology with an amino acid sequence selected from the group consisting of as set forth in SEQ ID Nos: 10, 13, 16, 19, 22, 25, and 28.

Information about the sequences the heavy-chain variable regions is as follows:

| Names of heavy-chain variable regions Kabat No. | CDR1 Sequence | | | | | SEQ ID NO: | CDR2 Sequence | | | | | | | | | | | | | | | SEQ ID NO: |
|---|---|---|---|---|---|---|---|---|---|---|---|---|---|---|---|---|---|---|---|---|---|---|---|
| | 31 | 32 | 33 | 34 | 35 | | 50 | 51 | 52 | 52a | 53 | 54 | 55 | 56 | 57 | 58 | 59 | 60 | 61 | 62 | 63 | 64 | 65 | |
| RT4 | S | Y | A | M | S | 8 | T | I | S | R | S | G | H | S | T | Y | Y | A | D | S | V | K | G | 9 |
| RT11 | S | Y | S | M | S | 11 | Y | I | S | R | T | S | H | T | T | Y | Y | A | D | S | V | K | G | 12 |
| RT13 | T | F | S | M | S | 14 | Y | I | S | R | T | S | H | T | T | Y | Y | A | D | S | V | K | G | 15 |
| RT14 | T | F | S | M | S | 17 | Y | I | S | R | T | S | H | T | T | Y | Y | A | D | S | V | K | G | 18 |
| RT15 | T | F | S | M | S | 20 | Y | I | S | R | T | S | H | T | T | Y | Y | A | D | S | V | K | G | 21 |
| RT16 | T | F | S | M | S | 23 | Y | I | S | R | T | S | H | T | T | Y | Y | A | D | S | V | K | G | 24 |
| RT17 | T | F | S | M | S | 26 | Y | I | S | R | T | S | H | T | T | Y | Y | A | D | S | V | K | G | 27 |

| Names of heavy-chain variable regions Kabat No. | CDR3 Sequence | | | | | | | | SEQ ID NO: |
|---|---|---|---|---|---|---|---|---|---|
| | 95 | 96 | 97 | 98 | 99 | 100 | 100a | 101 | 102 | |
| RT4 | R | F | G | S | I | V | F | D | Y | 10 |
| RT11 | G | F | F | – | – | – | M | D | Y | 13 |
| RT13 | G | T | F | G | – | – | F | D | Y | 16 |
| RT14 | P | R | G | W | – | – | F | D | Y | 19 |
| RT15 | R | F | G | S | – | – | F | D | Y | 22 |
| RT16 | S | S | G | R | F | V | F | D | Y | 25 |
| RT17 | G | R | F | G | S | V | F | D | Y | 28 |

In an embodiment of the present invention, the heavy-chain variable region of the present invention may comprise a CDR1 of SEQ ID NO: 8, a CDR2 of SEQ ID NO: 9, and a CDR3 of SEQ ID NO: 10.

In an embodiment of the present invention, the heavy-chain variable region of the present invention may comprise a CDR1 of SEQ ID NO: 11, a CDR2 of SEQ ID NO: 12, and a CDR3 of SEQ ID NO: 13.

In an embodiment of the present invention, the heavy-chain variable region of the present invention may comprise a CDR1 of SEQ ID NO: 14, a CDR2 of SEQ ID NO: 15, and a CDR3 of SEQ ID NO: 16.

In an embodiment of the present invention, the heavy-chain variable region of the present invention may comprise a CDR1 of SEQ ID NO: 17, a CDR2 of SEQ ID NO: 18, and a CDR3 of SEQ ID NO: 19.

In an embodiment of the present invention, the heavy-chain variable region of the present invention may comprise a CDR1 of SEQ ID NO: 20, a CDR2 of SEQ ID NO: 21, and a CDR3 of SEQ ID NO: 22.

In an embodiment of the present invention, the heavy-chain variable region of the present invention may comprise a CDR1 of SEQ ID NO: 23, a CDR2 of SEQ ID NO: 24, and a CDR3 of SEQ ID NO: 25.

In an embodiment of the present invention, the heavy-chain variable region of the present invention may comprise a CDR1 of SEQ ID NO: 26, a CDR2 of SEQ ID NO: 27, and a CDR3 of SEQ ID NO: 28.

Also, a preferable embodiment of the present invention, the heavy-chain variable region (VH) may consist of an amino acid sequence selected from the group consisting of SEQ ID NOs: 1 to 7.

Information about the sequences of the heavy-chain variable regions is as follows:

| Names of heavy-chain variable regions | Sequence | SEQ ID NO: |
|---|---|---|
| RT4 | EVQLVESGGGLVQPGGSLRLSCAASGFTFS SYAMSWVRQAPGKGLEWVSTISRSGHSTYY ADSVKGRFTISRDNSKNTLYLQMNSLRAED TAVYYCAKRFGSIVFDYWGQGTLVTVSS | SEQ ID NO: 1 |
| RT11 | EVQLVESGGGLVQPGGSLRLSCAASGFTFS SYSMSWVRQAPGKGLEWVSYISRTSHTTYY ADSVKGRFTISRDNSKNTLYLQMNSLRAED TAVYYCARGFF---MDYWGQGTLVTVSS | SEQ ID NO: 2 |

| Names of heavy-chain variable regions | Sequence | SEQ ID NO: |
|---|---|---|
| RT13 | EVQLVESGGGLVQPGGSLRLSCAASGFTFS TFSMSWVRQAPGKGLEWVSYISRTSHTTYY ADSVKGRFTISRDNSKNTLYLQMNSLRAED TAVYYCARGTFG--FDYWGQGTLVTVSS | SEQ ID NO: 3 |
| RT14 | EVQLVESGGGLVQPGGSLRLSCAASGFTFS TFSMSWVRQAPGKGLEWVSYISRTSHTTYY ADSVKGRFTISRDNSKNTLYLQMNSLRAED TAVYYCARPRGW--FDYWGQGTLVTVSS | SEQ ID NO: 4 |
| RT15 | EVQLVESGGGLVQPGGSLRLSCAASGFTFS TFSMSWVRQAPGKGLEWVSYISRTSHTTYY ADSVKGRFTISRDNSKNTLYLQMNSLRAED TAVYYCAKRFGS--FDYWGQGTLVTVSS | SEQ ID NO: 5 |
| RT16 | EVQLVESGGGLVQPGGSLRLSCAASGFTFS TFSMSWVRQAPGKGLEWVSYISRTSHTTYY ADSVKGRFTISRDNSKNTLYLQMNSLRAED TAVYYCARSSGRFVFDYWGQGTLVTVSS | SEQ ID NO: 6 |
| RT17 | EVQLVESGGGLVQPGGSLRLSCAASGFTFS TFSMSWVRQAPGKGLEWVSYISRTSHTTYY ADSVKGRFTISRDNSKNTLYLQMNSLRAED TAVYYCAKGRFGSVFDYWGQGTLVTVSS | SEQ ID NO: 7 |

The heavy-chain variable region, which binds specifically to RAS and inhibits the activity thereof, was screened by the following method.

In an example of the present invention, screening was performed using a library in which artificial mutations at a total of 18 residues in CDR1, CDR2 and CDR3 regions were induced in a state in which a constructed human heavy-chain variable region (VH) and a heavy-chain constant region (CH1) were fused to each other.

In an example of the present invention, using a library in which the human heavy-chain variable region (VH) and the heavy-chain constant region (CH1) were fused to each other, a heavy-chain variable region was selected, which can bind specifically to activated (GTP-bound) RAS even in a state in which it is fused to a cytosol-penetrating humanized light-chain variable region (VL).

In an example of the present invention, KRas G12D which is an activated (GTP-bound) RAS mutant was used as a target molecule. In one embodiment, cancer-associated RAS mutations occur mainly at residues 12, 13 and 61, in which residues 12 and 13 are located in the P-loop of the RAS protein, and affect the binding of GAP (GTPase-activating protein) that hydrolyzes GTP bound to the RAS protein to induce the change of the protein structure to an inactivated form. Furthermore, residue 61 binds to the hydrolytic active site of GAP to prevent the hydrolysis of GTP. Thus, various cancer-associated RAS mutations are not limited to KRas G12D mutations, because signaling-associated regions (Switch I and Switch II) thereof are equal to those of RAS G12D mutations.

Also, in one embodiment, a catalytic domain ranging from residue 1 to residue 165 in each of NRas and HRas has a similarity of at least 85% to that in KRas. In the catalytic domain, Switch I (residues 32 to 38) and Switch II (residues 59 to 67), which bind to downstream signaling substances, are perfectly consistent with those in KRas. However, the C-terminal early domain ranging from residue 165 to residue 189 has a similarity of 15%, but the structure thereof does not influence downstream signaling. Thus, the target molecule used is not limited to activated KRas G12D.

In an example of the present invention, using a yeast cell surface display system, initial screening was performed for activated (GTP-bound) RAS in a state in which the heavy-chain variable region (VH) and the heavy-chain constant region (CH1) were expressed. Thereafter, Fab was screened by mating with yeast that expresses and secretes a light chain comprising the cytosol-penetrating light-chain variable region (VL) and the light-chain constant region (CL).

In an embodiment of the present invention, the antibody is able to actively penetrate living cells. This ability to penetrate the cytosol is the ability to penetrate cells by endocytosis, and then localize in the cytosol by endosomal escape.

This ability to penetrate the cytosol can be exhibited by the cytosol-penetrating light-chain variable region (VL) of the antibody.

In one embodiment of the present invention, the light-chain variable region may comprise:

a CDR1 comprising an amino acid sequence, which has at least 90% homology with an amino acid sequence selected from the group consisting of as set forth in SEQ ID Nos: 32, 35 and 38; and a CDR3 comprising an amino acid sequence, which has at least 90% homology with an amino acid sequence selected from the group consisting of as set forth in SEQ ID Nos: 34, 27 and 40.

Information about the sequences of the light-chain variable regions is as follows:

| Names of light-chain variable regions | CDR1 Sequence | | | | | | | | | | | | | | | | SEQ ID NO: | CDR2 Sequence | | | | | | | SEQ ID NO: |
|---|---|---|---|---|---|---|---|---|---|---|---|---|---|---|---|---|---|---|---|---|---|---|---|---|
| Kabat No. | 24 | 25 | 26 | 27 | 27a | 27b | 27c | 27d | 27e | 27f | 28 | 29 | 30 | 31 | 32 | 33 | 34 | | 50 | 51 | 52 | 53 | 54 | 55 | 56 |
| hT2 VL | K | S | S | Q | S | L | F | N | S | R | T | R | K | N | Y | L | A | 32 | W | A | S | T | R | E | S | 33 |
| hT3 VL | K | S | S | Q | S | L | F | N | S | R | T | R | K | N | Y | L | A | 35 | W | A | S | T | R | E | S | 36 |
| hT4 VL | K | S | S | Q | S | L | F | N | S | R | T | R | K | N | Y | L | A | 38 | W | A | S | T | R | E | S | 39 |

| Names of light-chain variable regions | CDR3 Sequence | | | | | | | | | SEQ ID NO: |
|---|---|---|---|---|---|---|---|---|---|---|
| Kabat No. | 89 | 90 | 91 | 92 | 93 | 94 | 95 | 96 | 97 | |
| hT2 VL | K | Q | S | Y | Y | H | M | Y | T | 34 |
| hT3 VL | K | Q | S | Y | Y | H | M | Y | T | 37 |
| hT4 VL | Q | Q | Y | Y | Y | H | M | Y | T | 40 |

Also, in one embodiment of the present invention, the light-chain variable region may further comprise either a CDR2 consisting of an amino acid sequence selected from the group consisting of SEQ ID NOs: 33, 36 and 39, or a sequence having a homology of at least 90% to the CDR2.

In one embodiment of the present invention, the light-chain variable region may comprise CDR1 of SEQ ID NO: 32, CDR2 of SEQ ID NO: 33, and CDR3 of SEQ ID NO: 34.

Also, in another embodiment of the present invention, the light-chain variable region may comprise CDR1 of SEQ ID NO: 35, CDR2 of SEQ ID NO: 36, and CDR3 of SEQ ID NO: 37.

Also, in another embodiment of the present invention, the light-chain variable region may comprise CDR1 of SEQ ID NO: 38, CDR2 of SEQ ID NO: 39, and CDR3 of SEQ ID NO: 40.

In one embodiment of the present invention, the light-chain variable region may be one wherein $2^{nd}$ and $4^{th}$ amino acids, numbered starting from the N-terminus of the light-chain variable region, are substituted with leucine (L) and methionine (M), respectively.

This light-chain variable region is one obtained by substituting the $2^{nd}$ and $4^{th}$ residues important to obtain a CDR structure that retains its ability to penetrate cytosol, among residues included in the CDR Vernier zone located in the FR (framework).

In one embodiment of the present invention, the light-chain variable region may be one wherein $9^{th}$, $10^{th}$, $13^{th}$, $15^{th}$, $17^{th}$, $19^{th}$, $21^{st}$, $22^{nd}$, $42^{nd}$, $45^{th}$, $58^{th}$, $60^{th}$, $79^{th}$ and $85^{th}$ amino acids, numbered starting from the N-terminus of the light-chain variable region, are substituted with serine (S), serine (S), alanine (A), valine (V), aspartic acid (D), valine (V), isoleucine (I), threonine (T), lysine (K), lysine (K), valine (V), serine (S), glutamine (Q) and threonine (T), respectively.

This light-chain variable region is one obtained based on the sequencing results indicating that a total of 14 residues differ from those in Trastuzumab (Herceptin) which is high stable and comprising the heavy-chain variable region of the VH3 subgroup and the light-chain variable region of the Vκ1 subgroup, among commercially available humanized antibodies approved by the FDA.

In another embodiment of the present invention, the light-chain variable region may be one wherein $89^{th}$ and $91^{st}$ amino acids, numbered starting from the N-terminus of the light-chain variable region, are substituted with glutamine (Q) and tyrosine (Y), respectively.

This light-chain variable region is one obtained based on the results of analysis of VH-VL interface residues between human antibody variable regions, which indicate that two residues in the mouse CDR3 of a conventional cytosol-penetrating light-chain variable region differ.

In a preferred embodiment of the present invention, the light-chain variable region may comprise an amino acid sequence selected from the group consisting of SEQ ID NOs: 29, 30 and 31.

Information about the sequences of the light-chain variable regions is as follows:

| Names of light-chain variable regions | Sequence | SEQ ID NO: |
|---|---|---|
| hT2 VL | 1          10          20     abc<br>DLVMTQSPATLSLSPGERATLSCKSSQSLF<br>def    30          40          50<br>NSRTRKNYLAWYQQKPGQAPRLLIYWASTR<br>       60          70          80<br>ESGIPDRFSGSGSGTDFTLTISSLEPEDFA<br>       90         100<br>VYYCKQSYYHMYTFGQGTKVEIKR | 29 |
| hT3 VL | 1          10          20     abc<br>DLVMTQSPSSLSASVGDRVTITCKSSQSLF<br>def    30          40          50<br>NSRTRKNYLAWYQQKPGKAPKLLIYWASTR<br>       60          70          80<br>ESGVPSRFSGSGSGTDFTLTISSLQPEDFA<br>       90         100<br>TYYCKQSYYHMYTFGQGTKVEIKR | 30 |
| hT4 VL | 1          10          20     abc<br>DLVMTQSPSSLSASVGDRVTITCKSSQSLF<br>def    30          40          50<br>NSRTRKNYLAWYQQKPGKAPKLLIYWASTR<br>       60          70          80<br>ESGVPSRFSGSGSGTDFTLTISSLQPEDFA<br>       90         100<br>TYYCQQYYYHMYTFGQGTKVEIKR | 31 |

It should be noted that all the residues indicated in SEQ ID NOs provided herein were numbered according to the Kabat numbering system (Kabat E A et al., 1991). In one embodiment of the present invention, the binding of the antibody to activated RAS in the cytosol may inhibit the binding of activated RAS to B-Raf, C-Raf or PI3K.

One aspect of the present invention provides a heavy-chain variable region (VH) which induces an intact immunoglobulin-type antibody to penetrate the cytosol and bind to activated RAS in the cytosol.

In one aspect of the present invention, the heavy-chain variable region (VH) may comprise:

a CDR1 comprising an amino acid sequence, which has at least 90% homology with an amino acid sequence selected from the group consisting of as set forth in SEQ ID Nos: 8, 11, 14, 17, 20, 23, and 26;

a CDR2 comprising an amino acid sequence, which has at least 90% homology with an amino acid sequence selected from the group consisting of as set forth in SEQ ID Nos: 9, 12, 15, 18, 21, 24, and 27; and a CDR3 comprising an amino acid sequence, which has at least 90% homology with an amino acid sequence selected from the group consisting of as set forth in SEQ ID Nos: 10, 13, 16, 19, 22, 25, and 28.

Also, in one embodiment of the present invention, the heavy-chain variable region (VH) may comprise an amino acid sequence selected from the group consisting of SEQ ID NOs: 1 to 7.

Also, one aspect of the present invention provides an antibody comprising the heavy-chain variable region (VH).

Also, in one embodiment of the present invention, the antibody is one that actively penetrates living cells and binds specifically to activated RAS in the cytosol.

The antibody may be a chimeric, human or humanized antibody.

Also, in one embodiment of the present invention, the antibody may be any one selected from the group consisting of IgG, IgM, IgA, IgD, and IgE.

Also, the antibody may comprise a light-chain variable region (VL) having the ability to penetrate the cytosol. The ability to penetrate the cytosol may be the ability to penetrate cells by endocytosis, and then localize in the cytosol by endosome escape.

In one embodiment of the present invention, the light-chain variable region may comprise:

either a CDR1 consisting of an amino acid sequence selected from the group consisting of SEQ ID NOs: 32, 35 and 38, or a sequence having a homology of at least 90% to the CDR1; and either a CDR3 consisting of an amino acid sequence selected from the group consisting of SEQ ID NOs: 34, 27 and 40, or a sequence having a homology of at least 90% to the CDR3.

In one embodiment of the present invention, the light-chain variable region may be one wherein amino acids 2 and 4, numbered starting from the N-terminus of the light-chain variable region, are substituted with leucine (L) and methionine (M), respectively.

In one embodiment of the present invention, the light-chain variable region may be one wherein $9^{th}$, $10^{th}$, $13^{th}$, $15^{th}$, $17^{th}$, $19^{th}$, $21^{st}$, $22^{nd}$, $42^{nd}$, $45^{th}$, $58^{th}$, $60^{th}$, $79^{th}$ and $85^{th}$ amino acids, numbered starting from the N-terminus of the light-chain variable region, are substituted with serine (S), serine (S), alanine (A), valine (V), aspartic acid (D), valine (V), isoleucine (I), threonine (T), lysine (K), lysine (K), valine (V), serine (S), glutamine (Q) and threonine (T), respectively.

In another embodiment of the present invention, the light-chain variable region may be one wherein $89^{th}$ and $91^{st}$ amino acids, numbered starting from the N-terminus of the light-chain variable region, are substituted with glutamine (Q) and tyrosine (Y), respectively.

In a preferred embodiment of the present invention, the light-chain variable region may comprise an amino acid sequence selected from the group consisting of SEQ ID NOs: 29, 30 and 31.

One aspect of the present invention provides a method for inhibiting the growth of cancer or tumor cells, the method comprising a step of exposing a subject's cells to an antibody which binds specifically to activated RAS in the cytosol.

One aspect of the present invention also provides a method for treating cancer or tumor, the method comprising a step of administering to a subject a pharmaceutically effective amount of an antibody which binds specifically to activated RAS in the cytosol.

The antibody that binds specifically to activated RAS in the cytosol may be an antibody that can penetrate living cells and specifically recognize activated (GTP-bound) RAS in the cytosol, and it can target activated (GTP-bound) RAS in the cytosol of living cells and inhibit the activity of the RAS. Accordingly, the antibody heavy-chain variable region according to the present invention or an antibody comprising the same can selectively inhibit mutations of the major drug resistance-related factor RAS of conventional various tumor therapeutic agents, and thus can inhibit the growth of cancer or tumor and can treat cancer or tumor.

Another aspect of the present invention provides a method for screening a heavy-chain variable region which binds specifically to RAS in the cytosol.

The screening method comprises the steps of:

(1) expressing a heavy-chain variable region library, which can bind to GTP-bound RAS, by use of a yeast surface display system;

(2) binding the library to GTP-bound RAS; and (3) measuring the affinity of the library for the GTP-bound RAS.

Another aspect of the present invention relates to a biological active molecule fused to the antibody and selected from the group consisting of peptides, proteins, small-molecule drugs, nanoparticles and liposomes.

The proteins may be antibodies, antibody fragments, immuoglubulin, peptides, enzymes, growth factors, cytokines, transcription factors, toxins, antigen peptides, hormones, carrier proteins, motor function proteins, receptors, signaling proteins, storage proteins, membrane proteins, transmembrane proteins, internal proteins, external proteins, secretory proteins, viral proteins, glycoproteins, cleaved proteins, protein complexes, chemically modified proteins, or the like.

A specific embodiment of the present invention provides an RGD4C peptide comprising an amino acid sequence of SEQ ID NO: 41 or an RGD10 peptide comprising an amino acid sequence of SEQ ID NO: 42, which is fused to the N-terminus of the light-chain variable region of an intact immunoglobulin-type antibody that binds specifically to and inhibits activated (CTP-bound) RAS by cytosolic penetration. In an embodiment, the RGD4C peptide was fused to the N-terminus of the light-chain variable region by a $(G_4S)_1$ linker, and is preferably fused to the N-terminus of the light-chain variable region by a $(G_4S)_1$ linker, but is not limited thereto.

As used herein, the term "small-molecule drugs" refers to organic compounds, inorganic compounds or organometallic compounds that have a molecular weight of less than about 1000 Da and are active as therapeutic agents against diseases. The term is used in a broad sense herein. The small-molecule drugs herein encompass oligopeptides and other biomolecules having a molecular weight of less than about 1000 Da.

In the present invention, a nanoparticle refers to a particle including substances ranging between 1 and 1,000 nm in diameter. The nanoparticle may be a metal nanoparticle, a metal/metal core shell complex consisting of a metal nanoparticle core and a metal shell enclosing the core, a metal/non-metal core shell consisting of a metal nanoparticle core and a non-metal shell enclosing the core, or a non-metal/metal core shell complex consisting of a non-metal nanoparticle core and a metal shell enclosing the core. According to an embodiment, the metal may be selected from gold, silver, copper, aluminum, nickel, palladium, platinum, magnetic iron and oxides thereof, but is not limited thereto, and the non-metal may be selected from silica, polystyrene, latex and acrylate type substances, but is not limited thereto.

In the present invention, liposomes include at least one lipid bilayer enclosing the inner aqueous compartment, which is capable of being associated by itself. Liposomes may be characterized by membrane type and size thereof. Small unilamellar vesicles (SUVs) may have a single membrane and may range between 20 and 50 nm in diameter. Large unilamellar vesicles (LUVs) may be at least 50 nm in diameter. Oliglamellar large vesicles and multilamellar large vesicles may have multiple, usually concentric, membrane layers and may be at least 100 nm in diameter. Liposomes with several nonconcentric membranes, i.e., several small vesicles contained within a larger vesicle, are referred to as multivesicular vesicles.

As used herein, the term "fusion" refers to unifying two molecules having the same or different function or structure, and the methods of fusing may include any physical, chemical or biological method capable of binding the tumor tissue-penetrating peptide to the protein, small-molecule drug, nanoparticle or liposome. Preferably, the fusion may be made by a linker peptide, and for example, the linker peptide may mediate the fusion with the bioactive molecules at various locations of an antibody light-chain variable region of the present invention, an antibody, or fragments thereof.

The present invention also provides a pharmaceutical composition for prevention or treatment of cancer, comprising: the antibody; or a biologically active molecule fused to the antibody and selected from the group consisting of peptides, proteins, small-molecule drugs, nanoparticles and liposomes.

The cancer may be selected from the group consisting of squamous cell carcinoma, small cell lung cancer, non-small cell lung cancer, adenocarcinoma of lung, squamous cell carcinoma of lung, peritoneal cancer, skin cancer, skin or ocular melanoma, rectal cancer, anal cancer, esophageal cancer, small intestine cancer, endocrine cancer, parathyroid cancer, adrenal cancer, soft tissue sarcoma, urethral cancer, chronic or acute leukemia, lymphoma, hepatoma, gastrointestinal cancer, pancreatic cancer, glioblastoma, cervical cancer, ovarian cancer, liver cancer, bladder cancer, liver tumor, breast cancer, colon cancer, colorectal cancer, endometrial cancer or uterine cancer, salivary gland cancer, kidney cancer, liver cancer, prostate cancer, vulva cancer, thyroid cancer, liver cancer and head and neck cancer.

When the composition is prepared as a pharmaceutical composition for preventing or treating cancer or angiogenesis-related diseases, the composition may include a pharmaceutically acceptable carrier. The pharmaceutically acceptable carrier contained in the composition is typically used in the formulation. Examples of the pharmaceutically acceptable carrier included in the composition may include, but are not limited to, lactose, dextrose, sucrose, sorbitol, mannitol, starch, acacia rubber, calcium phosphate, alginate, gelatin, calcium silicate, minute crystalline cellulose, polyvinyl pyrrolidone, cellulose, water, syrup, methyl cellulose, methyl hydroxy benzoate, propyl hydroxy benzoate, talc, magnesium stearate and mineral oil, etc., but are not limited thereto. In addition to the above ingredients, the pharmaceutical composition may further include a lubricant, a wetting agent, a sweetener, a flavoring agent, an emulsifier, a suspension, a preservative, etc.

The pharmaceutical composition for preventing or treating cancer or angiogenesis-related diseases may be administered orally or parenterally. Such a parenteral administration includes intravenous injection, subcutaneous injection, intramuscular injection, intraperitoneal injection, endothelial administration, topical administration, nasal administration, intrapulmonary administration, intrarectal administration, etc. Because a protein or peptide is digested when administered orally, it is preferred that a composition for oral administration is formulated to coat an active substance or to be protected against degradation in stomach. Also, the pharmaceutical composition may be administered by any device which can transport active substances to target cells.

Proper dose of the pharmaceutical composition for preventing or treating cancer or angiogenesis-related diseases may vary according to various factors such as method for formulating, administration method, age, weight, gender, pathological state of patient, food, administration time, administration route, excretion rate and reaction sensitivity, etc. Preferably, a proper dose of the composition is within the range of 0.001 and 100 mg/kg based on an adult. The term "pharmaceutically effective dose" as used herein refers to an amount sufficient to prevent or treat cancer or angiogenesis-related diseases.

The composition may be formulated with pharmaceutically acceptable carriers and/or excipients according to a method that can be easily carried out by those skilled in the art, and may be provided in a unit-dose form or enclosed in a multiple-dose vial. Here, the formulation of the pharmaceutical composition may be in the form of a solution, a suspension, syrup or an emulsion in oily or aqueous medium, or may be extracts, powders, granules, tablets or capsules, and may further include a dispersion agent or a stabilizer. Also, the composition may be administered individually or in combination with other therapeutic agents, and may be administered sequentially or simultaneously with conventional therapeutic agents. Meanwhile, the composition includes an antibody or an antigen-binding fragment, and thus may be formulated into immuno liposome. Liposome including an antibody may be prepared according to a method well known in the pertinent art. The immuno liposome is a lipid composition including phosphatidylcholine, cholesterol and polyethyleneglycol-derived phosphatidylethanolamine, and may be prepared by reverse phase evaporation method. For example, a Fab' fragment of antibody may be conjugated to liposome through disulphide exchange reaction. Liposome may further include chemical therapeutic agents such as Doxorubicin.

The present invention also provides a composition for diagnosis of cancer, comprising: the antibody; or a biologically active molecule fused to the antibody and selected from the group consisting of peptides, proteins, small-molecule drugs, nanoparticles and liposomes.

The term "diagnosis" as used herein refers to demonstrating the presence or characteristic of a pathophysiological condition. Diagnosing in the present invention refers to demonstrating the onset and progress of cancer.

The intact immunoglobulin-type antibody and a fragment thereof may bind to a fluorescent substance for molecular imaging in order to diagnose cancer through images.

The fluorescent substance for molecular imaging refers to all substances generating fluorescence. Preferably, red or near-infrared fluorescence is emitted, and more preferably, fluorescence with high quantum yield is emitted. However, the fluorescence is not limited thereto.

Preferably, the fluorescent substance for molecular imaging is a fluorescent substance, a fluorescent protein or other substances for imaging, which may bind to the tumor tissue-penetrating peptide that specifically binds to the intact immunoglobulin-type antibody and a fragment thereof, but is not limited thereto.

Preferably, the fluorescent substance is fluorescein, BODYPY, tetramethylrhodamine, Alexa, cyanine, allopicocyanine, or a derivative thereof, but is not limited thereto.

Preferably, the fluorescent protein is Dronpa protein, enhanced green fluorescence protein (EGFP), red fluorescent protein (DsRFP), Cy5.5, which is a cyanine fluorescent substance presenting near-infrared fluorescence, or other fluorescent proteins, but is not limited thereto.

Preferably, other substances for imaging are ferric oxide, radioactive isotope, etc., but are not limited thereto, and they may be applied to imaging equipment such as MR, PET.

The present invention also provides a polynucleotide that encodes the light-chain variable region, or an antibody comprising the same, or a fragment thereof.

The term "polynucleotide" as used herein refers to a deoxyribonucleotide or ribonucleotide polymer present in a single-stranded or double-stranded form. It includes RNA genome sequence, DNA (gDNA and cDNA), and RNA sequence transcribed therefrom. Unless otherwise described, it also includes an analog of the natural polynucleotide.

The polynucleotide includes not only a nucleotide sequence encoding the above-described light-chain region, but also a complementary sequence thereto. The complementary sequence includes a sequence fully complementary to the nucleotide sequence and a sequence substantially complementary to the nucleotide sequence. For example, this means a sequence that may be hybridized with a nucleotide sequence encoding an amino acid sequence of any one of SEQ ID NO:1 to SEQ ID NO: 3 under stringent conditions known in the pertinent art.

Also, the polynucleotide may be modified. The modification includes the addition, deletion, or non-conservative substitution or conservative substitution of nucleotides. The polynucleotide encoding the amino acid sequence is interpreted to include a nucleotide sequence that has a substantial identity to the nucleotide sequence. The substantial identity may refer to a sequence having a homology of at least 80%, a homology of at least 90%, or a homology of at least 95% when aligning the nucleotide sequence to correspond to any other sequence as much as possible and analyzing the aligned sequence using an algorithm generally used in the pertinent art.

Still another aspect of the present invention may provide a method for producing an intact immunoglobulin-type antibody, which penetrates the cytosol and binds specifically to the activated (GTP-bound) tumor-associated factor RAS in the cytosol and inhibits the activity of the RAS, using an intact immunoglobulin-type antibody that penetrates living cells and localizes in the cytosol.

In an embodiment of the present invention, an intact immunoglobulin-type antibody, which penetrates animal cells and localizes in the cytosol and binds specifically to activated (GTP-bound) RAS in the cytosol, is produced using a heavy-chain variable region (VH) having the ability to bind specifically to activated (GTP-bound) RAS, and may be produced by a method comprising the steps of:

(1) constructing a heavy-chain expression vector cloned with nucleic acids comprising a human heavy-chain variable region (VH), which binds specifically to activated (GTP-bound) RAS, and a heavy-chain constant region (CH1-hinge-CH2-CH3);

(2) co-transforming the constructed heavy-chain expression vector and a light-chain expression vector comprising a light-chain variable region having the ability to penetrate the cytosol into a protein expression animal cell, and expressing in the cell an intact immunoglobulin-type antibody that penetrates living cells and localizes in the cytosol to specifically recognize activated (GTP-bound) RAS; and (3) purifying and recovering the expressed intact immunoglobulin-type antibody that has cytosol-penetrating ability and specifically recognizes activated (GTP-bound) RAS.

The term "vector" as used herein refers to a means for expressing a target gene in a host cell. For example, the vector may include plasmid vector, cosmid vector, bacteriophage vector, and virus vectors such as adenovirus vector, retrovirus vector, and adeno-associated virus vector. The vector that may be used as the recombinant vector may be produced by operating plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), phages (for example, λgt4λB, λ-Charon, λΔz1 and M13, etc.), or virus (for example, CMV, SV40, etc.) commonly used in the pertinent art.

The light-chain variable region, the light-chain constant region (CL), the heavy-chain variable region (VH), and the heavy-chain constant region (CH1-hinge-CH2-CH3) of the present invention in the recombinant vector may be operatively linked to a promoter. The term "operatively linked" as used herein means a functional linkage between a nucleotide expression control sequence (such as a promoter sequence) and a second nucleotide sequence. Accordingly, the control sequence may control the transcription and/or translation of the second nucleotide sequence.

The recombinant vector may be generally constructed as a vector for cloning or a vector for expression. As the vector for expression, vectors generally used for expressing foreign protein from plants, animals or microorganisms in the pertinent art may be used. The recombinant vector may be constructed by various methods known in the pertinent art.

The recombinant vector may be constructed to be a vector that employs a prokaryotic cell or an eukaryotic cell as a host. For example, when the vector used is an expression vector and employs a prokaryotic cell as a host, the vector generally includes a strong promoter which may promote transcription (for example, pLλ promoter, trp promoter, lac promoter, tac promoter, T7 promoter, etc.), a ribosome binding site for initiation of translation, and termination sequences for transcription/translation. When the vector employs an eukaryotic cell as a host, a replication origin operating in the eukaryotic cell included in the vector may include an f1 replication origin, an SV40 replication origin, a pMB1 replication origin, an adeno replication origin, an AAV replication origin, a CMV replication origin and a BBV replication origin, etc., but is not limited thereto. In addition, a promoter derived from a genome of a mammal cell (for example, a metalthionine promoter) or a promoter derived from a virus of a mammal cell (for example, an adenovirus anaphase promoter, a vaccinia virus 7.5K promoter, a SV40 promoter, a cytomegalo virus (CMV) promoter, or a tk promoter of HSV) may be used, and the promoter generally has a polyadenylated sequence as a transcription termination sequence.

Another aspect of the present invention provides a host cell transformed with the recombinant vector.

Any kind of host cell known in the pertinent art may be used as a host cell. Examples of a prokaryotic cell include strains belonging to the genus *Bascillus* such as *E. coli* JM109, *E. coli* BL21, *E. coli* RR1, *E. coli* LE392, *E. coli* B, *E. coli* X 1776, *E. coli* W3110, *Bascillus subtilus* and *Bascillus thuringiensis, Salmonella typhimurium*, intestinal flora and strains such as *Serratia marcescens* and various *Pseudomonas* Spp., etc. In addition, when the vector is transformed in an eukaryotic cell, a host cell such as yeast (*Saccharomyces cerevisiae*), an insect cell, a plant cell, and an animal cell, for example, SP2/0, CHO (Chinese hamster ovary) K1, CHO DG44, PER.C6, W138, BHK, COS-7, 293, HepG2, Huh7, 3T3, RN, and MDCK cell line, etc., may be used.

A recombinant vector may be inserted into a host cell using an insertion method well known in the pertinent art. For example, when a host cell is a prokaryotic cell, the transfer may be carried out according to $CaCl_2$ method or an electroporation method, etc., and when a host cell is an eukaryotic cell, the vector may be transferred into a host cell according to a microscope injection method, calcium phosphate precipitation method, an electroporation method, a liposome-mediated transtypeion method, and a gene bombardment method, etc., but the transferring method is not limited thereto. When using microorganisms such as *E. coli*, etc. the productivity is higher than using animal cells. However, although it is not suitable for production of intact Ig form of antibodies due to glycosylation, it may be used for production of antigen binding fragments such as Fab and Fv.

The method for selecting the transformed host cell may be readily carried out according to a method well known in the pertinent art using a phenotype expressed by a selected label. For example, when the selected label is a specific antibiotic resistance gene, the transformant may be readily selected by culturing the transformant in a medium containing the antibiotic.

Advantageous Effects

According to the present invention, the method for inhibiting intracellular activated RAS using an intact immunoglobulin-type antibody having the ability to penetrate the cytosol is achieved by allowing the antibody to penetrate living cells and to specifically recognize activated (GTP-bound) RAS in the cytosol. Thus, the antibody can target activated (GTP-bound) RAS in the cytosol of living cells and inhibit the activity of the RAS.

Furthermore, the antibody light-chain variable region according to the present invention and an antibody comprising the same is able to penetrate living cells and localize in the cytosol through endocytosis and endosome escape, without having to use a special external protein delivery system. Particularly, the antibody light-chain variable region according to the present invention can easily interact with various human heavy-chain variable regions (VHs) and has the ability to penetrate the cytosol and remain in the cytosol, and an intact IgG-type monoclonal antibody comprising the light-chain variable region can penetrate cells and localize in the cytosol, and shows no cytotoxicity non-specific for target cells.

The antibody heavy-chain variable region according to the present invention and an antibody comprising the same can selectively inhibit mutations of the major drug resistance-related factor RAS of conventional various tumor therapeutic agents, and can exhibit synergistic anticancer activity with conventional therapeutic agents. In addition, the cytosol-penetrating, intact immunoglobulin-type antibody according to the present invention can penetrate cells and remain in the cytosol, without affecting the high specificity and affinity of a human antibody heavy-chain variable region (VH) for antigens, and thus can localize in the cytosol which is currently classified as a target in disease treatment based on small-molecule drugs, and at the same time, can exhibit high effects on the treatment and diagnosis of tumor and disease-related factors that show structurally complex interactions through a wide and flat surface between protein and protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A shows the results of analysis of a sequence including a clone used in a process of obtaining the improved, cytosol-penetrating humanized light-chain variable single domain hT3 VL, which binds stably to a humanized antibody heavy-chain variable region, from the mouse light-chain variable region m3D8 VL.

FIG. 5B compares model structures using the WAM modeling of m3D8 VL, the humanized light-chain variable single domain hT0 VL and its mutants (hT2 VL and hT3 VL) by a superimposing method.

FIG. 22 shows the results of FACS analysis performed to determine binding to GTP-bound KRas G12D and GDP-bound KRas G12D for library-expressing yeast in each step in order to confirm enrichment specific for GTP-bound KRas G12D in the above-described library screening process.

FIG. 23 shows the results of sequencing of individual clones using three libraries.

BEST MODE FOR CARRYING OUT THE INVENTION

Hereinafter, the present invention will be described in further detail with reference to examples. It will be obvious to a person having ordinary skill in the art that these examples are illustrative purposes only and are not to be construed to limit the scope of the present invention.

Figure 1:
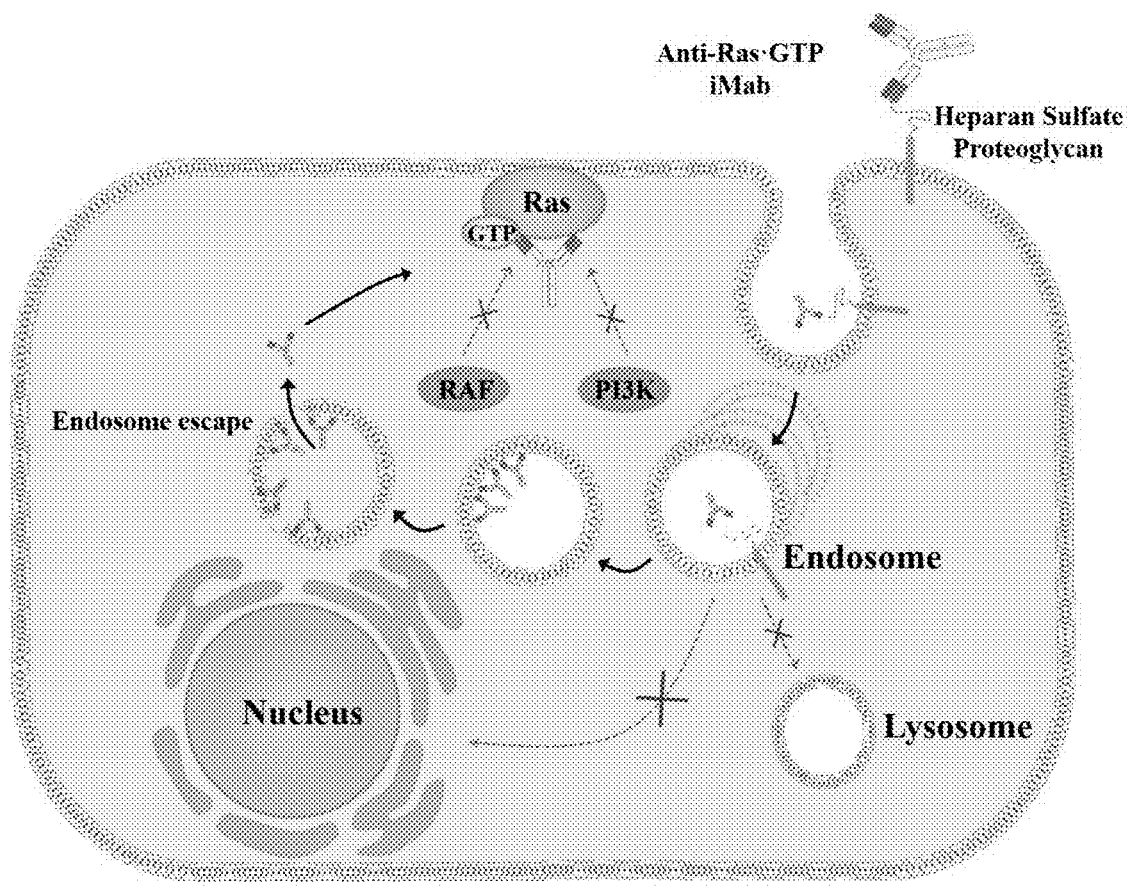
FIG. 1 is a schematic view showing a strategy of inducing cytotoxicity specific for Ras mutant cells by use of a monoclonal antibody (anti-Ras. GTP iMab: internalizing & interfering monoclonal antibody) which is constructed by replacing the heavy-chain variable region (VH) of the immunoglobulin-type antibody cytotransmab (having only cytosol-penetrating ability) with a heavy-chain variable region (VH) binding specifically to GTP-bound KRas and which penetrates cells and binds specifically to GTP-bound Ras in the cytosol.

Example 1: Selection of Heavy-Chain Variable Region (VH), which Binds Specifically to GTP-Bound KRas, by High-Diversity Human VH Library FIG. 1 is a schematic view showing a strategy of inducing cytotoxicity specific for Ras mutant cells by use of a monoclonal antibody (anti-Ras.GTP iMab: internalizing & interfering monoclonal antibody) which is constructed by replacing the heavy-chain variable region (VH) of an IgG-type cytotransmab (having only cytosol-penetrating ability) with a heavy-chain variable region (VH) binding specifically to GTP-bound KRas and which penetrates cells and binds specifically to GTP-bound Ras in the cytosol.

Figure 2:
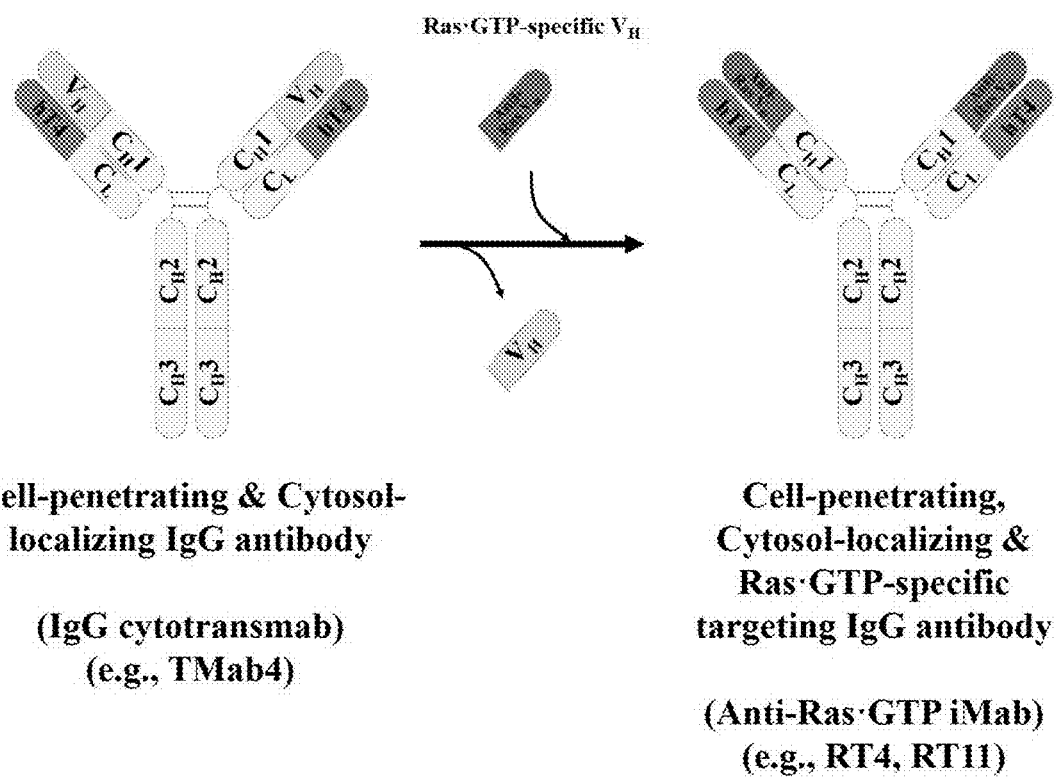
FIG. 2 is a schematic view showing a method of constructing anti-Ras•GTP iMab by replacing the heavy-chain variable region (VH) of cytotransmab, which has only cytosol-penetrating ability, with a heavy-chain variable region (VH) which binds specifically to GTP-bound KRas.

FIG. 2 is a schematic view showing a method of constructing anti-Ras•GTP iMab by replacing the heavy-chain variable region (VH) of an intact IgG-type cytotransmab, which has only cytosol-penetrating ability, with a heavy-chain variable region (VH) which binds specifically to GTP-bound KRas.

Specifically, the FR (framework) of the library used was the V gene IGHV3-23*04, $J_H4$ which is most commonly used in conventional antibodies, and the CDR3 in the library had 9 residues. The construction of the library and a yeast surface display method are described in detailed in a previously reported paper (Baek and Kim, 2014).

In order to select a stable humanized heavy-chain variable single domain (VH) antibody fragment which is to be introduced into the anti-Ras•GTP iMab and which binds specifically to GTP-bound KRas, a yeast display VH library constructed in a previous studies was used.

Example 2: Preparation of GTP-Bound KRas G12D Protein

Expression in *E. coli* and purification, performed to prepare GTP-bound KRas G12D antigen for library screening and affinity analysis, are described in detail in a previously reported paper (Tanaka T et al., 2007).

Specifically, a DNA encoding residues 1 to 188, which comprises the CAAX motif of each of wild-type KRas and mutant KRas G12D, KRas G12V and KRas G13D (listed in the order of higher to lower mutation frequency), was cloned into the *E. coli* expression vector pGEX-3X by use of the restriction enzymes BamHI/EcoRI. Herein, the expression vector was designed to have a T7 promoter-GST-KRas. All KRas mutations were induced using an overlap PCR technique, and the expression vector was constructed using the above-described method. The pGEX-3X-KRas vector was transformed into *E. coli* by electroporation, and selected in a selection medium. The selected *E. coli* was cultured in LB medium in the presence of 100 μg/ml of an ampicillin antibiotic at 37° C. until the absorbance at 600 nm reached 0.6. Then, 0.1 mM IPTG was added thereto for protein expression, and then the *E. coli* cells were further cultured at 30° C. for 5 hours. Thereafter, the *E. coli* cells were collected by centrifugation, and then disrupted by sonication (SONICS). The disrupted *E. coli* cells were removed by centrifugation, and the remaining supernatant was collected and purified using glutathione resin (Clontech) that specifically purifies GST-tagged protein. The glutathione resin was washed with 50 ml of washing buffer (140 mM NaCl, 2.7 mM KCl, 10 mM $NaH_2PO_4$, 1.8 mM $KH_2PO_4$, 1 mM EDTA, 2 mM $MgCl_2$ pH 7.4) (SIGMA), and then protein was eluted with elution buffer (50 mM Tris-HCl pH8.0, 10 mM reduced glutathione, 1 mM DTT, 2 mM $MgCl_2$) (SIGMA). The eluted protein was dialyzed to replace the buffer with storage buffer (50 mM Tris-HCl pH8.0, 1 mM DTT, 2 mM $MgCl_2$) (SIGMA). The purified protein was quantified by measuring the absorbance at a wavelength of 280 nm and the absorption coefficient. SDS-PAGE analysis indicated that the protein had a purity of about 98% or higher.

Next, in order to bind a GTPλS (Millipore) or GDP (Millipore) substrate to KRas protein, KRas and a substrate at a molecular ratio of 1:20 were reacted in a reaction buffer (50 mM Tris-HCl pH8.0, 1 mM DTT, 5 mM $MgCl_2$, 15 mM EDTA) (SIGMA) at 30° C. for 30 minutes, and 60 mM $MgCl_2$ was added thereto to stop the reaction, and then stored at −80° C.

Figure 15:
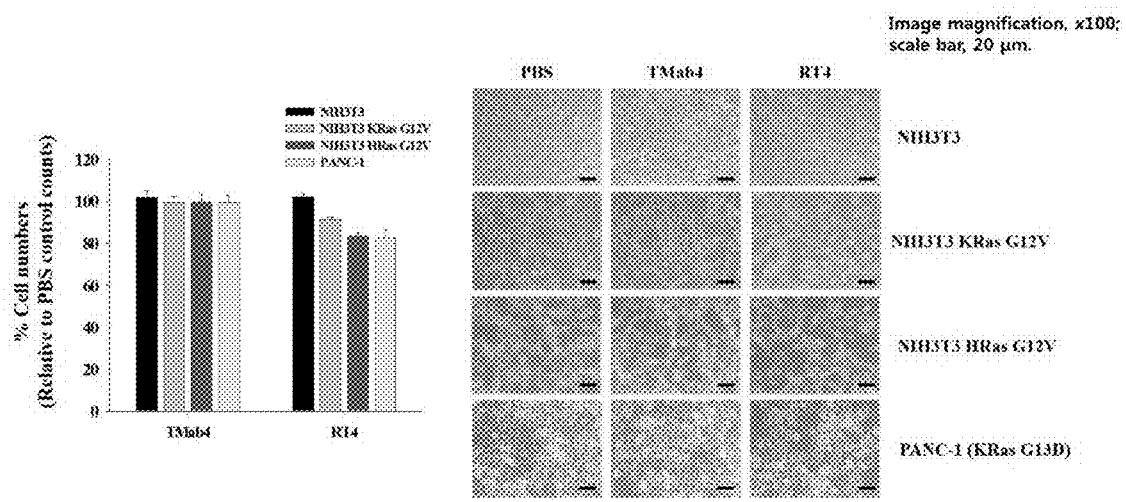
FIG. 15 shows the results obtained by treating NIH3T3, NIH3T3 KRas G12V and NIH3T3 HRas G12V cell lines with anti-Ras•GTP iMab RT4 and evaluating in vitro the inhibition of growth of the cells.

Example 3: Selection of Heavy-Chain Variable Region (VH) Specific for GTP-Bound KRas G12D FIG. 15 is a schematic view showing a library screening strategy for obtaining a humanized antibody heavy-chain variable single domain having a high affinity only for GTP-bound KRas G12D protein.

Specifically, GTP-bound KRas G12D purified in Example 14 was biotinylated (EZ-LINK™ Sulfo-NHS-LC-Biotinylation kit (Pierce Inc., USA)), and then reacted with a heavy-chain variable region library displayed on the yeast cell surface at room temperature for 1 hour. The heavy-chain variable region library on the yeast cell surface, which reacted with the biotinylated GTP-bound KRas G12D, was reacted with Streptavidin (Microbead™ (Miltenyi Biotec) at 4° C. for 20 minutes, and then yeast displaying a heavy-chain variable region having a high affinity for the GTP-KRAS G12D was enriched using MACS (magnetic activated cell sorting). The selected library-displaying yeast was cultured in a selection medium and cultured in SG-CAA+ URA (20 g/L Galactose, 6.7 g/L Yeast nitrogen base without amino acids, 5.4 g/L Na2HPO4, 8.6 g/L $NaH_2PO_4$, 5 g/L casamino acids, 0.2 mg/L Uracil) (SIGMA) medium to induce protein expression. Next, the yeast was incubated with a yeast displaying the library competitively with GTP-bound KRas G12D alone or non-biotinylated GTP-bound KRas G12D antigen at a concentration 10-fold higher than GTP-bound KRas G12D, at room temperature for 1 hour, after which it was reacted with PE-conjugated Streptavidin (Streptavidin-R-phycoerythrin conjugate (SA-PE) (Invitrogen), and enriched by FACS (fluorescence activated cell sorting) (FACS Caliber) (BD biosciences). After selection of screening conditions by FACS analysis, antigen was bound to the yeast displaying the enriched library under the same conditions as described, and then the yeast was enriched using a FACS aria II sorter. The humanized heavy-chain region library enriched by the first MACS and first FACS screening was mated with a yeast secreting the cytosol-penetrating light-chain variable single domain (hT4 VL), and displayed on the yeast surface in the form of Fab, and then subjected to second FACS and third FACS screening.

Specifically, in order to construct a yeast which is to be mated with the heavy-chain variable domain (VH) library and which secretes the cytosol-penetrating light-chain variable domain (VL), a DNA encoding the cytosol-penetrating hT4 VL was cloned into the light-chain variable domain yeast secretion vector pYDS-K by the restriction enzymes NheI and BsiWI, thereby obtaining pYDS-K-hT4 VL. The obtained pYDS-K-hT4 VL was transformed into the mating α-type yeast mating strain YVH10 by electroporation, and mated with a yeast cultured in the selection medium SD-CAA+Trp (20 g/L Glucose, 6.7 g/L Yeast nitrogen base without amino acids, 5.4 g/L Na2HPO$_4$, 8.6 g/L NaH$_2$PO$_4$, 5 g/L casamino acids, 0.4 mg/L tryptophan) (SIGMA).

Specifically, in the case of yeast mating, there are $1\times10^7$ yeast cells when the absorbance at 600 nm is 1. Among the cultured yeast cells, $1.5\times10^7$ yeast cells expressing the selected heavy-chain variable domain library and $1.5\times10^7$ yeast cells containing hT4 VL were added to GTP-bound KRas G12D, and washed three times with YPD YPD (20 g/L Dextrose, 20 g/L peptone, 10 g/L yeast extract, 14.7 g/L sodium citrate, 4.29 g/L citric acid, pH 4.5) (SIGMA). Then, the yeast cells were re-suspended in 100 µl of YPD, and dropped onto an YPD plate so as not to spread, after which these yeast cells were dried and cultured at 30° C. for 6 hours. Next, the dried yeast-coated portion was washed three times with YPD medium, and then incubated in the selection medium SD-CAA at 30° C. for 24 hours to a final yeast concentration of $1\times10^6$ cells or less, and only mated yeast cells were selected. The selected yeast cells were incubated in SG-CAA medium to induce expression of a humanized antibody Fab fragment, and enriched by second and third FACS such that the yeast cells would be 100-fold competitive with GDP-bound KRas G12D at a GTP-bound KRas G12D concentration of 100 nM.

Figure 16:
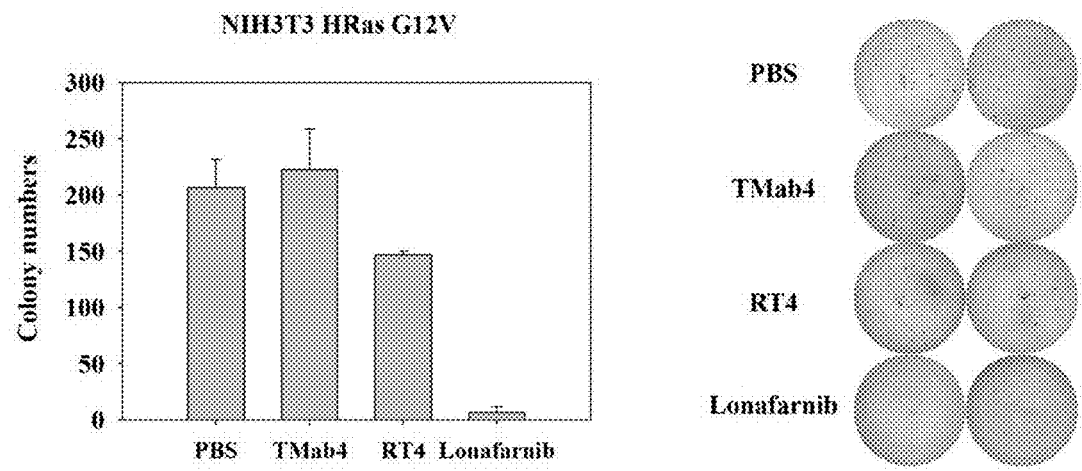
FIG. 16 shows the results of evaluating the inhibition of growth of non-adherent cells in an NIH3T3 HRas G12V cell line.

FIG. 16 shows the results of FACS analysis of binding under a condition of GTP-bound KRas G12D alone and a condition competitive with GTP-bound KRas G12D in each step of the above-described screening process for obtaining a high affinity for GTP-bound KRas G12D. Accordingly, it was found that it is possible to select a library that can bind specifically to GTP-bound KRas G12D in a manner dependent on the heavy-chain variable domain (VH).

Through the high-throughput screening as described above, an RT4 clone was finally selected from the library having a high affinity and specificity for GTP-bound KRas G12D protein by individual clone analysis.

Example 4: Rationale for Development of Cytosol-Penetrating Humanized Light-Chain Variable (VL) Single Domain FIGS. 5A and 5B are schematic views showing the concept of an intact immunoglobulin antibody, named "cytotransmab", which penetrates a cell and localizes in the cytosol. To realize this antibody and understand the cytosol-penetrating ability of humanized antibody light-chain variable regions, reference was made to conventional studies on the correlations between the cytosol-penetrating ability of the mouse light-chain variable single domain m3D8 VL and CDRs corresponding to light-chain variable region fragments (Lee et al., 2013).

FIG. 5A shows the results of analysis of a sequence including a clone used in a process of obtaining the improved, cytosol-penetrating humanized light-chain variable single domain hT3 VL, which binds stably to a humanized antibody heavy-chain variable region, from the mouse light-chain variable region m3D8 VL.

Specifically, based on a comparison of cytosol-penetrating ability between the mouse light-chain variable single domain m3D8 VL and hT0 VL obtained by humanizing the single domain m3D8 VL by use of CDR-grafting technology, it was confirmed that the cytosol-penetrating ability was lost even though the CDR1 sequence of the light-variable variable region (VL) was conserved.

Thus, in order to improve the structure of CDR1 to have a structure similar to that of m3D8 VL to thereby restore the cytosol-penetrating ability of the humanized antibody light-chain variable single domain, CDR regions (Vernier zones) in the FR (framework) were comparatively analyzed. As a result, it was found that residues 2 and 4 differ from those of mouse m3D8 VL having cytosol-penetrating ability. Particularly, because residues 2 and 4 act as an upper core that greatly influence the CDR1 structure (Vernizer zone), hT2 VL having a CDR1 structure similar to that of m3D8 VL was developed by reverse mutations of hT0 VL (see FIG. 5A).

Next, in order to construct stable cytotransmab and to create a pair between VH3 and Via subgroups (that are highly prevalent in stable antibodies) to thereby develop a light-chain variable region that complementarily stably binds to a variety of human antibody heavy-chain variable regions and retains its ability to penetrate into the cytosol, the FR (framework) of hT2 VL and the light-variable region FR (framework) of the humanized therapeutic monoclonal antibody Trastuzumab (Herceptin), which has VH3 and Vκ1 subgroups and is very stable, were comparatively analyzed. As a result, it was shown that 14 residues in the FR (framework) of hT2 VL differ from those in the light chain-variable region FR (framework) of Trastuzumab. These 14 residues were mutated with the sequence of the light chain-variable region FR (framework) of Trastuzumab, thereby developing hT3 VL (see FIG. 5A).

FIG. 5B compares model structures using the WAM modeling of m3D8 VL, the humanized light-chain variable single domain hT0 VL and its mutants (hT2 VL and hT3 VL) by a superimposing method. It was found that, through reverse mutations at residues 2 and 4 as described above, the structural difference of the CDR1 region from that of m3D8 VL was reduced.

Example 5: Expression and Purification of Humanized Light-Chain Variable (VL) Single Domain Having Cytosol-Penetrating Ability To compare the actual cytosol-penetrating abilities of hT2 VL and hT3 VL designed in the above Example 4, humanized light-chain variable (VL) single domains were purified.

Specifically, the cytosol-penetrating light-chain variable single domain containing a Pho A signal peptide at the N-terminus and a protein A tag at the C-terminus was cloned into a pIg20 vector by NheI/BamHI restriction enzymes, and then the vector was transformed into E. coli BL21(DE3)

plysE for protein expression by electroporation. The *E. coli* was cultured in LBA medium containing 100 ug/ml of ampicillin at 180 rpm and 37° C. until the absorbance at 600 nm reached 0.6-0.8. Then, the culture was treated with 0.5 mM of IPTG (isopropyl β-D-1-thiogalactopyronoside, and then incubated at 23° for 20 hours to express the protein. After expression, the culture was centrifuged by a high-speed centrifuge at 8,000 rpm for 30 minutes, and the supernatant was collected, and then reacted with IgG-Sepharose resin (GE Healthcare). The resin was washed with 50 ml of TBS (Tris-HCl, 137 mM NaCl, 2.7 mM KCl, pH 7.4), and then washed with 5 ml of 5 mM NH$_4$Ac (pH 5.0) buffer. Next, the protein was eluted from the resin by use of 0.1 M HAc (pH 3.0) buffer, and the buffer was replaced with TBS (pH 7.4) by dialysis. Then, the concentration of the protein was measured by a BCA (bicinchoninic acid (Pierce)) assay, and the purity of the protein was analyzed by SDS-PAGE.

Example 6: Verification of Cytosol-Penetrating Ability and Cell Penetration Mechanism of Cytosol-Penetrating Humanized Light-Chain Variable (VL) Single Domain FIG. 6A shows the results of confocal microscopy observation of the cytosol-penetrating ability of light-chain variable single domains.

Specifically, in order to verify the cytosol-penetrating abilities of m3D8 VL, hT0 VL, hT2 VL and hT3 VL, a cover slip was added to 24-well plates, and 5×10$^4$ HeLa cells per well were added to 0.5 ml of 10% FBS (Fetal bovine Serum)-containing medium and cultured for 12 hours under the conditions of 5% CO$_2$ and 37° C. When the cells were stabilized, each well was treated with 10 μM of m3D8 VL, hT0 VL, hT2 VL or hT3 VL in 0.5 ml of fresh medium, and incubated for 6 hours under the conditions of 37° C. and 5% CO$_2$. Next, the medium was removed, and each well was washed with PBS, and then treated with a weakly acidic solution (200 mM glycine, 150 mM NaCl, pH 2.5) to remove proteins from the cell surface. Next, each well was washed with PBS, and the cells were fixed in 4% paraformaldehyde at 25° C. for 10 minutes. After washing with PBS, each well was incubated with PBS buffer containing 0.1% saponin, 0.1% sodium azide and 1% BSA at 25° C. for 10 minutes to form pores in the cell membranes. After washing with PBS, each well was incubated with PBS buffer c containing 2% BSA at 25° C. for 1 hour to eliminate nonspecific binding. Then, each well was treated with rabbit-IgG (Sigma) that recognizes the protein A tag of the light-chain variable single domain, and each well was incubated at 25° C. for 2 hours, washed three times with PBS, and then treated with red fluorescence (TRITC)-labeled anti-rabbit antibody (Sigma), followed by incubation at 25° C. for 1 hour. Finally, the nucleus was blue-stained with Hoechst33342 and observed with a confocal microscope. As a result, it was shown that m3D8 VL, hT2 VL and hT3 VL, except for hT0 VL, had cell-penetrating ability.

Figure 6A:
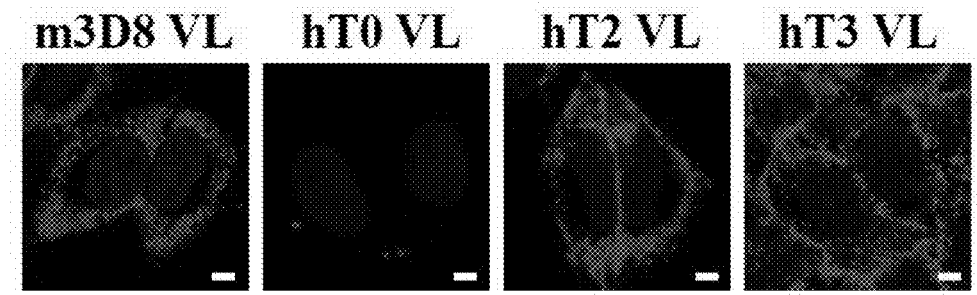
FIG. 6A shows the results of confocal microscopy observation of the cytosol-penetrating ability of light-chain variable single domains.
Figure 6B:
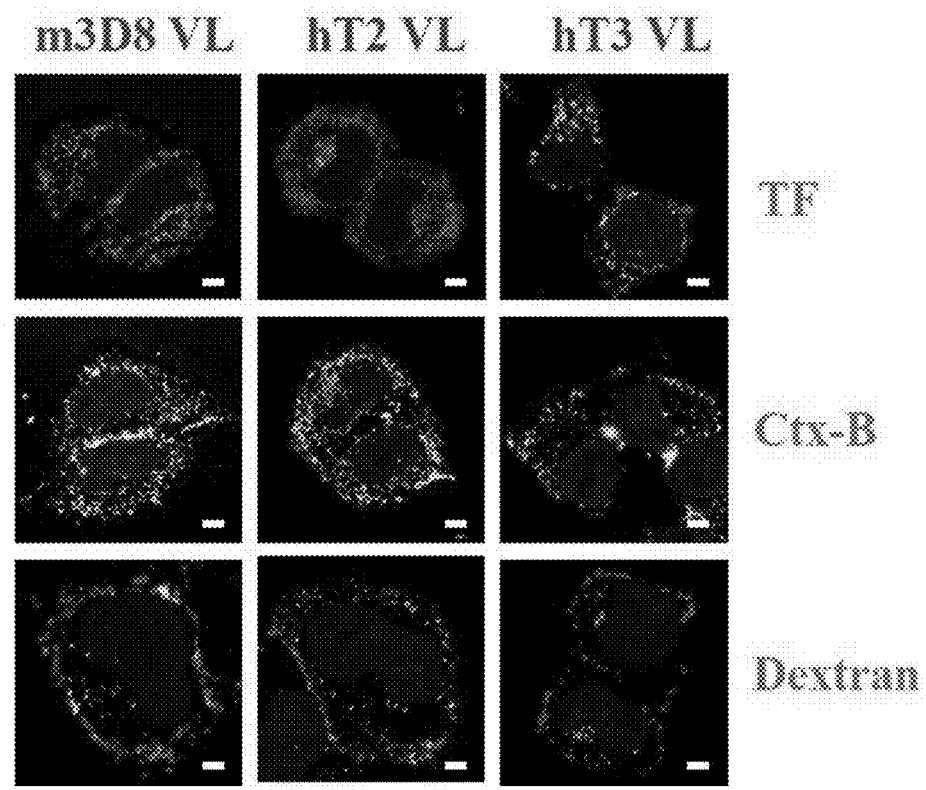
FIG. 6B shows the results of confocal microscopy observation performed to verify the cytosol-penetrating mechanisms of light-chain variable single domains.

FIG. 6B shows the results of confocal microscopy observation performed to verify the cytosol-penetrating mechanisms of light-chain variable single domains.

Figure 3:
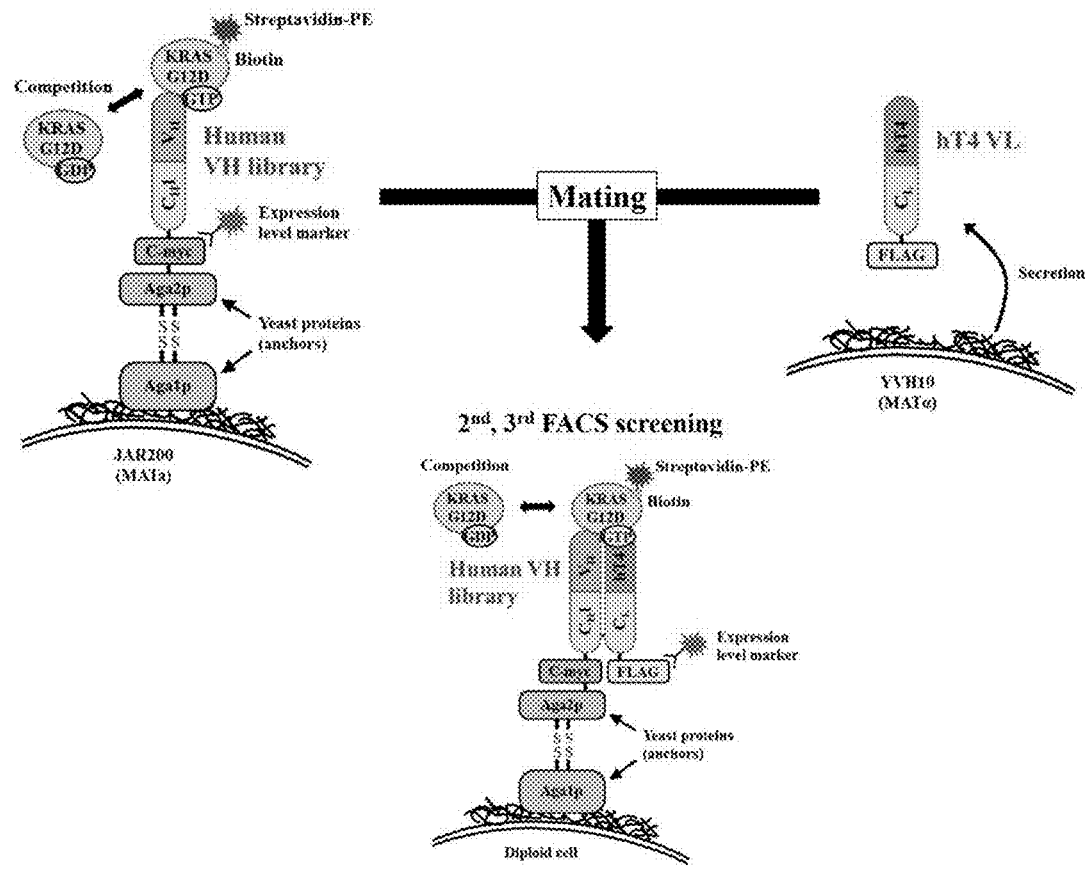
FIG. 3 is a schematic view showing a library screening strategy for obtaining a humanized antibody heavy-chain variable single domain having high affinity only for GTP-bound KRas G12D protein.
Figure 4:
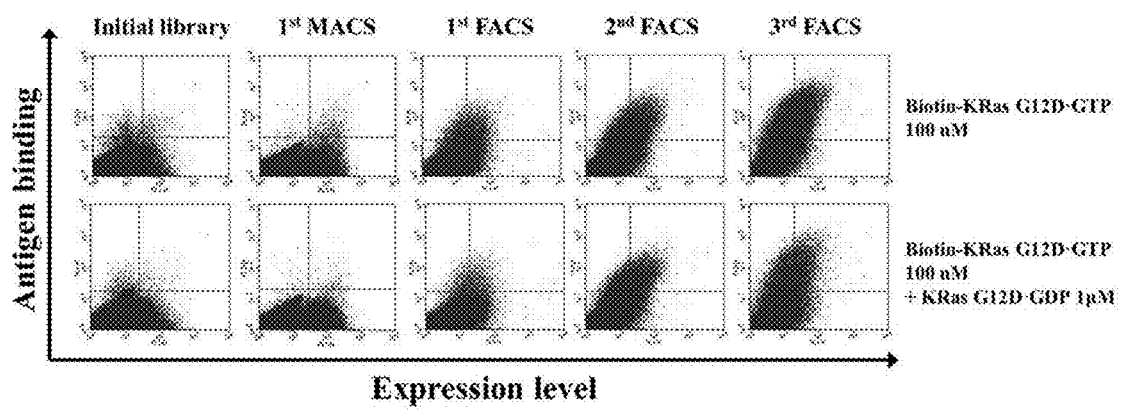
FIG. 4 shows the results of FACS analysis of binding, performed under a condition of GTP-bound KRas G12D alone and a condition competitive with GTP-bound KRas G12D in each step of the above-described process for obtaining a high affinity for GTP-bound KRas G12D.

Specifically, when HeLa cells were prepared as shown in FIG. 6A and stabilized, a dilution of 10 μM of m3D8 VL, hT2 VL or hT3 VL and 10 ug/ml of Alexa Fluor 488-transferrin (TF, green fluorescence), FITC-cholera toxin B (Ctx-B, green fluorescence) or Oregon green-dextran (Dextran, green fluorescence) in 0.5 ml of fresh medium was added to each well and incubated for 2 hours under the conditions of 37° C. and 5% CO$_2$. Next, the light-chain variable single domains were stained as shown in FIG. 3A. As shown in FIG. 3B, all the light-chain variable single domains were superimposed with cholera toxin-B, indicating that these domains penetrate the cytosol by caveolae.

Example 7: Development of Cytosol-Penetrating Humanized Light-Chain Variable (VL) Single Domain that Easily Interacts with Human Antibody Heavy-Chain Variable Domain FIG. 7A shows the results of analyzing the amino acid sequence of hT3 VL together with the amino acid sequences of light-chain variable domains (VLs) of conventional human antibody Adalimumab (Humira) and humanized antibody Bevacizumab (Avastin) in order to confirm whether or not hT3 VL can be applied to a variety of human antibody heavy-chain variable domains.

Specifically, VH-VL interface residues that are involved in the interaction between heavy-chain and light-chain variable domains were analyzed. As a result, it was found that lysine (K) at position 89 and serine (S) at position 91 of the CDR3 of the VL domain are consistent with glutamine (Q) at position 89 and tyrosine (Y) in human antibodies.

To construct a strategy for improving the residues, the effects of VH-VL interface residues on the CDRs of the heavy-chain variable domain and the light-chain variable region were analyzed in more detail.

Figures 7A, 7B:
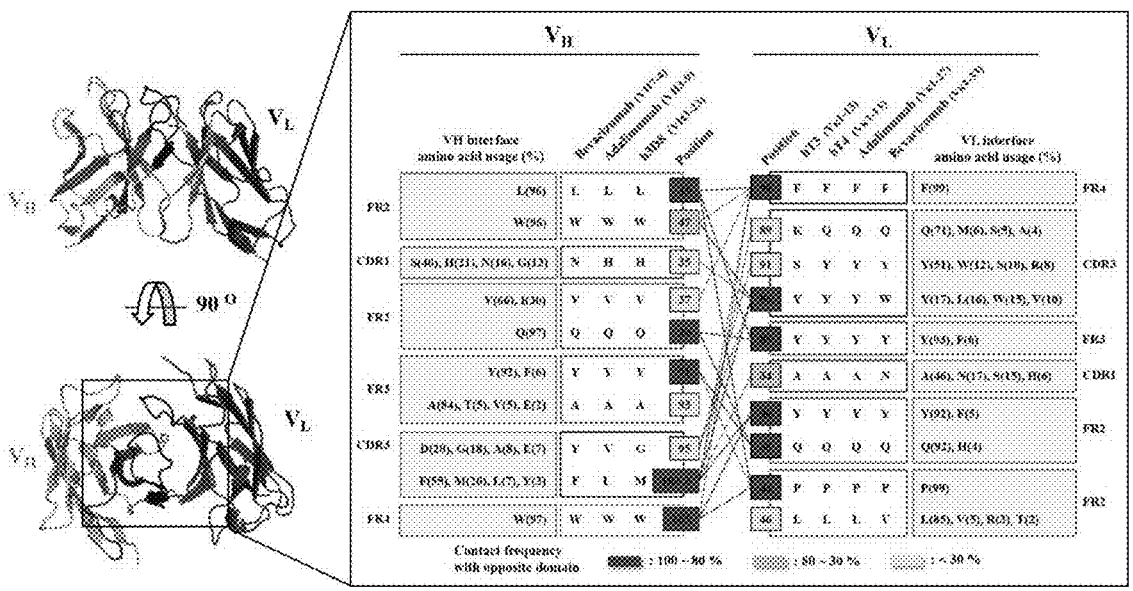
FIG. 7A shows the results of analyzing the amino acid sequence of hT3 VL together with the amino acid sequences of light-chain variable regions (VLs) of conventional human antibody Adalimumab (Humira) and humanized antibody Bevacizumab (Avastin) in order to confirm whether or not hT3 VL can be applied to a variety of human antibody heavy-chain variable regions.
FIG. 7B shows the results of analyzing interface residues between variable regions in order to construct stable cytotransmab that optimally interacts with a human antibody heavy-chain variable region.

FIG. 7B shows the results of analyzing interface residues between variable regions in order to construct stable cytotransmab that optimally interacts with a human antibody heavy-chain variable region.

Specifically, based on Information about the positions of interface residues between human antibody variable regions, the frequency of binding to specific interface residues located in opposite variable regions, and the abundance of interface residues in human antibodies, which were reported in the literature, hT3 VL and the interface residues between the heavy chain and light chain variable regions of Bevacizumab (Avastin) and Adalimumab (Humira), which are antibodies approved by the FDA, were analyzed (Vargas-Madrazo and Paz-Garcia, 2003). The results of the analysis indicated that, in the mouse CDRs of hT3 VL, residues 89 and 91 in CDR3 that is involved in association between variable regions are highly abundant in human antibodies and can influence the CDR3 structure of the heavy-chain variable region (VH). The two residues were mutated with amino acids that are highly abundant in human antibodies, thereby hT4 VL that can optimally bind to human antibody heavy-chain variable regions.

Tables 1 and 2 below show the sequences of the designed human antibody light-chain variable regions having cytosol-penetrating ability. Table 1 shows the full-length sequences of the human antibody light-chain variable regions, numbered according to the Kabat numbering system, and Table 2 shows the CDR sequences of the antibody sequences shown in Table 1.

TABLE 1

Full-length sequences of cytosol-penetrating
human antibody light-chain variable regions

| Names of light-chain variable regions | Sequence | SEQ ID NO: |
|---|---|---|
| hT2 VL | 1       10       20    abc<br>DLVMTQSPATLSLSPGERATLSCKSSQSLF<br>def  30      40      50<br>NSRTRKNYLAWYQQKPGQAPRLLIYWASTR<br>    60      70      80<br>ESGIPDRFSGSGSGTDFTLTISSLEPEDFA<br>    90     100<br>VYYCKQSYYHMYTFGQGTKVEIKR | 29 |
| hT3 VL | 1       10       20    abc<br>DLVMTQSPSSLSASVGDRVTITCKSSQSLF<br>def  30      40      50<br>NSRTRKNYLAWYQQKPGKAPKLLIYWASTR<br>    60      70      80<br>ESGVPSRFSGSGSGTDFTLTISSLQPEDFA<br>    90     100<br>TYYCKQSYYHMYTFGQGTKVEIKR | 30 |
| hT4 VL | 1       10       20    abc<br>DLVMTQSPSSLSASVGDRVTITCKSSQSLF<br>def  30      40      50<br>NSRTRKNYLAWYQQKPGKAPKLLIYWASTR<br>    60      70      80<br>ESGVPSRFSGSGSGTDFTLTISSLQPEDFA<br>    90     100<br>TYYCQQYYYHMYTFGQGTKVEIKR | 31 | ing ability with a humanized light-chain variable region having cytosol-penetrating ability in order to construct cytotransmab.

Specifically, in order to construct a heavy-chain expression vector for producing an intact immunoglobulin-type monoclonal antibody, a DNA encoding a heavy chain comprising an antibody heavy-chain variable region (Bevacizumab VH, Adalimumab VH, or humanized hT0 VH) and a heavy-chain constant region (CH1-hinge-CH2-CH3), which has a secretion signal peptide-encoding DNA fused to the 5' end, was cloned into a pcDNA3.4 vector (Invitrogen) by NotI/HindIII. Furthermore, in order to construct a vector that expresses a light chain, a DNA encoding either a cytosol-penetrating light-chain variable region (hT4 VL) or the light-chain variable region (Bevacizumab VL, or Adalimumab VL) and light-chain constant region (CL) of a model antibody, which a secretion signal peptide-encoding DNA fused to the 5' end, was cloned into a pcDNA3.4 vector (Invitrogen) by use of NotI/HindIII.

The light-chain and heavy-chain expression vectors were transiently transfected, and the proteins were expressed and purified, followed by comparison of the yield of the proteins. In a shaking flask, HEK293-F cells (Invitrogen) suspension-growing in serum-free FreeStyle 293 expression medium (Invitrogen) were transfected with a mixture of plasmid and polyethylenimine (PEI) (Polyscience). After 200 mL transfection in a shaking flask (Corning), HEK293-F cells were seeded into 100 ml of medium at a density of $2.0 \times 10^6$ cells/ml, and cultured at 150 rpm and in 8% $CO_2$. To produce each monoclonal antibody, a suitable heavy-chain and light-

TABLE 2

CDR sequences of cytosol-penetrating human antibody light-chain variable regions.

| Names of light-chain variable regions | CDR1 Sequence | | | | | | | | | | | | | | | | SEQ ID NO: | CDR2 Sequence | | | | | | | SEQ ID NO: |
|---|---|---|---|---|---|---|---|---|---|---|---|---|---|---|---|---|---|---|---|---|---|---|---|---|---|
| Kabat No. | 24 | 25 | 26 | 27 | 27a | 27b | 27c | 27d | 27e | 27f | 28 | 29 | 30 | 31 | 32 | 33 | 34 | 50 | 51 | 52 | 53 | 54 | 55 | 56 | |
| hT2 VL | K | S | S | Q | S | L | F | N | S | R | T | R | K | N | Y | L | A | 32 | W | A | S | T | R | E | S | 33 |
| hT3 VL | K | S | S | Q | S | L | F | N | S | R | T | R | K | N | Y | L | A | 35 | W | A | S | T | R | E | S | 36 |
| hT4 VL | K | S | S | Q | S | L | F | N | S | R | T | R | K | N | Y | L | A | 38 | W | A | S | T | R | E | S | 39 |

| Names of light-chain variable regions | CDR3 Sequence | | | | | | | | | SEQ ID NO: |
|---|---|---|---|---|---|---|---|---|---|---|
| Kabat No. | 89 | 90 | 91 | 92 | 93 | 94 | 95 | 96 | 97 | |
| hT2 VL | K | Q | S | Y | Y | H | M | Y | T | 34 |
| hT3 VL | K | Q | S | Y | Y | H | M | Y | T | 37 |
| hT4 VL | Q | Q | Y | Y | Y | H | M | Y | T | 40 |

Figure 8:
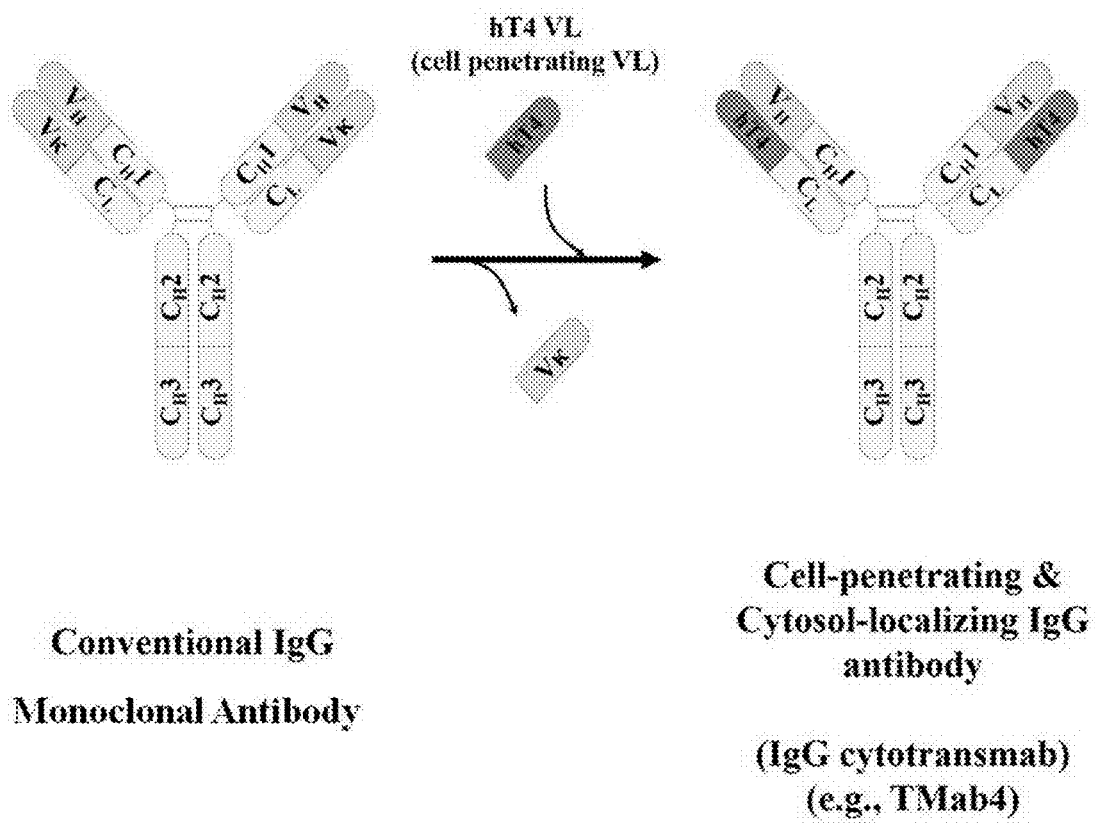
FIG. 8 is a schematic view showing a method of replacing a light-chain variable region having no cell-penetrating ability with a humanized light-chain variable region having cytosol-penetrating ability in order to construct cytotransmab.

Example 8: Development of Cytotransmab by Substitution with Cytosol-Penetrating Humanized Light-Chain Region (VL), and Expression and Purification of Cytotransmab FIG. 8 is a schematic view showing a method of substituting a light-chain variable region having no cell-penetratchain plasmid were diluted in 10 ml of FreeStyle 293 expression medium (Invitrogen) (125 μg heavy chain, 125 μg light chain, a total of 250 μg (2.5 μg/ml)), and the dilution was mixed with 10 ml of medium containing 750 μg (7.5 μg/ml) of PEI, and the mixture was incubated at room temperature for 10 minutes. The incubate medium mixture was added to 100 ml of the seeded cell culture which was then cultured at 150 rpm in 8% $CO_2$ for 4 hours, after which 100 ml of FreeStyle 293 expression was added to the cell culture, followed by culture for 6 days. In accordance with the standard protocol, the protein was purified from the collected cell culture supernatant. The antibody was applied to a Protein A Sepharose column (GE Healthcare), and washed with PBS (pH 7.4). The antibody was eluted using 0.1 M glycine buffer (pH 3.0), and then immediately neutralized with 1M Tris buffer. The eluted antibody fraction was concentrated while the buffer was replaced with PBS (pH 7.4) by dialysis. The purified protein was quantified by measuring the absorbance at 280 nm and the absorption coefficient.

Table 3 below shows the yields of purified cytotransmabs and proteins produced per liter of culture volume. Three measurements were statistically processed, and ± indicates standard deviation values. With respect to the yields of the obtained proteins, cytotransmabs, including hT4 VL improved to facilitate its interaction with a human heavy-chain variable region (VH), did not greatly differ from the wild-type monoclonal antibodies.

TABLE 3

Comparison of the purification yields of Cytotransmabs with those of wild-type IgG-type monoclonal antibodies (Adalimumab, and Bevacizumab)

| IgG clone | VH | VL | IgG purification yield (mg/1-liter of transfected cells) |
|---|---|---|---|
| TMab2 | h3D8 VH | hT2 VL | 8.0 ± 0.7 |
| TMab3 | h3D8 VH | hT3 VL | 8.2 ± 0.5 |
| TMab4 | h3D8 VH | hT4 VL | 10.8 ± 1.0 |
| Adalimumab | Adalimumab VH | Adalimumab VL | 11.6 ± 0.3 |
| HuT2 | Adalimumab VH | hT2 VL | 2.1 ± 0.6 |
| HuT3 | Adalimumab VH | hT3 VL | 3.5 ± 0.8 |
| HuT4 | Adalimumab VH | hT4 VL | 10.9 ± 0.8 |
| Bevacizumab | Bevacizumab VH | Bevacizumab VL | 8.8 ± 0.4 |
| AvaT4 | Bevacizumab VH | hT4 VL | 8.0 ± 1.1 |

These results indicate that the humanized light-chain variable region (hT4 VL) obtained by additionally modifying interface residues can optimally interact with a humanized antibody heavy-chain variable region, and thus can be stably expressed and purified.

Example 9: Verification of Cytosol-Penetrating Abilities of Cytotransmab

Figure 9A:
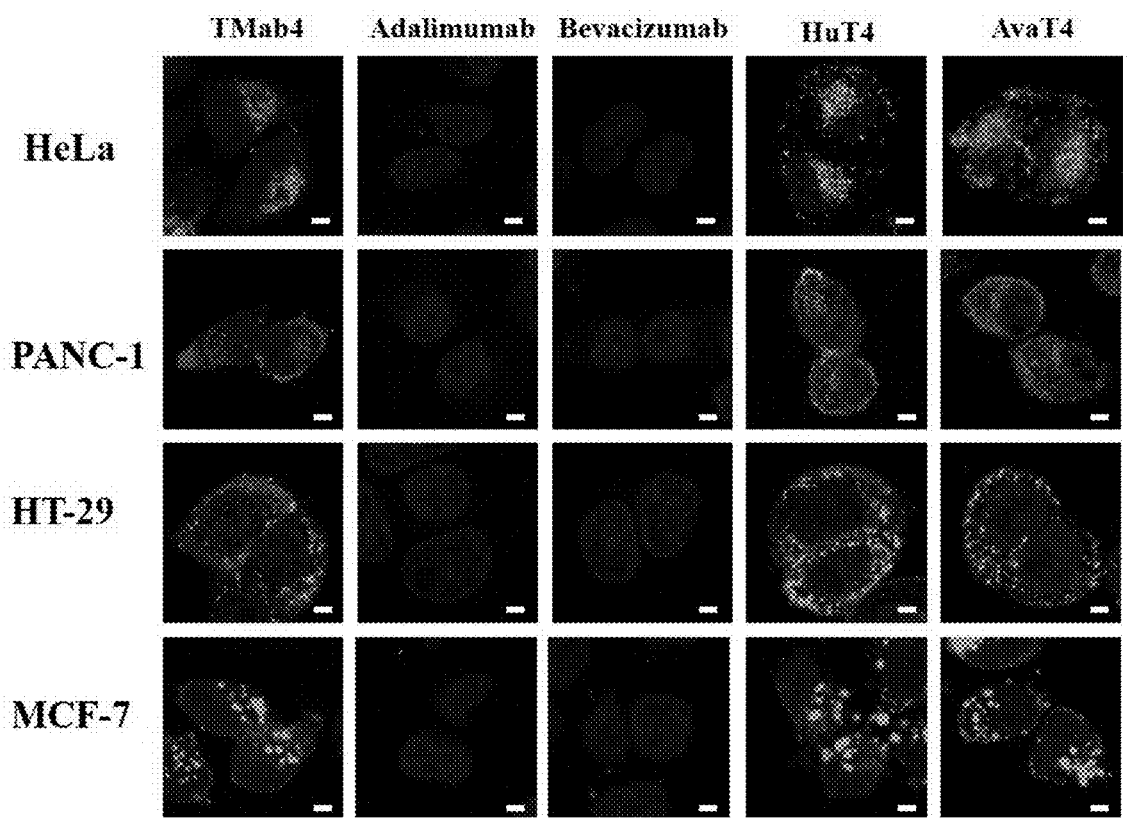
FIG. 9A shows the results of observing 1-2 cells in various cell lines by confocal microscopy in order to verify the cytosol-penetrating ability of cytotransmabs having a light-chain variable region replaced with the cytosol-penetrating light-chain region hT4 VL.

FIG. 9A shows the results of observing 1-2 cells in various cell lines by confocal microscopy in order to verify the cytosol-penetrating abilities of cytotransmabs having a light-chain variable region replaced with the cytosol-penetrating light-chain region hT4 VL.

Specifically, in a 24-well plate, $5 \times 10^4$ HeLa, PANC-1, HT29 or MCF-7 cells per well were added to 0.5 ml of 10% FBS-containing medium, and cultured for 12 hours under the conditions of 5% $CO_2$ and 37° C. When the cells were stabilized, each well was incubated with a dilution of each of 1 μM of TMab4, Adalimumab (Humira), Bevacizumab (Avastin), HuT4 or AvaT4 in 0.5 ml of fresh medium for 6 hours under the conditions of 37° C. and 5% $CO_2$. Next, the medium was removed, and each well was washed with PBS, and then treated with a weakly acidic solution (200 mM glycine, 150 mM NaCl (pH 2.5)) to remove proteins from the cell surface. After washing with PBS, the cells were fixed in 4% paraformaldehyde at 25° C. for 10 minutes. Next, each well was washed with PBS, and incubated with PBS buffer containing 0.1% saponin, 0.1% sodium azide and 1% BSA at 25° C. for 10 minutes to pores in the cell membranes. Next, each well was washed with PBS, and then incubated with PBS buffer containing 2% BSA at 25° C. for 1 hour in order to eliminate nonspecific binding. Thereafter, each well was incubated with FITC (green fluorescence)-labeled antibody (Sigma), which specifically recognizes human Fc, at 25° C. for 1.5 hours, and the nucleus was blue-stained with Hoechst33342, and observed with a confocal microscope. Unlike IgG-type monoclonal antibodies (Adalimumab and Bevacizumab) which target extracellularly secreted proteins, TMab4, HuT4 and AvaT4 showed green fluorescence in the cells.

Figure 9B:
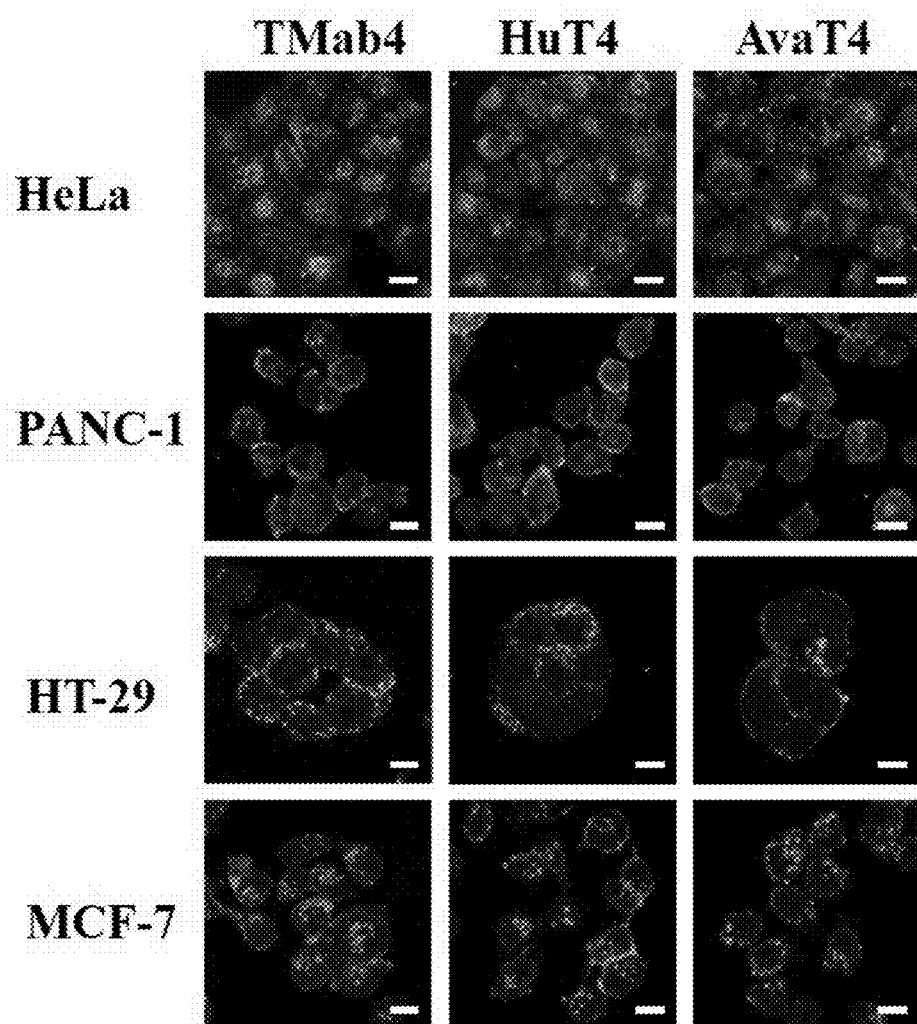
FIG. 9B shows the results of examining cytosol-penetrating ability for several cells, performed at a reduced magnification in order to examine cell-penetrating efficiency in the cytosol-penetrating ability examination experiment by confocal microscopy observation as shown in FIG. 7A.

FIG. 9B shows the results of examining cytosol-penetrating ability for several cells, performed at a reduced magnification in order to examine cell-penetrating efficiency in the cytosol-penetrating ability examination experiment by confocal microscopy observation as shown in FIG. 9A.

It was shown that the cytotransmab introduced with the cytosol-penetrating humanized light-chain variable region penetrated the cytosol of all the cells and localized in the cytosol.

Example 10: Evaluation of Cytotoxicity of Cytotransmabs

In order to examine whether or not the cytotransmabs confirmed to have cytosol-penetrating ability in Example 7 would have cytotoxicity in vitro, HeLa or PANC-1 cells were treated with each of TMab4, HuT4, Adalimumab, AvaT4 and Bevacizumab, and the inhibition of growth of the cells was examined by an MTT assay (Sigma).

Specifically, in a 96-well plate, $1 \times 10^4$ HeLa or PANC-1 cells per well were cultured in 0.1 ml of 10% FBS-containing medium for 12 hours under the conditions of 37° C. and 5% $CO_2$. Then, each well was treated with 1 μM of each of TMab4, HuT4, Adalimumab, AvaT4 and Bevacizumab for 20 hours or 44 hours, and then 20 μl of MTT solution (1 mg/ml PBS) was added to each well, followed by incubation for 4 hours. The formed formazan was dissolved in 200 μl of DMSO (dimethyl sulfoxide), and the absorbance at 595 nm was measured to determine cell viability.

Figure 10A:
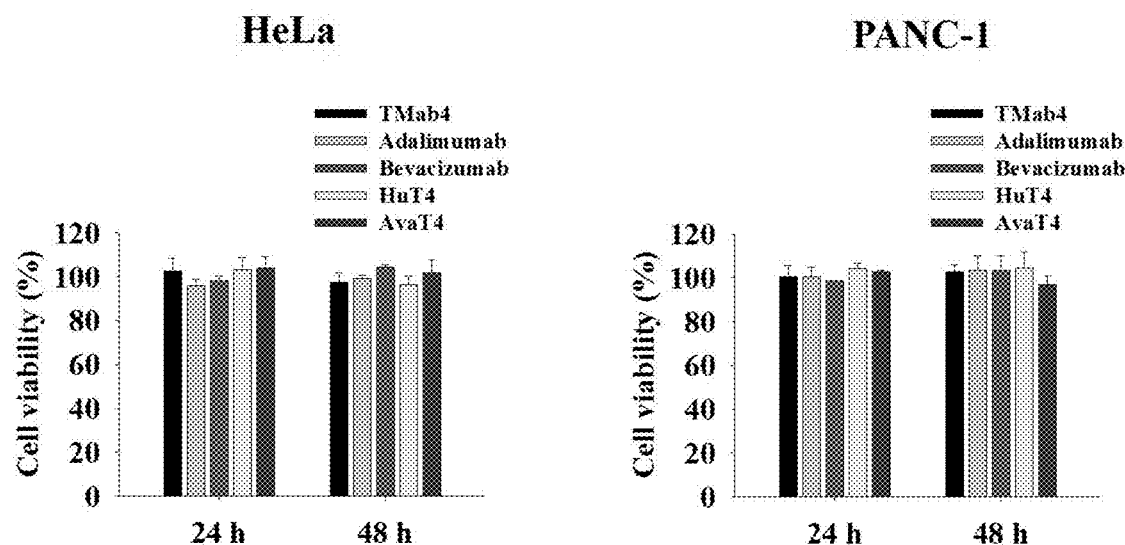
FIG. 10A is a graph showing the results obtained by treating HeLa and PANC-1 cell lines with cytotransmab and evaluating in vitro the inhibition of growth of the cells.
Figure 10B:
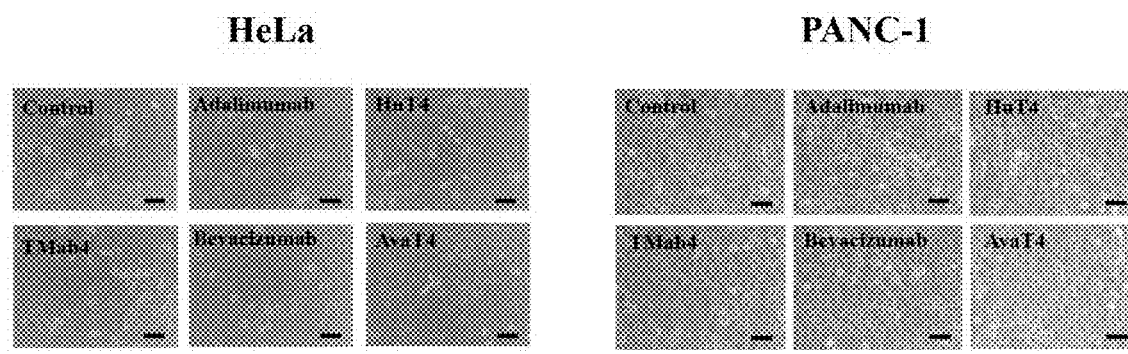
FIG. 10B is an image showing the results obtained by treating HeLa and PANC-1 cell lines with cytotransmab and evaluating in vitro the inhibition of growth of the cells.

FIG. 10A is a graph showing the results obtained by treating HeLa and PANC-1 cell lines with cytotransmab and evaluating the inhibition of growth of the cells in vitro). FIG. 10B is an image showing the results obtained by treating HeLa and PANC-1 cell lines with cytotransmab and evaluating the degree of inhibition of the cells in vitro. As shown in FIGS. 10A and 10B, all the antibodies showed no cytotoxicity.

Example 11: Expression and Purification of Anti-Ras•GTP iMab, and Analysis of Affinity of Anti-Ras•GTP iMab for KRas Mutants The heavy-chain variable region (VH) of cytotransmab, which has the property of penetrating cells and localizing in the cytosol, was replaced with RT4 VH selected in Example 3, thereby constructing anti-Ras•GTP iMab which can penetrate cells and specifically target GTP-bound Ras in the cytosol. The constructed anti-Ras•GTP iMab was expressed in animal cells.

Specifically, in order to construct a heavy-chain expression vector for producing an intact immunoglobulin-type monoclonal antibody, a DNA, which has a secretion peptide-encoding DNA fused to the 5' end and encodes a heavy chain comprising an RT11 heavy-chain variable region (RT11 VH) and a heavy-chain constant region (CH1-hinge-CH2-CH3), was cloned into a pcDNA3.4 (Invitrogen) vector by NotI/HindIII. In addition, in order to construct a light-chain expression vector, a DNA, which has a secretion peptide-encoding DNA fused to the 5' end and encodes a light chain encoding a cytosol-penetrating light-chain variable region (hT4 VL) and a light-chain constant region (CL), was cloned into a pcDNA3.4 (Invitrogen) vector by a NotI/HindIII.

The light-chain and heavy-chain expression vectors were transiently transfected, and the proteins were expressed and purified, followed by comparison of the yield of the proteins. In a shaking flask, HEK293-F cells (Invitrogen) suspension-growing in serum-free FreeStyle 293 expression medium (Invitrogen) were transfected with a mixture of plasmid and polyethyleneimine (PEI) (Polyscience). In the case of trans-fection of 200 mL in a shaking flask (Corning), HEK293-F cells were seeded into 100 ml of medium at a density of $2.0 \times 10^6$ cells/ml, and cultured at 150 rpm and in 8% $CO_2$. To produce each monoclonal antibody, suitable heavy-chain and light-chain plasmids were diluted in 10 ml of FreeStyle 293 expression medium (Invitrogen) (125 μg heavy chain, 125 μg light chain, a total of 250 μg (2.5 μg/ml)), and the dilution was mixed with 10 ml of medium containing 750 μg (7.5 μg/ml) of PEI, and the mixture was incubated at room temperature for 10 minutes. The incubated medium mixture was added to 100 ml of the seeded cell culture which was then cultured at 150 rpm in 8% $CO_2$ for 4 hours, after which 100 ml of FreeStyle 293 expression medium was added to the cell culture, followed by culture for 6 days. In accordance with the standard protocol, the protein was purified from the collected cell culture supernatant. The antibody was applied to a Protein A Sepharose column (GE Health-care), and the column was washed with PBS (pH 7.4). The antibody was eluted using 0.1 M glycine buffer (pH 3.0), and then immediately neutralized with 1M Tris buffer. The eluted antibody fraction was concentrated while the buffer was replaced with PBS (pH 7.4) by dialysis. The purified protein was quantified by measuring the absorbance at 280 nm and the absorption coefficient.

Figure 11:
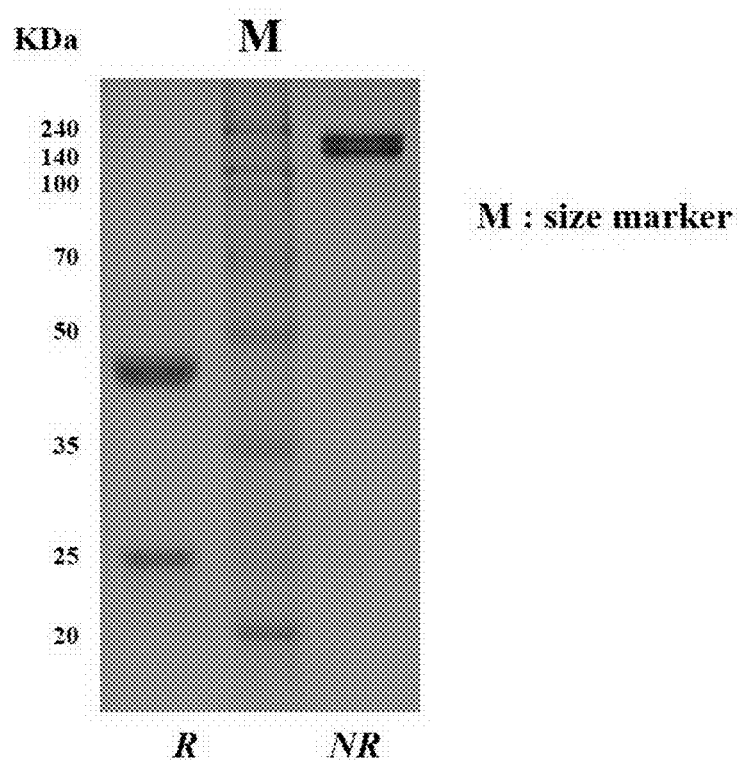
FIG. 11 shows the results of analyzing anti-Ras•GTP iMab RT4 by 12% SDS-PAGE under reductive or non-reductive conditions after purification.

FIG. 11 shows the results of analyzing anti-Ras•GTP iMab RT4 by 12% SDS-PAGE under reductive or non-reductive conditions after purification.

Specifically, in a non-reductive condition, a molecular weight of about 150 kDa appeared, and in a reductive condition, a heavy-chain molecular weight of about 50 kDa and a light-chain molecular weight of about 25 kDa appeared. This indicates that the expressed and purified anti-Ras•GTP iMab is present as a monomer in a solution state free of a non-covalent bond, and does not form a dimer or an oligomer by a non-natural disulfide bond.

Figure 12:
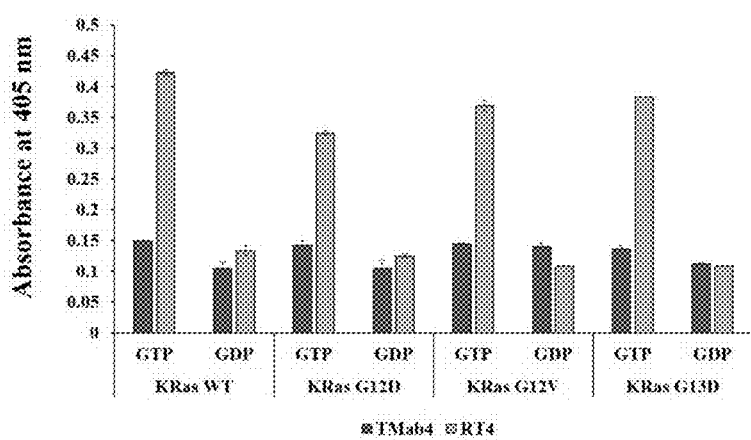
FIG. 12 shows the results of ELISA performed to measure affinity for GTP-bound and GDP-bound wild-type KRas and GTP-bound and GDP-bound KRas mutants (KRas G12D, KRas G12V, and KRas G13D).

FIG. 12 shows the results of ELISA performed to measure affinity for GTP-bound and GDP-bound wild-type KRas and GTP-bound and GDP-bound KRas mutants (KRas G12D, KRas G12V, and KRas G13D).

Specifically, each of GTP-bound KRas mutants and GDP-bound KRas mutants, which are target molecules, was incubated in a 96-well EIA/RIA plate (COSTAR Corning) at 37° C. for 1 hour, and then the plate was washed three times with 0.1% TBST (0.1% Tween20, pH 7.4, 137 mM NaCl, 12 mM Tris, 2.7 mM KCl, 5 mM $MgCl_2$) (SIGMA) for 10 minutes. Next, each well of the plate was incubated with 4% TBSB (4% BSA, pH7.4, 137 mM NaCl, 12 mM Tris, 2.7 mM KCl, 10 mM $MgCl_2$) (SIGMA) for 1 hour, and then washed three times with 0.1% TBST for 10 minutes. There-after, each well was incubated with anti-Ras•GTP iMab RT4 (and cytotransmab TMab4 having cytosol-penetrating abil-ity only without Ras-binding ability) diluted in 4% TBSB at various concentrations, after which each well was washed three times with 0.1% PBST for 10 minutes. As a marker antibody, goat alkaline phosphatase-conjugated anti-human mAb (SIGMA) was used. Each well was treated with pNPP (p-nitrophenyl palmitate) (SIGMA), and the absorbance at 405 nm was measured.

In order to further quantitatively analyze the affinity of anti-Ras•GTP iMab RT4 for GTP-bound KRas G12D, SPR (Surface plasmon resonance) was performed using a Biacore 2000 instrument (GE healthcare).

Specifically, anti-Ras•GTP iMab RT4 was diluted in 10 mM Na-acetate buffer (pH 4.0), and immobilized on a CM5 sensor chip (GE Healthcare) at a concentration of about 1100 response units (RU). For analysis, Tris buffer (20 mM Tris-HCl, pH 8.0, 100 mM NaCl, 5 mM MgCl2, 0.005% Tween 20) was flushed at a flow rate of 30 μl/min, and GTP-bound KRas G12D was used at a concentration rang-ing from 1000 nM to 62.5 nM. After analysis of association and dissociation, regeneration of the CM5 chip was per-formed by flushing a buffer (10 mM NaOH, 1M NaCl, pH10.0) at a flow rate of 30 μl/min for 1.5 minutes. Each of sensorgrams obtained at 3 min of association and 3 min of dissociation was normalized and subtracted from a blank cell, thereby determining affinity.

Figure 13:
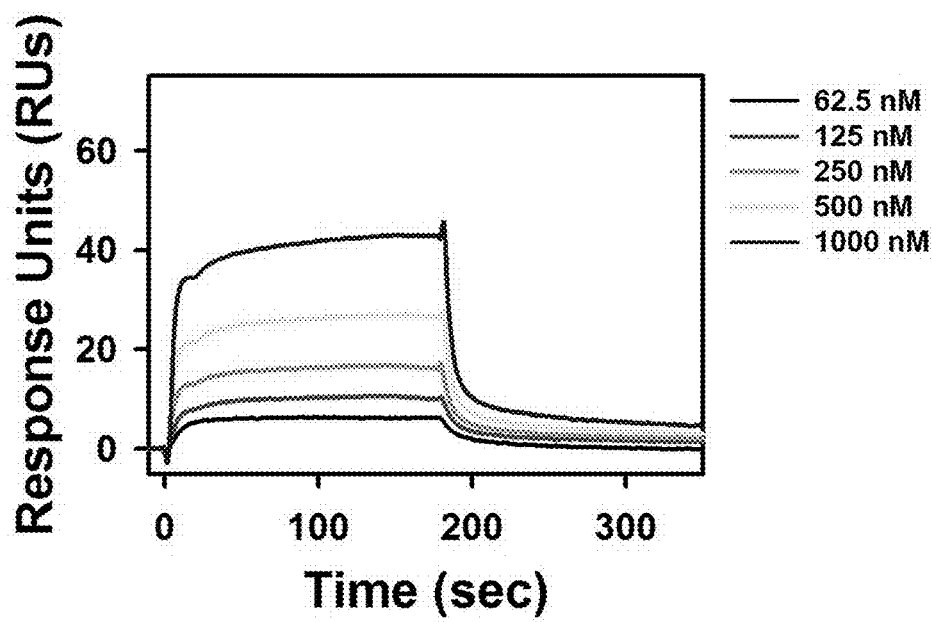
FIG. 13 shows the results of analyzing the affinity of anti-Ras•GTP iMab RT4 for GTP-bound KRAS G12D by use of SPR (BIACORE 2000) (GE Healthcare).

FIG. 13 shows the results of analyzing the affinity of anti-Ras•GTP iMab RT4 for GTP-bound KRAS G12D by use of SPR (BIACORE 2000) (GE Healthcare).

Example 12: Examination of Cytosol-Penetrating Ability of Anti-Ras•GTP iMab RT4

Figure 14:
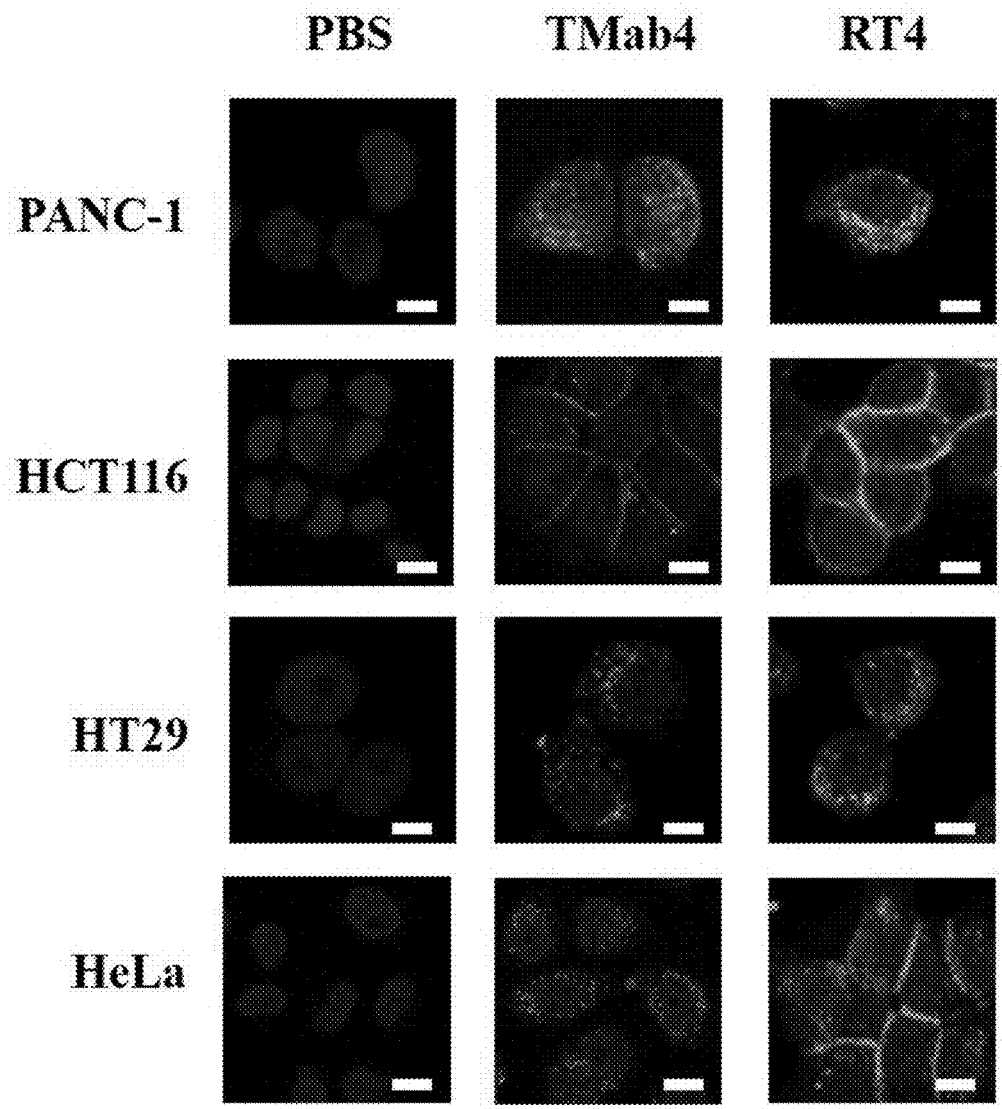
FIG. 14 shows the results of confocal microscopy observation performed to examine the cytosol-penetrating ability of anti-Ras•GTP iMab RT4.

FIG. 14 shows the results of confocal microscopy obser-vation performed to examine the cytosol-penetrating ability of anti-Ras•GTP iMab RT4. In cells lines (PANC-1, and HCT116) having mutant KRas and cell lines (HT29, HeLa) having wild-type KRas, the cell-penetrating ability of anti-Ras•GTP iMab RT4 was analyzed.

Specifically, each cell line was added to a 24-well plate at a density of $5 \times 10^4$ cells per well and cultured in 0.5 ml of 10% FBS-containing medium for 12 hours under the con-ditions of 5% $CO_2$ and 37° C. When the cells were stabi-lized, each of TMab4 and RT4, diluted in 0.5 ml of fresh medium at a concentration of 1 μM, was added to each well, followed by incubation for 6 hours under the conditions of 37° C. and 5% $CO_2$. Next, the medium was removed, and each well was washed with PBS, and then treated with a weakly acidic solution (200 mM glycine, 150 mM NaCl (pH 2.5)) to remove proteins from the cell surface. After washing with PBS, the cells were fixed in 4% paraformaldehyde at 25° C. for 10 minutes. Next, each well was washed with PBS, and incubated with PBS buffer containing 0.1% saponin, 0.1% sodium azide and 1% BSA at 25° C. for 10 minutes to pores in the cell membranes. Next, each well was washed with PBS, and then incubated with PBS buffer containing 2% BSA at 25° C. for 1 hour in order to eliminate nonspecific binding. Thereafter, each well was incubated with FITC (green fluorescence)-labeled antibody (Sigma), which specifically recognizes human Fc, at 25° C. for 1.5 hours, and the nucleus was blue-stained with Hoechst33342, and observed with a confocal microscope. It was observed that anti-Ras•GTP iMab showed fluorescence in the cells, indicating that cytotransmab did not lose its cytosol-pen-etrating ability, even after it was substituted with the heavy-chain variable region that binds specifically to GTP-bound KRas.

Example 13: Evaluation of Cytotoxicity of Anti-Ras•GTP iMab RT4

(1) Evaluation of the Effect of Anti-Ras•GTP iMab on Inhibition of Growth of Adherent Cells FIG. 15 shows the results obtained by treating NIH3T3, NIH3T3 KRas G12V and NIH3T3 HRas G12V cell lines with anti-Ras•GTP iMab RT4 and evaluating the inhibition of growth of the cells in vitro.

Specifically, in order to examine whether anti-Ras•GTP iMab has cytotoxicity specific for KRas mutant-dependent cells in vitro, wild-type KRas NIH3T3 mouse fibroblast cells, NIH3T3 KRas G12V cells having artificially overexpressed Ras mutant, NIH3T3 HRas G12V mutant cells, and KRas G13D mutant human pancreatic cells (PANC-1), were treated with 1 µM of each of TMab4 and RT4, and the inhibition of growth of adherent cells was evaluated.

Specifically, each type of NIH3T3 and PANC-1 cells was added to a 24-well plate at a density of $2\times10^3$ cells per well and cultured in 0.5 ml of 10% FBS-containing medium for 12 hours under the conditions of 37° C. and 5% $CO_2$. Next, the cells were treated twice with 1 µM of TMab4 or RT4 for 72 hours each time and observed for a total of 144 hours, and then the number of viable cells was counted, thereby determining the degree of growth of the cells.

As shown in FIG. 21, the cells treated with TMab4 showed no cytotoxicity, whereas RT4 inhibited the growth of the KRas mutant cell lines (NIH3T3 KRas G12V, and NIH3T3 HRas G12V), and the NIH3T3 cells showed no cytotoxicity. In addition, the growth of the KRas G13D mutant PANC-1 cells was inhibited. Thus, TMab4 had no cytotoxicity, whereas RT4 inhibited cell growth.

(2) Evaluation of the Effect of Anti-Ras•GTP iMab RT4 on Inhibition of Growth of Non-Adherent Cells FIG. 16 shows the results of evaluating the inhibition of growth of non-adherent cells in an NIH3T3 HRas G12V cell line.

Specifically, in order to examine whether anti-Ras•GTP iMab inhibits the growth of non-adherent cells in KRas mutant cells, NIH3T3 HRas G12V mutant cells were analyzed by a colony typeion assay. Specifically, a mixture of 0.5 ml of 2×DMEM medium and 0.5 ml of 1% agrose solution was plated on a 12-well plate and hardened to form 0.5% gel. Then, 0.4 ml of 2×DMEM medium, 0.5 ml of 0.7% agarose, and 0.05 ml of $1\times10^3$ NIH3T3 HRas G12V cells were mixed with 0.05 ml (20 µM) of PBS, TMab4, RT4 or Lonafarnib (20 µM), and the mixture was plated on the 0.5% agarose gel and hardened. Thereafter, the 0.35% agarose gel was treated with a dispersion of 1 µM of PBS, TMab4, RT4 or Lonafarnib in 0.5 ml of 1×DMEM at 3-day intervals for a total of 21 days. On day 21, the cells were stained with NBT (nitro-blue tetrazolium) solution, and then the number of colonies was counted.

Similarly to the results of the above-described experiment on the inhibition of growth of adherent cells, RT4 inhibited colony typeion, whereas TMab4 did not inhibit colony typeion.

The above results indicate that anti-Rasab4lue te RT4 bind specifically to Ras mutants in the cytosol and inhibits the growth of adherent and non-adherent cells.

Figure 17:
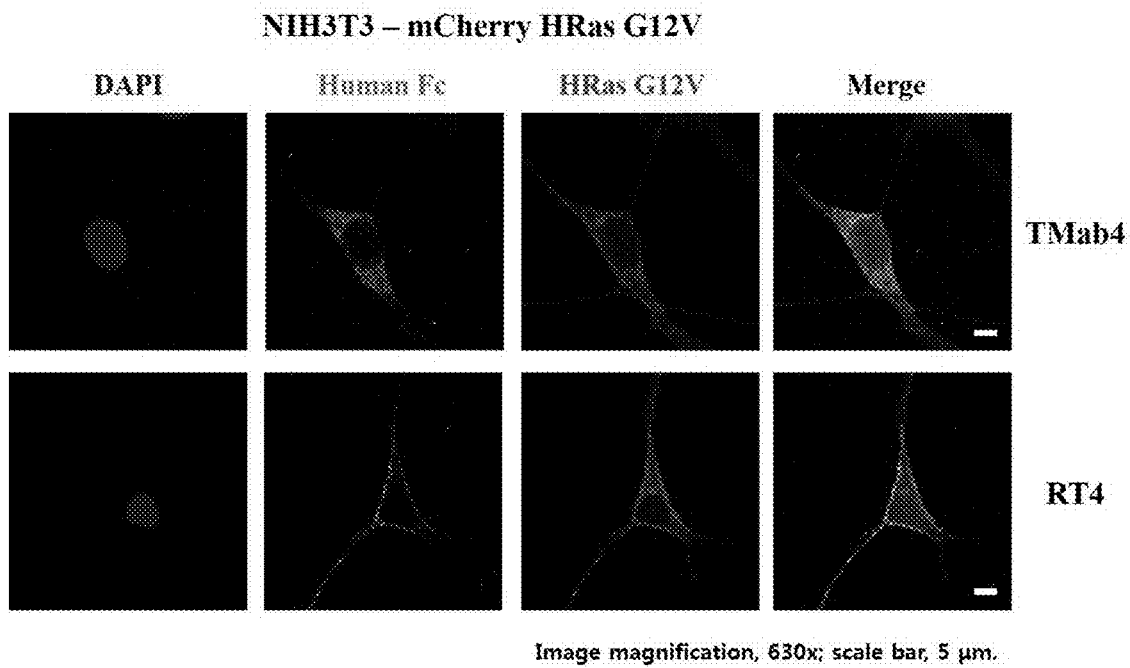
FIG. 17 shows the results of confocal microscopy observation of whether anti-Ras RT4 is superimposed with activated HRas G12V mutants in cells.
Figure 18:
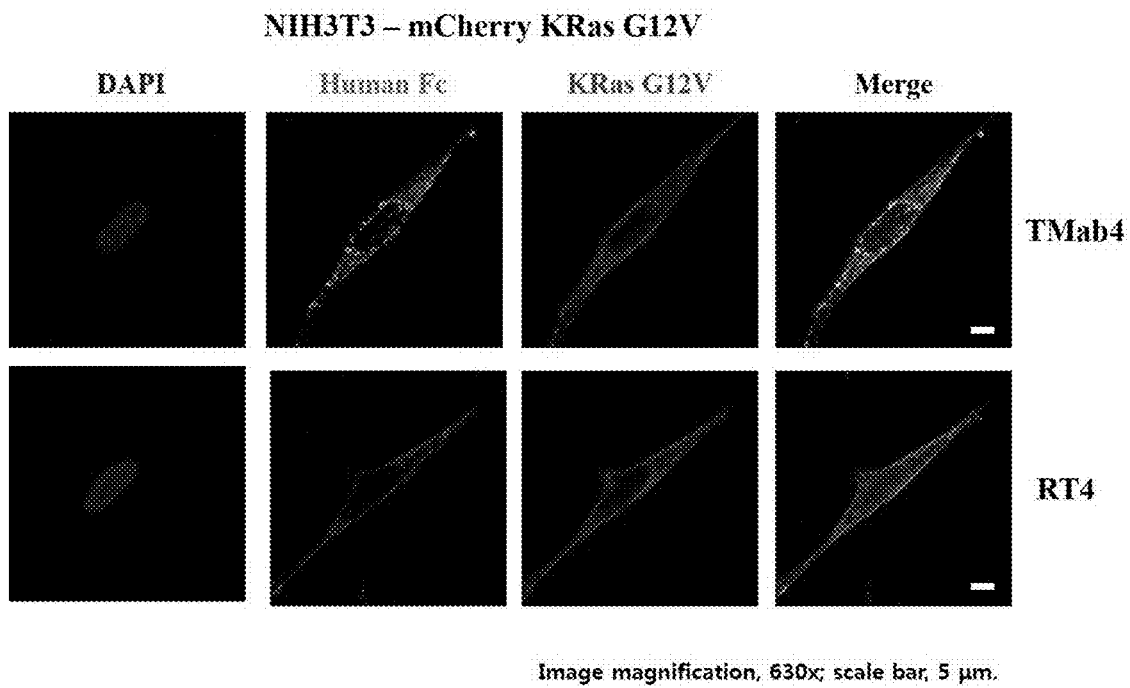
FIG. 18 shows the results of confocal microscopy observation of whether anti-Ras RT4 is superimposed with GTP-bound KRas G12V mutants in cells.

Example 14: Examination of Whether Anti-Ras•GTP iMab RT4 Binds Specifically to GTP-Bound KRas in Cells FIG. 17 shows the results of whether anti-Ras•GTP iMab RT4 is superimposed with activated HRas G12V mutants in cells. FIG. 18 shows the results of confocal microscopy observation of whether anti-RasG12V te is superimposed with GTP-bound KRas G12V mutants in cells.

Specifically, 24-well plates were coated with fibronectin (Sigma), and then a dilution of 0.5 ml of NIH3T3 cells expressing mCherry (red fluorescence) HRas G12V or mCherry (red fluorescence) KRas G12V was added to the plate at a density of $2\times10^4$ cells per well, and cultured for 12 hours under the conditions of 37° C. and 5% $CO_2$. Next, the cells were treated with 2 µM of each of TMab4 and RT4 and cultured at 37° C. for 12 hours. Next, the medium was removed, and each well was washed with PBS, and then treated with a weakly acidic solution (200 mM glycine, 150 mM NaCl (pH 2.5)) to remove proteins from the cell surface. After washing with PBS, the cells were fixed in 4% paraformaldehyde at 25° C. for 10 minutes. Next, each well was washed with PBS, and incubated with PBS buffer containing 0.1% saponin, 0.1% sodium azide and 1% BSA at 25° C. for 10 minutes to pores in the cell membranes. Next, each well was washed with PBS, and then incubated with PBS buffer containing 2% BSA at 25° C. for 1 hour in order to eliminate nonspecific binding. Thereafter, each well was incubated with FITC (green fluorescence)-labeled antibody (Sigma), which specifically recognizes human Fc, at 25° C. for 1.5 hours, and the nucleus was blue-stained with Hoechst33342, and observed with a confocal microscope.

As shown in FIGS. 17 and 18, green fluorescent RT4 was superimposed with the cellular inner membrane in which red-fluorescent activated Ras was located, whereas TMab was not superimposed.

The above experimental results indicate that anti-Ras Rasabhst3334 RT4 bind specifically to GTP-bound Ras in the cells.

Example 15: Evaluation of Cytotoxicity of RGD-Fused Anti-Ras1181t3334 RT4

For in vivo experiments, it is required to impart tumor tissue specificity. Conventional cytotransmabs bind to HSPG on the cell surface, and have no specificity for any other tumor tissue, and for this reason, cannot specifically inhibit the growth of tumors in in vivo experiments. To overcome this problem, an RGD4C peptide (CDCRGDCFC; SEQ ID NO: 41) having specificity for integrin αvβ3 which is overexpressed in angiogenetic cells and various tumors was fused to the N-terminus of the light chain via one GGGGS linker by a genetic engineering method. The RGD4C peptide is characterized in that it has affinity higher than conventional RGD peptides and can be fused using a genetic engineering method, and the specific structure thereof can be maintained even when it is fused to the N-terminus (Koivunen E et al., 1995).

Figure 19:
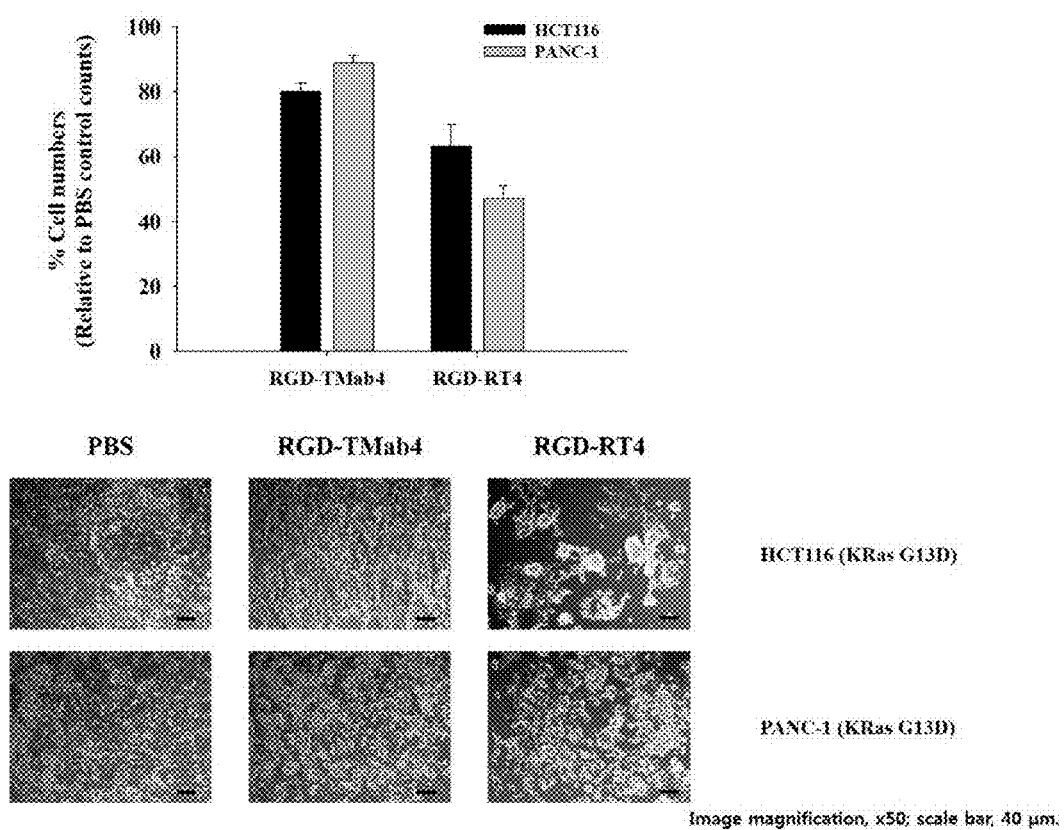
FIG. 19 shows the results obtained by treating HCT116 and PANC-1 cell lines with RGD-TMab4 and RGD-RT4 and evaluating in vitro the inhibition of growth of the cells.

FIG. 19 shows the results obtained by treating HCT116 and PANC-1 cell lines with RGD-TMab4 and RGD-RT4 and evaluating the inhibition of growth of the cells in vitro.

In order to examine whether RGD-TMab4 and RGD-RT4 themselves have cytotoxicity in vitro, human colorectal cancer HCT116 cells having a KRas G13D mutant, and human pancreatic cancer PANC-1 cells having a KRas G12D mutant, were treated with each of RGD-TMab4 and RGD-RT4, and the inhibition of growth of the cells was evaluated.

Specifically, each type of HCT116 and PANC-1 cells was added to a 24-well plate at a density of $5\times10^3$ cells per well, and cultured in 0.5 ml of 10% FBS-containing medium for 12 hours under the conditions of 37° C. and 5% $CO_2$. Next, the cells were treated twice with 1 µM of each of RGD-TMab4 and RGD-RT4 for 72 hours each time, and observed for a total of 144 hours, and then the number of the cells was counted, thereby determining the degree of growth of the cells.

As shown in FIG. 19, RGD-TMab4 inhibited the growth of HCT116 cells by about 20% and inhibited the growth of PANC-1 cells by about 15%, and RGD-RT4 inhibited the growth of HCT116 and PANC-1 cells by about 40% and about 50%, respectively. According to previous studies, the RGD4C peptide has an affinity for integrin αvβ5, which is about 3 times lower than that for integrin αvβ3. However, integrin αvβ3 is overexpressed mainly in angiogenetic cells, and integrin αvβ5 is expressed in various tumor cells. Thus, the RGD4C peptide has the ability to bind αvβ5 of HCT116 and PANC-1 cells to thereby inhibit cell adhesion (Cao L et al., 2008).

Thus, RGD4C peptide-fused TMab4 does not appear to have cytotoxicity. In addition, a comparison between RGD-TMab4 and RGD-RT4 indirectly confirmed that TMab4 can inhibit Ras-specific cell growth even when the RGD is fused thereto.

Figure 20A:
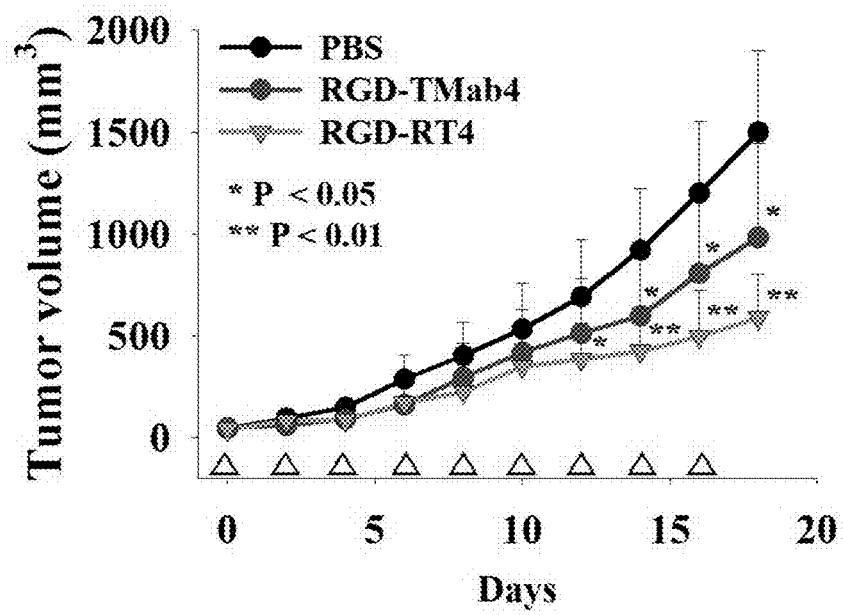
FIG. 20A shows the results of analyzing the tumor growth inhibitory effect of RGD-fused anti-Ras•GTP iMab RT4 in mice xenografted with HCT116 cells.
Figure 20B:
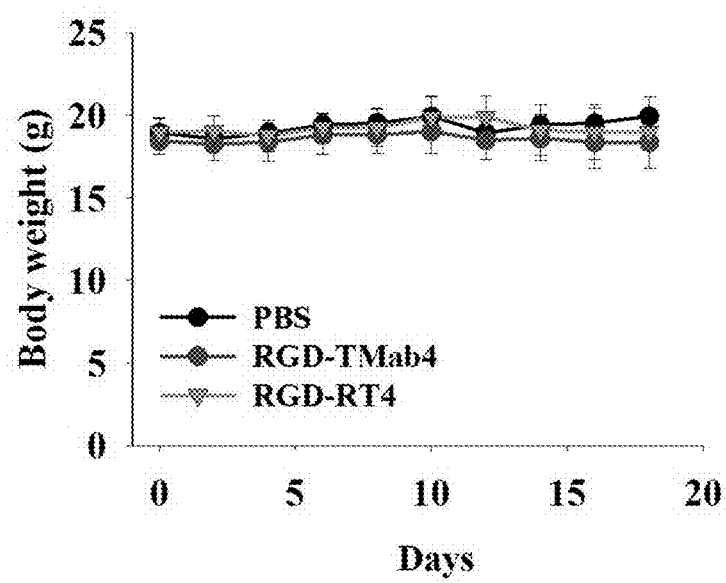
FIG. 20B is a graph showing the results of measuring the body weight of mice in order to examine the non-specific side effects of RGD-fused anti-Ras•GTP iMab RT4.

Example 16: Examination of the Effect of RGD-Fused Anti-Ras1181b4alC on Inhibition of Tumor Growth FIG. 20A shows the results of analyzing the tumor growth inhibitory effect of RGD-fused anti-Ras•GTP iMab RT4 in mice xenografted with HCT116 cells. FIG. 20B is a graph showing the results of measuring the body weight of mice in order to examine the non-specific side effects of RGD-fused anti-Ras•GTP iMab RT4.

Specifically, in order to examine the tumor growth inhibitory effect of RGD-RT4 in vivo based on the in vitro experiment results of Example 15, KRas G13D mutant human colorectal HCT116 cells were injected subcutaneously into Balb/c nude mice at a density of 5×10$^6$ cells per mice. After about 6 days when the tumor volume reached about 50 mm$^3$, the mice were injected intravenously with 20 mg/kg of each of PBS, RGD-TMab4 and RGD-RT4. The injection was performed a total of 9 times at 2-day intervals, and the tumor volume was measured using a caliper for 18 days.

As shown in FIG. 20A, unlike the control PBS, RGD-TMab4 and RGD-RT4 inhibited the growth of cancer cells, and RGD-RT4 more effectively inhibited tumor growth compared to RGD-TMab4. In addition, as shown in FIG. 20B, there was no change in the body weight of the test group treated with RGD-RT4, indicating that RGD-RT4 has no other toxicities.

Example 17: Construction and Screening of Library for Improving Affinity of Anti-Ras•GTP iMab RT4

Anti-Ras•GTP iMab RT4 shows Ras-specific biological activity, but the affinity thereof determined by SPR analysis is about 110 nM. Thus, it has a very low affinity for antigen, even though it is an IgG-type antibody. In order to improve this shortcoming and to allow anti-Ras•GTP iMab RT4 to exhibit increased biological activity even at low concentration, it is required to improve the affinity of anti-Ras•GTP iMab RT4.

Figures 21A, 21B:
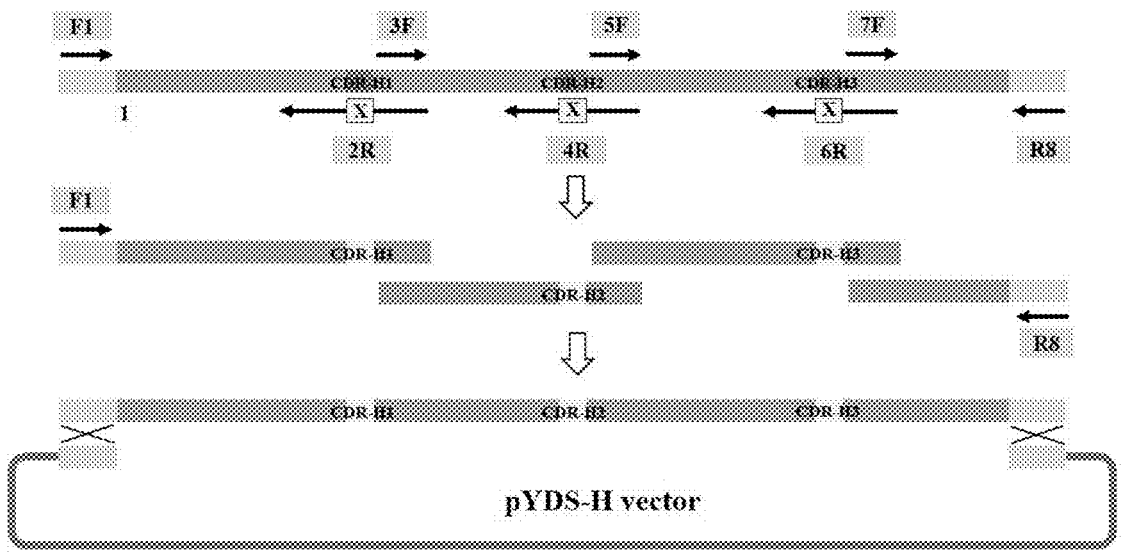
FIG. 21A shows a strategy of constructing a human heavy-chain variable region library to improve the affinity of RT4.
FIG. 21B is a schematic view showing a method of constructing a designed library by a PCR technique and transforming the constructed library onto the yeast surface by homologous combination with a heavy-chain single yeast surface display vector (pYDS-H) treated with the restriction enzymes NheI and ApaI.

FIG. 21A shows a strategy of constructing a human heavy-chain variable region library to improve the affinity of RT4. To improve affinity, CDR3 (residues 95 to 100a) playing an important role in binding to antigen was designed to have lengths of 6 residues (library 6), 7 residues (library 7) and 9 residues (library 9), and a degenerated codon (NNK) capable of encoding all amino acid residues was used. In addition, to improve the affinity and retain the antigen-binding site of RT4, a spiked oligomer capable of maintaining wild-type RT4 residues at a ratio of 50% was used for CDR1 (residues 31 to 33) and CDR2 (residues 50 and 52 to 56), which show high solvent accessibility. In this technology, a primer is designed such that the percentage of wild-type nucleotides in three nucleotides encoding an amino acid for each residue is maintained at 79% and the percentage of the remaining nucleotides is 7% so that wild-type amino acids in a PCR process will be maintained at 50%.

FIG. 21B is a schematic view showing a method of constructing a designed library by a PCR technique and transforming the constructed library onto the yeast surface by homologous combination with a heavy-chain single yeast surface display vector (pYDS-H) treated with the restriction enzymes NheI and ApaI.

Specifically, a DNA encoding each of the designed libraries was amplified by a PCR technique, and then enriched by ethanol precipitation. A pYDS-H heavy-chain yeast surface display vector for homologous recombination was treated with NheI and ApaI restriction enzymes, after which it was purified by agarose gel extraction and enriched by ethanol precipitation. For 12 μg of each library-encoding DNA, 5 μg of a vector was transformed into mating type A yeast JAR200 for yeast surface display by electroporation (Baek D. S and Kim Y. S, 2014; Lorenzo B et al., 2010), followed by serial dilution. The number of colonies in the selection medium SD-CAA+URA (20 g/L glucose, 6.7 g/L yeast nitrogen base without amino acids, 5.4 g/L Na2HPO$_4$, 8.6 g/L NaH$_2$PO$_4$, 5 g/L casamino acids, 0.2 mg/L uracil) was measured to determine the size of the library.

In each library screening process, according to the method as shown in Example 3 and 4, 1$^{st}$ MACS was performed for GTP-bound KRas G12D at an antigen concentration of 100 nM using the yeast library displaying the heavy-chain variable region alone. Then, for Fab libraries by yeast mating, clones specific for GTP-bound KRas G12D were selected through competitive binding to GDP-bound KRas G12D that was not biotinylated in 1$^{st}$, 2$^{nd}$ and 3$^{rd}$ FACS.

FIG. 22 shows the results of FACS analysis performed to determine the affinity of library 6 (which is a library having a CDR3 length of 6 residues) for GTP-bound KRas G12D and GDP-bound KRas G12D for library-expressing yeast in each step in order to confirm enrichment specific for GTP-bound KRas G12D in the above-described library screening process. As shown therein, the screened library did bind specifically to GTP-bound KRas G12D, and showed a higher affinity than RT4 used as a template.

FIG. 23 shows the results of sequencing of individual clones using the three libraries. As shown therein, only residues in the CDR region having mutations induced by the library were mutated.

Table 4 shows the human antibody heavy-chain variable region (VH) sequences of individual clones selected from the libraries having improved affinity by use of RT4 as a template, and, Table 5 below show the sequences of CDR1, CDR2 and CDR3 of the selected heavy-chain variable region (VH) sequences specific for Ras•GTP.

TABLE 4

Human antibody heavy-chain variable region (VH) sequences showing specific affinity for Ras · GTP, used in anti-Ras · GTP iMab

| Names of heavy-chain variable regions | Sequence | SEQ ID NO: |
|---|---|---|
| RT4 | 10 20 30<br>EVQLVESGGGLVQPGGSLRLSCAASGFTFS<br>40 50 a<br>SYAMSWVRQAPGKGLEWVSTISRSGHSTYY<br>60 70 80 abc<br>ADSVKGRFTISRDNSKNTLYLQMNSLRAED<br>90 a101 110<br>TAVYYCAKRFGSIVFDYWGQGTLVTVSS | SEQ ID NO: 1 |

TABLE 4-continued

Human antibody heavy-chain variable region (VH) sequences showing specific affinity for Ras · GTP, used in anti-Ras · GTP iMab

| Names of heavy-chain variable regions | Sequence | SEQ ID NO: |
|---|---|---|
| RT11 | ```
          10        20        30
EVQLVESGGGLVQPGGSLRLSCAASGFTFS
          40        50 a
SYSMSWVRQAPGKGLEWVSYISRTSHTTYY
          60        70        80 abc
ADSVKGRFTISRDNSKNTLYLQMNSLRAED
          90       a101       110
TAVYYCARGFF---MDYWGQGTLVTVSS
``` | SEQ ID NO: 2 |
| RT13 | ```
          10        20        30
EVQLVESGGGLVQPGGSLRLSCAASGFTFS
          40        50 a
TFSMSWVRQAPGKGLEWVSYISRTSHTTYY
          60        70        80 abc
ADSVKGRFTISRDNSKNTLYLQMNSLRAED
          90       a101       110
TAVYYCARGTFG--FDYWGQGTLVTVSS
``` | SEQ ID NO: 3 |
| RT14 | ```
          10        20        30
EVQLVESGGGLVQPGGSLRLSCAASGFTFS
          40        50 a
TFSMSWVRQAPGKGLEWVSYISRTSHTTYY
          60        70        80 abc
ADSVKGRFTISRDNSKNTLYLQMNSLRAED
          90       a101       110
TAVYYCARPRGW--FDYWGQGTLVTVSS
``` | SEQ ID NO: 4 |
| RT15 | ```
          10        20        30
EVQLVESGGGLVQPGGSLRLSCAASGFTFS
          40        50 a
TFSMSWVRQAPGKGLEWVSYISRTSHTTYY
          60        70        80 abc
ADSVKGRFTISRDNSKNTLYLQMNSLRAED
          90       a101       110
TAVYYCAKRFGS--FDYWGQGTLVTVSS
``` | SEQ ID NO: 5 |
| RT16 | ```
          10        20        30
EVQLVESGGGLVQPGGSLRLSCAASGFTFS
          40        50 a
TFSMSWVRQAPGKGLEWVSYISRTSHTTYY
          60        70        80 abc
ADSVKGRFTISRDNSKNTLYLQMNSLRAED
          90       a101       110
TAVYYCARSSGRFVFDYWGQGTLVTVSS
``` | SEQ ID NO: 6 |
| RT17 | ```
          10        20        30
EVQLVESGGGLVQPGGSLRLSCAASGFTFS
          40        50 a
TFSMSWVRQAPGKGLEWVSYISRTSHTTYY
          60        70        80 abc
ADSVKGRFTISRDNSKNTLYLQMNSLRAED
          90       a101       110
TAVYYCAKGRFGSVFDYWGQGTLVTVSS
``` | SEQ ID NO: 7 |

TABLE 5

CDR sequences of human antibody heavy-chain variable region (VH) showing specifc affinity for Ras · GTP, used in anti-Ras · GTP iMab

| Names of heavy-chain variable regions | CDR1 Sequence | | | | | SEQ ID NO: | CDR2 Sequence | | | | | | | | | | | | | | | SEQ ID NO: |
|---|---|---|---|---|---|---|---|---|---|---|---|---|---|---|---|---|---|---|---|---|---|---|---|
| Kabat No. | 31 | 32 | 33 | 34 | 35 | | 50 | 51 | 52 | 52a | 53 | 54 | 55 | 56 | 57 | 58 | 59 | 60 | 61 | 62 | 63 | 64 | 65 | |
| RT4 | S | Y | A | M | S | 8 | T | I | S | R | S | G | H | S | T | Y | Y | A | D | S | V | K | G | 9 |
| RT11 | S | Y | S | M | S | 11 | Y | I | S | R | T | S | H | T | T | Y | Y | A | D | S | V | K | G | 12 |
| RT13 | T | F | S | M | S | 14 | Y | I | S | R | T | S | H | T | T | Y | Y | A | D | S | V | K | G | 15 |
| RT14 | T | F | S | M | S | 17 | Y | I | S | R | T | S | H | T | T | Y | Y | A | D | S | V | K | G | 18 |
| RT15 | T | F | S | M | S | 20 | Y | I | S | R | T | S | H | T | T | Y | Y | A | D | S | V | K | G | 21 |
| RT16 | T | F | S | M | S | 23 | Y | I | S | R | T | S | H | T | T | Y | Y | A | D | S | V | K | G | 24 |
| RT17 | T | F | S | M | S | 26 | Y | I | S | R | T | S | H | T | T | Y | Y | A | D | S | V | K | G | 27 |

TABLE 5-continued

CDR sequences of human antibody heavy-chain variable region (VH) showing specifific affinity for Ras · GTP, used in anti-Ras · GTP iMab

| Names of heavy-chain variable regions Kabat No. | CDR3 Sequence | | | | | | | | SEQ ID NO: |
|---|---|---|---|---|---|---|---|---|---|
| | 95 | 96 | 97 | 98 | 99 | 100 | 100a | 101 102 | |
| RT4 | R | F | G | S | I | V | F | D Y | 10 |
| RT11 | G | F | F | – | – | – | M | D Y | 13 |
| RT13 | G | T | F | G | – | – | F | D Y | 16 |
| RT14 | P | R | G | W | – | – | F | D Y | 19 |
| RT15 | R | F | G | S | – | – | F | D Y | 22 |
| RT16 | S | S | G | R | F | V | F | D Y | 25 |
| RT17 | G | R | F | G | S | V | F | D Y | 28 |

Example 18: Expression and Purification of Anti-Ras•GTP iMab Having Improved Affinity As described in Example 11, a heavy chain comprising the heavy-chain variable region, obtained by library screening and having an improved affinity for Ras•GTP, a heavy-chain constant region (CH1-hinge-CH2-CH3), was cloned into an animal expression vector. The expression vector and a vector expressing a cytosol-penetrating humanized light-chain were transiently co-transfected into HEK293F protein-expression cells. Anti-Ras•GTP iMab was expressed in the cells and purified in the same manner as described in Example 11.

Figure 24:
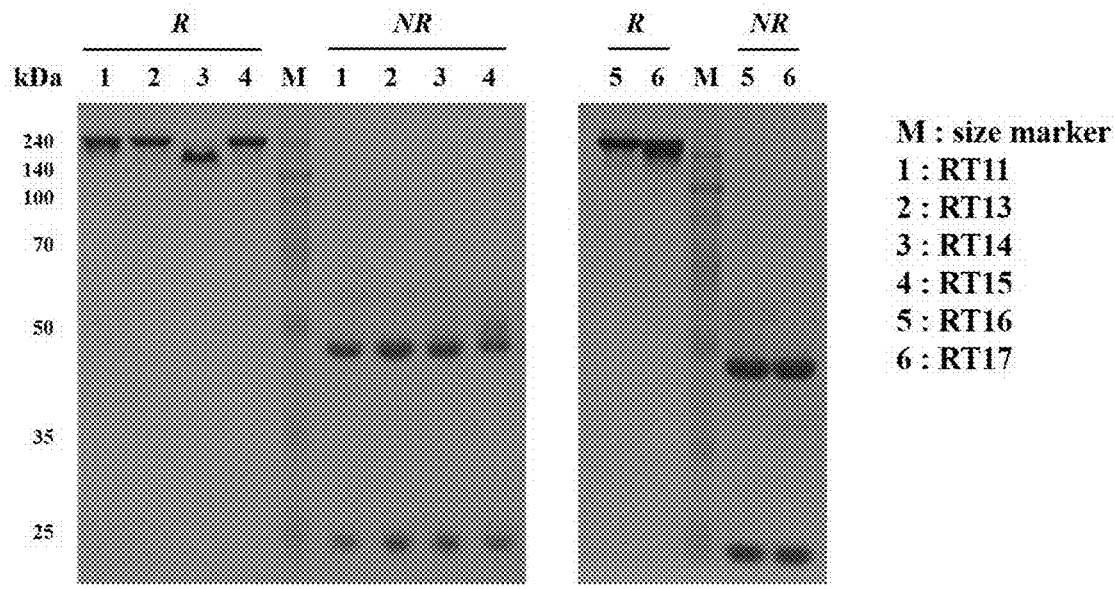
FIG. 24 shows the results of analyzing anti-RAS•GTP iMab having improved affinity by 12% SDS-PAGE under a reductive or non-reductive condition.

FIG. 24 shows the results of analyzing anti-RAS•GTP iMab having improved affinity by 12% SDS-PAGE under a reductive or non-reductive condition.

Specifically, as described in Example 11, in a non-reductive condition, a molecular weight of about 150 kDa appeared, and in a reductive condition, a heavy-chain molecular weight of about 50 kDa and a light-chain molecular weight of about 25 kDa appeared. This indicates that the expressed and purified anti-Ras•GTP iMab is present as a monomer in a solution state and does not form a dimer or an oligomer by a non-natural disulfide bond.

Figure 25:
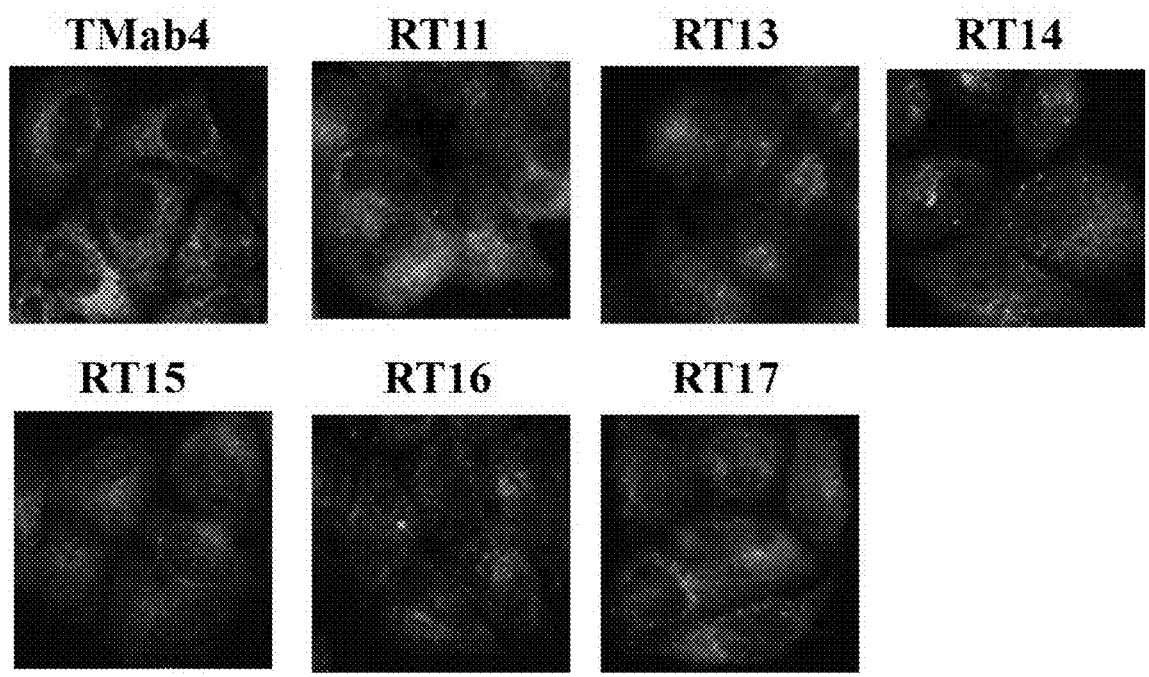
FIG. 25 shows the results obtained by replacing the heavy-chain variable region of anti-Ras•GTP iMab with a Ras•GTP-specific heavy-chain variable region having improved affinity and then performing confocal microscopic observation to confirm whether or not the anti-Ras•GTP iMab has the ability to penetrate cells.

Example 19: Examination of Cell-Penetrating Ability of Ras•GTP iMab Having Improved Affinity FIG. 25 shows the results obtained by replacing the heavy-chain variable region of anti-Ras•GTP iMab with a Ras•GTP-specific heavy-chain variable region having improved affinity and then performing confocal microscopic observation to confirm whether or not the anti-Ras•GTP iMab has the ability to penetrate cells.

Specifically, HeLa cells were added to each well of a 24-well plate at a cell density of 5×10$^4$ cells per well with 0.5 ml of 10% FBS-containing medium, and cultured for 12 hours under the conditions of 5% CO$_2$ and 37° C. When the cells were stabilized, a 1:17 dilution of each of TMab4, RT11, RT13, RT14, RT15, RT16 and RT17 in 0.5 ml of fresh medium was added to each well which was then incubated for 6 hours under the conditions of 5% CO$_2$ and 37° C. A subsequent process was performed in the same manner as the RT4 staining process described in Example 14. The intracellular fluorescence of RT11, RT13, RT14, RT15, RT16 and RT17, which are anti-Ras. GTP iMab having improved affinity, were observed, indicating that they have the ability to penetrate cells.

Example 20: Analysis of GTP-Bound Ras-Specific Affinity of Anti-Ras•GTP iMab Clones Having Improved Affinity FIG. 26A shows the results of ELISA performed to measure the affinity of the anti-Ras•GTP iMab clones having improved affinity for GTP-bound KRas G12D and GDP-bound KRas G12D.

Specifically, according to the same method as described in Example 11, each of GTP-bound KRas mutants and GDP-bound KRas mutants, which are target molecules, was incubated in a 96-well EIA/RIA plate (COSTAR Corning) at 37° C. for 1 hour, and then the plate was washed three times with 0.1% TBST (0.1% Tween20, pH 7.4, 137 mM NaCl, 12 mM Tris, 2.7 mM KCl, 5 mM MgCl$_2$) (SIGMA) for 10 minutes. Next, each well of the plate was incubated with 4% TBSB (4% BSA, pH7.4, 137 mM NaCl, 12 mM Tris, 2.7 mM KCl, 10 mM MgCl$_2$) (SIGMA) for 1 hour, and then washed three times with 0.1% TBST for 10 minutes. Thereafter, each well was incubated with each of the anti-Ras•GTP iMab clones diluted in 4% TBSB at various concentrations, after which each well was washed three times with 0.1% TBST for 10 minutes. As a marker antibody, goat alkaline phosphatase-conjugated anti-human mAb (SIGMA) was used. Each well was incubated with Ultra TMB-ELISA substrate solution (Thermo Scientific), and then the absorbance at 450 nm was measured.

Figure 26A:
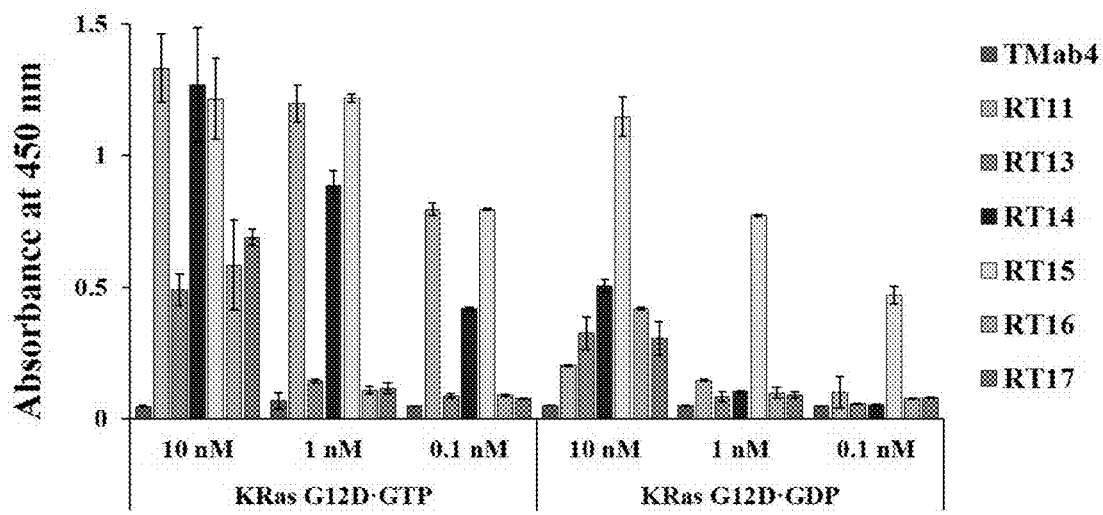
FIG. 26A shows the results of ELISA performed to measure the affinity anti-Ras•GTP iMab having improved affinity for GTP-bound KRas G12D and GDP-bound KRas G12D.

As shown in FIG. 26A, among the anti-Ras. GTP iMab clones having improved affinity, RT11 was selected as a clone having a high specific affinity for GTP-bound KRas G12D.

Figure 26B:
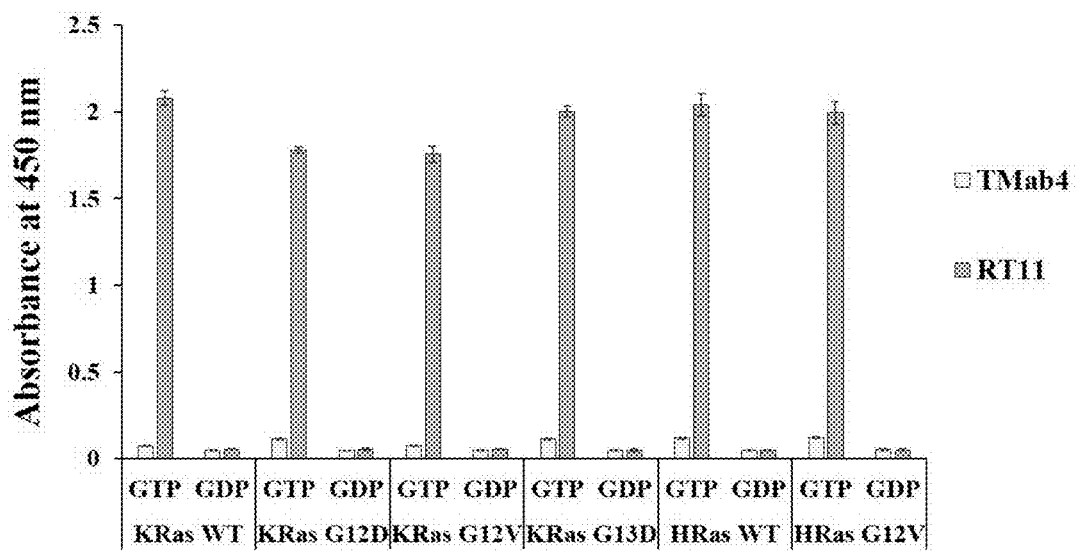
FIG. 26B shows the results of ELISA analysis performed to confirm the highly specific affinity of RT11, selected based on the ELISA-based binding analysis, for various GTP-bound Ras mutants.

FIG. 26B shows the results of ELISA analysis performed to confirm the affinity of RT11, selected based on the ELISA-based binding analysis, for various GTP-bound Ras mutants.

Specifically, using the same ELISA method used in the above-described analysis of the affinity of anti-Ras•GTP iMab having improved affinity, the affinities of anti-Ras•GTP iMab RT11 for GTP- or GDP-bound wild-type KRas, KRas G12D, KRas G12V, KRas G13D, wild-type HRas and HRas G12V, were analyzed.

As shown in FIG. 26B, anti-Ras•GTP iMab RT11 did bind to various GTP-bound Ras mutants.

Example 21: Quantitative Analysis of the Affinity of Anti-Ras•GTP iMab RT11 for KRas G12D In order to quantitatively analyze the affinity of anti-Ras•GTP iMab RT11 for GTP-bound KRas G12D, SPR (surface plasmon resonance) was performed using a Biacore 2000 instrument (GE Healthcare).

Figure 27A:
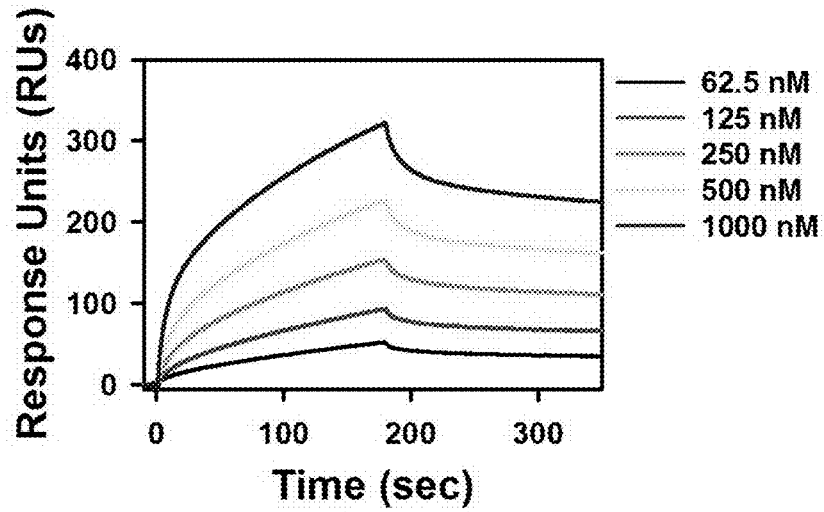
FIG. 27A shows the results of analyzing the affinity of anti-Ras•GTP iMab RT11 for GTP-bound KRas G12D by use of SPR (BIACORE 2000) (GE Healthcare).

FIG. 27A shows the results of analyzing the affinity of anti-Ras•GTP iMab RT11 for GTP-bound KRas G12D by use of SPR (BIACORE 2000) (GE Healthcare).

Figure 27B:
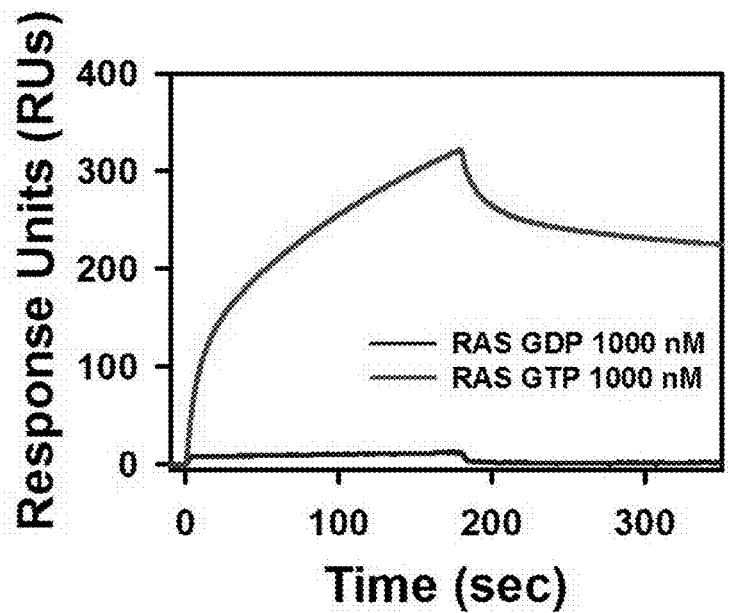
FIG. 27B is a sensorgram showing the results of analyzing the affinity of RT11 for GTP- or GDP-bound KRas G12D at the highest concentration (1000 nM).

FIG. 27B is a sensorgram showing the results of analyzing the affinity of RT11 for GTP- or GDP-bound KRas G12D at the highest concentration (1000 nM).

Specifically, according to the same method as described in Example 11, anti-Ras•GTP iMab RT11 was immobilized on a CM5 sensor chip (GE Healthcare) at a concentration of about 1100 response units (RU). For analysis, Tris buffer (20 mM Tris-HCl, pH 8.0, 100 mM NaCl, 5 mM $MgCl_2$, 0.005% Tween 20) was flushed at a flow rate of 30 µl/min, and GTP- or GDP-bound KRas G12D was used at a concentration ranging from 1000 nM to 62.5 nM.

As a result, it was shown that RT11 did bind to KRas G12D with high affinity (12.9 nM).

Example 22: Analysis of the Ability of Anti-Ras•GTP iMab RT11 to Inhibit Binding Between GTP-Bound KRas and Raf FIG. 28 shows the results of a competitive ELISA performed to confirm whether anti-Ras•GTP iMab RT11 can inhibit the binding between the effector molecule Raf and intracellular KRas.

Specifically, the Ras binding site (RBD: 1-149) fragment of the effector protein cRaf (NM_002880.2) was cloned into the *E. coli* expression vector pGEX-3X by the restriction enzymes BamHI/EcoRI, and then expressed and purified according to the same method as described in Example 2. The purified cRaf-RBD was incubated in a 96-well EIA/RIA plate (COSTAR Corning) at 37° C. for 1 hour, and then the plate was washed three times with 0.1% TBST (0.1% Tween20, pH 7.4, 137 mM NaCl, 12 mM Tris, 2.7 mM KCl, 5 mM $MgCl_2$) (SIGMA) for 10 minutes. Each well of the plate was incubated with 4% TBSB (4% BSA, pH7.4, 137 mM NaCl, 12 mM Tris, 2.7 mM KCl, 10 mM $MgCl_2$) (SIGMA) for 1 hour, and then washed three times with 0.1% TBST for 10 minutes. Next, each concentration of anti-Ras•GTP iMab RT11 diluted in 4% TBSB at various concentrations (ranging from 1 µM to 5.64 pM) was incubated with 1 µM of biotinylated GTP-bound KRas G12D, and then each well was washed three times with 0.1% TBST for 10 minutes. As a marker antibody, goat alkaline phosphatase-conjugated anti-human mAb (SIGMA) was used. Each well was incubated with pNPP (p-nitrophenyl palmitate) (SIGMA), and the absorbance at 405 nm was measured.

Figure 28:
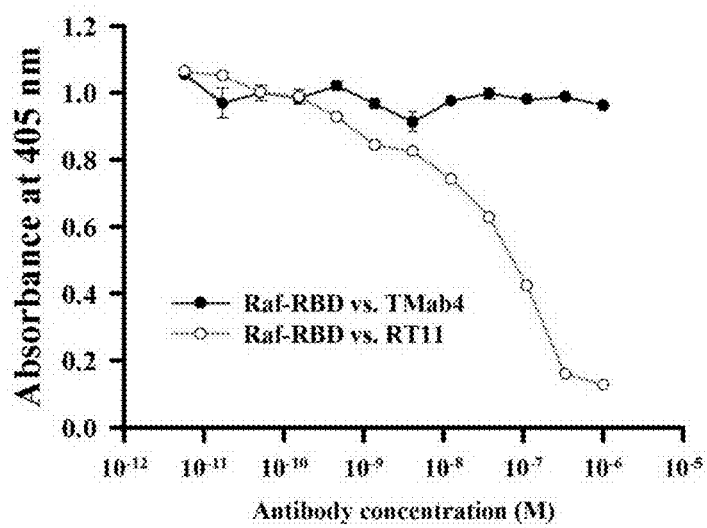
FIG. 28 shows the results of a competitive ELISA performed to confirm whether anti-Ras•GTP iMab RT11 can inhibit the binding between the effector molecule Raf and intracellular KRas.

As shown in FIG. 28, anti-Ras•GTP iMab RT11 showed the ability to inhibit binding to the effector protein cRaf ($IC_{50}$=35 nM).

Figure 29:
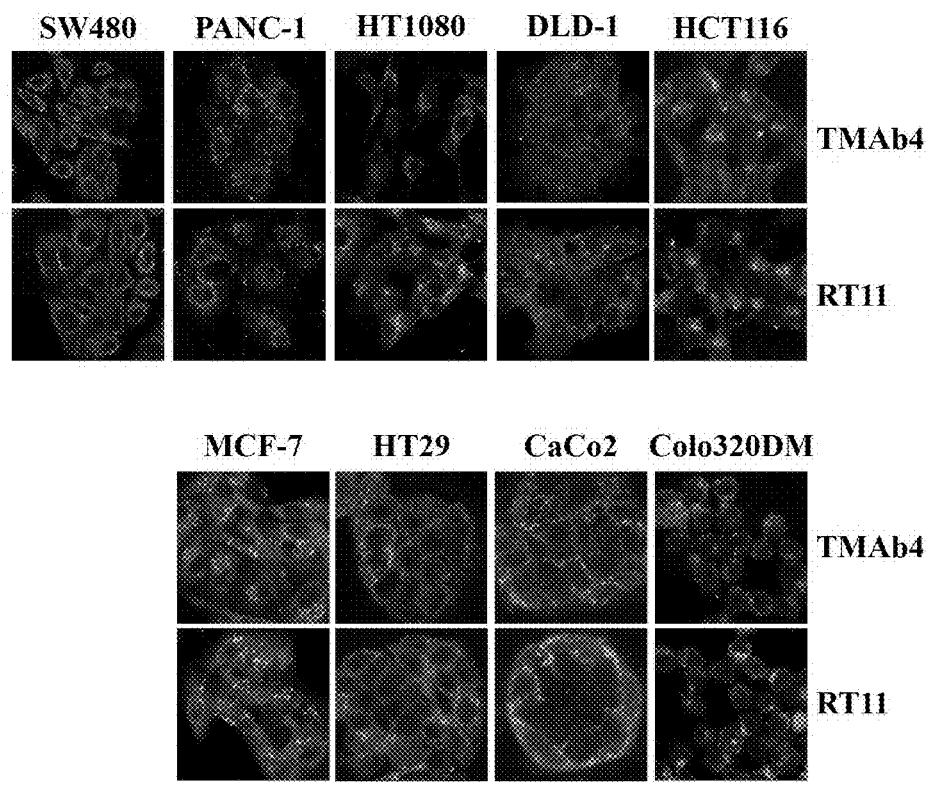
FIG. 29 shows the results of confocal microscopic observation performed to confirm whether anti-Ras•GTP iMab having improved affinity has the ability to penetrates various types of tumor cells.

Example 23: Examination of the Ability of Anti-Ras•GTP iMab RT11 to Penetrate Various Tumor Cells FIG. 29 shows the results of confocal microscopic observation performed to confirm whether anti-Ras•GTP iMab having improved affinity has the ability to penetrates various types of tumor cells. Various tumor cell lines, including human colorectal cancer cell lines (SW480 (KRasG12V mutant), PANC-1 (KRas G12D mutant), DLD-1 (KRas G13D mutant), HCT116 (KRas G13D mutant)), and a human fibrosarcoma cell line (HT1080 (NRas Q61L mutant), were used as Ras mutant cell lines, and a human breast cancer cell line (MCF7) and human colorectal cancer cell lines (HT29, CaCo2, Colo320DM) were used as Ras wild-type cell lines.

Specifically, each of the above-described Ras mutant and Ras wild-type cell lines was added to each of a 24-well plate at a density of $5 \times 10^4$ cells with 0.5 ml of 10% FBS-containing medium, and cultured for 12 hours under the conditions of 5% $CO_2$ and 37° C. When the cells were stabilized, each of TMab4 and RT11 diluted in fresh well at a concentration of 2 µM was added to each well which was then incubated for 12 hours under the conditions of 37° C. and 5% $CO_2$. A subsequent process was performed in the same manner as the RT4 staining process described in Example 14. As a result, anti-Ras•GTP iMab RT11 having improved affinity showed fluorescence in various types of tumor cells, indicating that it has the ability to penetrate various tumor cell lines, in the same manner as TMab4.

Figure 30:
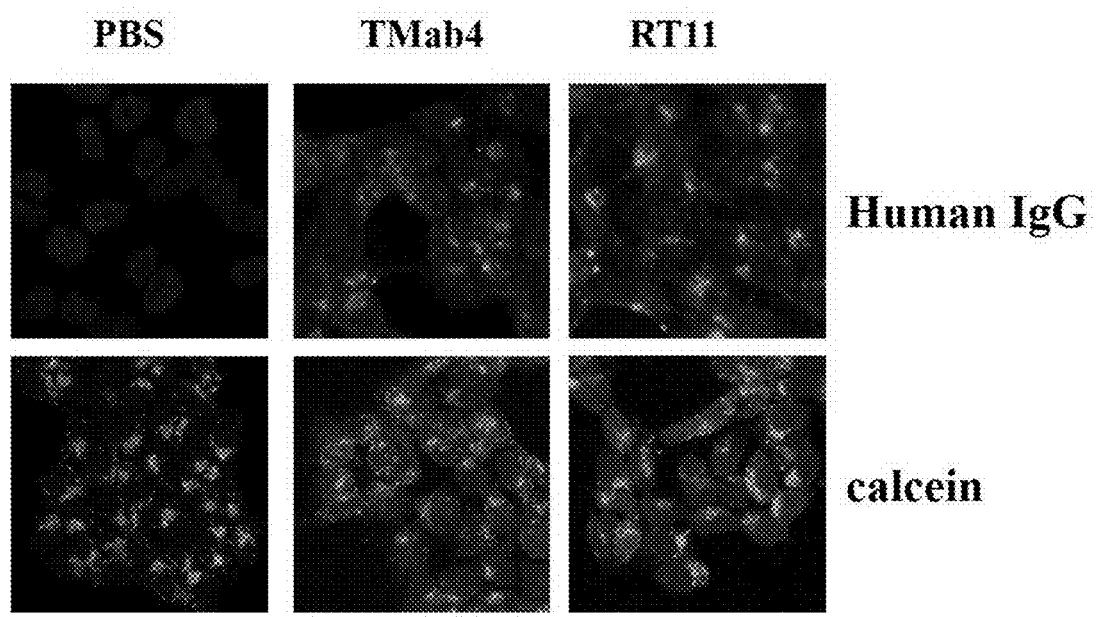
FIG. 30 shows the results of confocal microscopic observation performed using a non-cell-penetrating, self-quenching dye (calcein (Sigma)) to observe the cytosol-remaining ability of anti-Ras•GTP iMab having improved affinity.

Example 24: Examination of the Ability of Anti-Ras•GTP iMab RT11 to Remain in Cytosol FIG. 30 shows the results of confocal microscopic observation performed using a non-cell-penetrating, self-quenching dye (calcein (Sigma)) to observe the cytosol-remaining ability of anti-Ras•GTP iMab having improved affinity.

Specifically, HCT116 cells were added to each well of a 24-well plate at a density of $5 \times 10^4$ cells per well with 0.5 ml of 10% FBS-containing medium, and cultured for 12 hours under the conditions of 37° C. and 5% $CO_2$. Next, each well was treated with 1 µM of TMab4 and RT4 for 4 hours, and then treated with 100 µM of Calcein for 2 hours. Thereafter, the medium was removed, and each well was washed with PBS, and then treated with a weakly acidic solution (200 mM glycine, 150 mM NaCl pH 2.5) to remove calcein from the cell surface. After washing with PBS, the cells were fixed with 4% paraformaldehyde at 25° C. for 10 minutes. Next, each well was washed with PBS, and the nucleus was blue-stained with Hoechst33342 and observed with a confocal microscope. As shown in FIG. 30, both the anti-Ras•GTP iMab RT11 and the cytotransmab TMab4 showed calcein fluorescence throughout the cytosol. However, PBS showed only vesicle-shaped fluorescence. Such results indicate that anti-Ras•GTP iMab RT11 remained in the cytosol.

Example 25: Evaluation of Cytotoxicity of Anti-Ras•GTP iMab RT11

Figure 31:
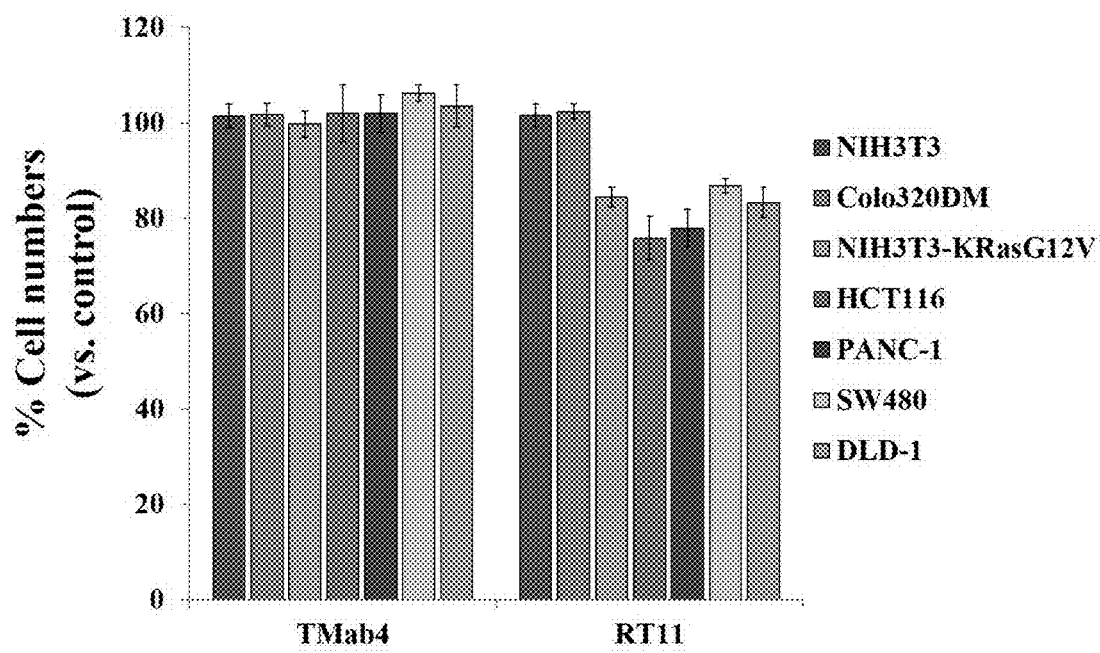
FIG. 31 shows the results obtained by treating various Ras wild-type and Ras mutant cell lines with anti-Ras•GTP iMab RT11 and evaluating in vitro the inhibition of growth of the cells.
Figure 32:
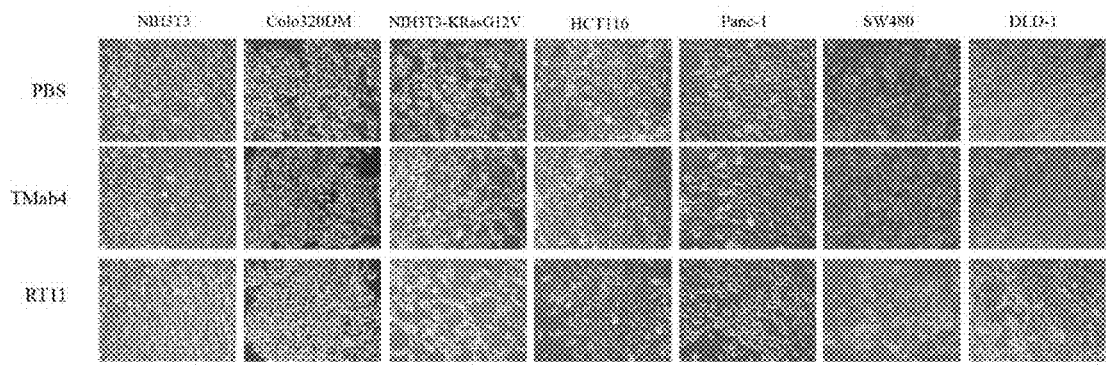
FIG. 32 are a set of images showing the results of polarizing microscopic observation performed to determine the cell density of each cell line.

FIG. 31 shows the results obtained by treating various Ras wild-type and Ras mutant cell lines with anti-Ras•GTP iMab RT11 and evaluating in vitro the inhibition of growth of the cells, and FIG. 32 are a set of images showing the results of polarizing microscopic observation performed to the cell density of each cell line.

Specifically, in order to examine in vitro whether anti-Ras•GTP iMab RT11 has cytotoxicity specific for Ras mutant cell lines, the inhibition of growth of cells was evaluated using mouse NIH3T3 fibroblast cells and human colorectal cancer Colo320DM cells as Ras wild-type cell lines and using mouse NIH3T3 KRas G12V mutant cells, human colorectal cancer cell lines (HCT116 cells (KRas G13D), HCT116 (KRas G13D), SW480 (KRas G12V), DLD-1 (KRas G13D)) and a human pancreatic cell line (PANC-1 (KRas G12D)).

Specifically, each type of the above-described cell lines was added to each well of a 24-well plate at a density of $2\text{-}5\times10^3$ cells per well with 0.5 ml of 10% FBS-containing medium, and cultured for 12 hours under the conditions of 37° C. and 5% $CO_2$. Next, each well was treated twice with each of TMab4 and RT11 for 72 hours each time and observed for a total of 144 hours, and then the number of viable cells was counted, thereby determining the degree of growth of the cells.

As shown in FIGS. 31 and 32, TMab4 showed no cytotoxicity, whereas RT11 inhibited the growth of only Ras mutant cells (NIH3T3 KRas G12V, HCT116, PANC-1, SW480, and DLD-1), and showed no cytotoxicity in Ras wild-type cell lines (NIH3T3, and Colo320DM).

Example 26: Examination of the Abilities of Anti-Ras•GTP iMab RT11 to Bind Specifically to Intracellular Activated Ras and to Inhibit Binding Between Activated Ras and Effector Protein (1) Examination of the Ability of Anti-Ras•GTP iMab RT11 to Bind Specifically to Intracellular Ras•GTP FIG. 33 shows the results of confocal microscopic observation performed to examine whether RT11 is superimposed with activated KRas G12V mutants in cells.

Specifically, 24-well plates were coated with fibronectin (Sigma), and then 0.5 ml of a dilution of NIH3T3 cells expressing mCherry (red fluorescence) HRas G12V was added to the plate at a density of $2\times10^2$ cells per well, and cultured for 12 hours under the conditions of 37° C. and 5% $CO_2$. Next, the cells were treated with 2 μM of each of TMab4 and RT11 and cultured at 37° C. for 12 hours. Thereafter, the cells were stained under the same conditions as described in Example 14, and were observed with a confocal microscope.

Figure 33:
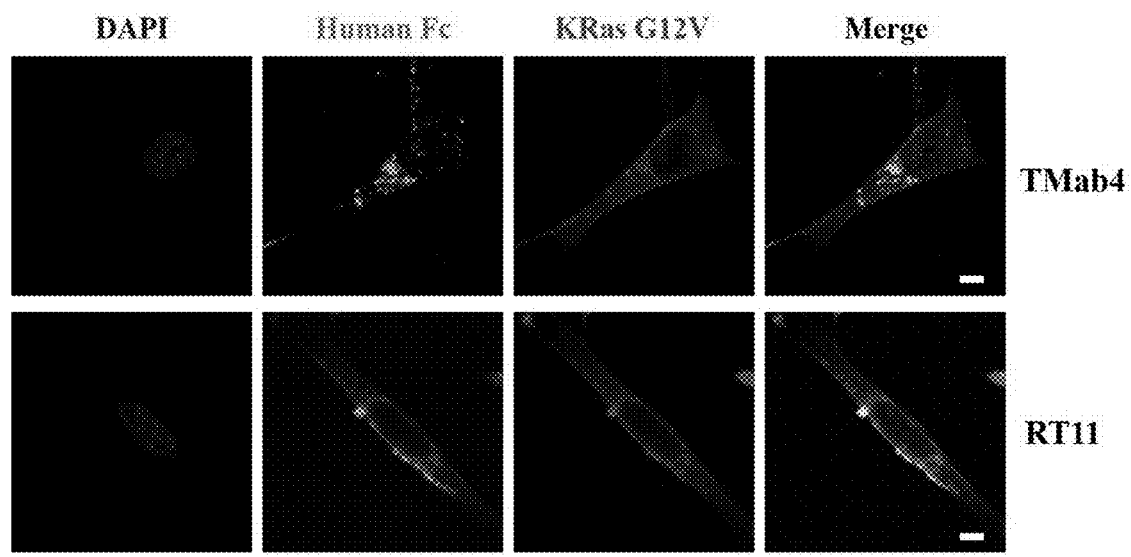
FIG. 33 shows the results of confocal microscopic observation performed to examine whether RT11 is superimposed with activated KRas G12V mutants in cells.

As shown in FIG. 33, green fluorescent RT11 was superimposed with the cellular inner membrane in which red-fluorescent activated Ras was located, whereas TMab was not superimposed.

Figure 34:
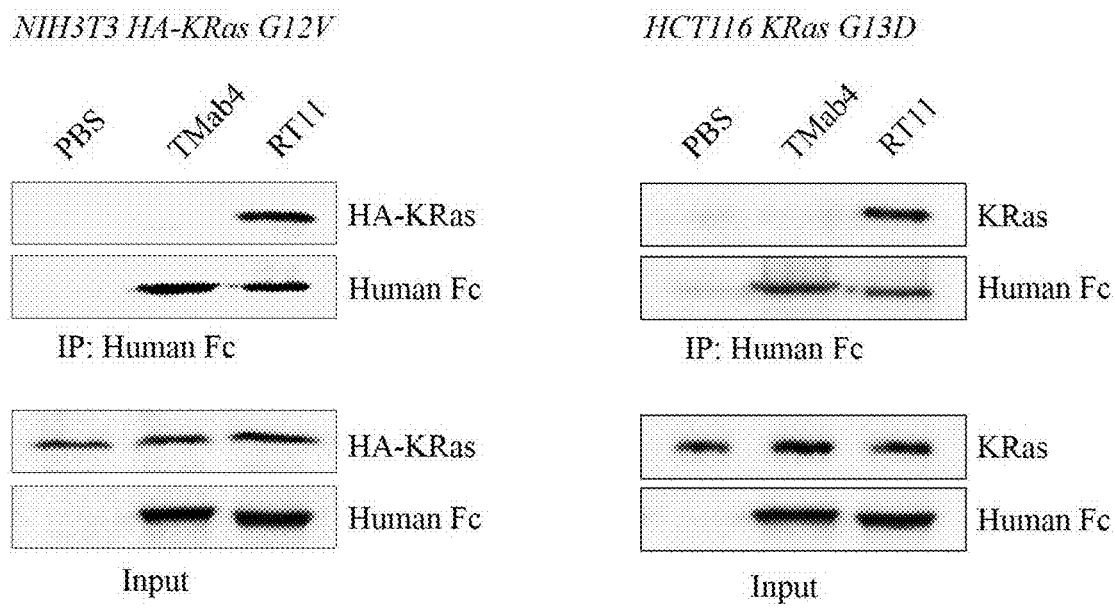
FIG. 34 shows the results of an immunoprecipitation assay performed to examine whether RT11 binds to activated Ras in cells.

FIG. 34 shows the results of an immunoprecipitation assay performed to confirm whether RT11 binds to activated Ras in cells.

Specifically, 10 ml of a dilution of each of a KRas G12V mutant-expressing NIH3T3 cell line and HCT116 cell line was added to a 100 mm³ plate at a density of $2\times10^6$ cells per well, and cultured for 12 hours under the conditions of 37° C. and 5% $CO_2$. Next, the cells were treated with 2 μM of each of TMab4 and RT11 and cultured at 37° C. for 12 hours. Thereafter, the cells were lysed using a cell lysis buffer (25 mM Tris-Cl pH 7.4, 150 mM NaCl, 1% NP-40, 10 mM $MgCl_2$, 10% glycerol, protease inhibitors), and the cell debris was removed by precipitation. Protein A/G agarose was added to the cell lysate and incubated for 2 hours, and then the antibody was precipitated. Next, Western blot analysis was performed using anti-KRas antibody (Santa Cruz) and human Fc antibody (Sigma).

As shown in FIG. 34, KRas was observed only in RT11, but was not observed in TMab4 and PBS.

Such experimental results indicate that RT11 binds specifically to intracellular activated Ras.

Figure 35A:
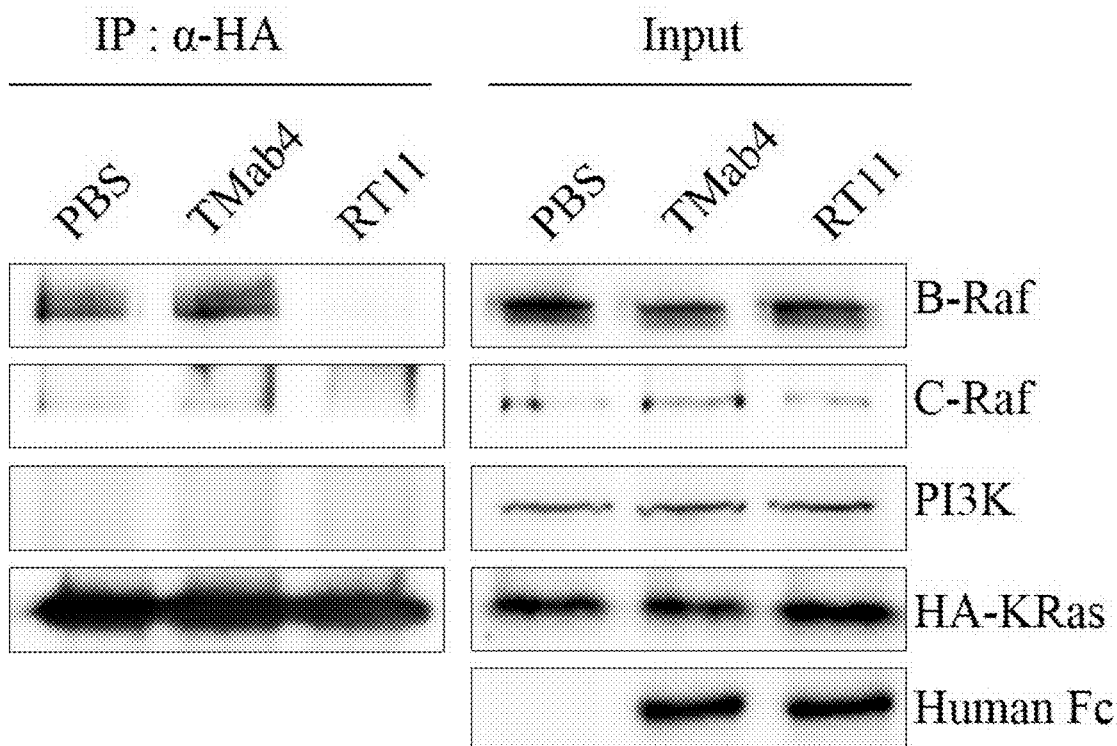
FIGS. 35A and 35B show the results of an immunoprecipitation assay performed to examine whether or not RT11 inhibits the binding between Ras•GTP and effector proteins.
Figure 35B:
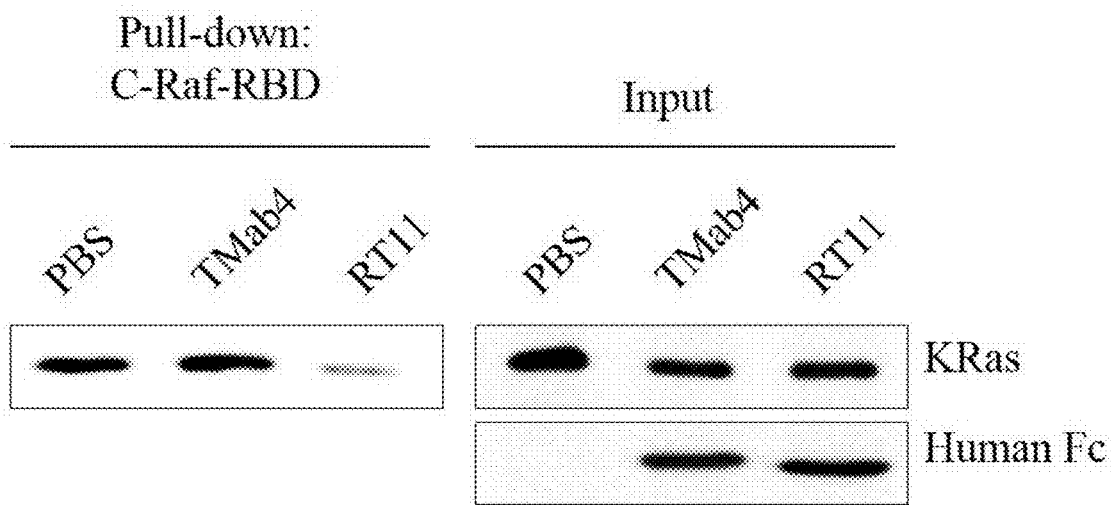

(2) Examination of the Ability of Anti-Ras•GTP iMab RT11 to Inhibit Binding Between Ras•GTP and Effector Molecule FIGS. 35A and 35B show the results of an immunoprecipitation assay performed to examine whether or not RT11 inhibits the binding between Ras•GTP and effector proteins.

Specifically, 10 ml of a dilution of each of a KRas G12V mutant-expressing NIH3T3 cell line and HCT116 cell line was added to a 100 mm³ plate at a density of $2\times10^6$ cells per well, and cultured for 12 hours under the conditions of 37° C. and 5% $CO_2$. Next, the cells were treated with 2 μM of each of TMab4 and RT11 and cultured at 37° C. for 12 hours. Thereafter, the cells were lysed using a cell lysis buffer (25 mM Tris-Cl pH 7.4, 150 mM NaCl, 1% NP-40, 10 mM $MgCl_2$, 10% glycerol, protease inhibitors), and the cell debris was removed by precipitation. The KRas G12V mutant cell lysate was incubated with anti-HA antibody (Covance) for 2 hours, and then treated with Protein A/G agarose to precipitate the anti-HA antibody. Raf-1 RBD agarose (Millipore) was added to the HCT116 cell lysate and incubated for 2 hours, and then precipitated. Next, Western blot analysis was performed using anti B-Rat C-Raf, PI3K and KRas antibodies (Santa Cruz) and human Fc antibody (Sigma).

As shown in FIG. 35A, anti-Ras•GTP iMab RT11 inhibited the binding between Ras. GTP and effector proteins (B-Raf and C-Raf), whereas TMab4 did not inhibit the binding. Similarly, FIG. 35B shows that only the anti-Ras•GTP iMab RT11 inhibited the binding between the effector protein C-Raf and Ras•GTP, whereas TMab4 did not inhibit the binding.

Such experimental results indicate that RT11 binds specifically to intracellular Ras•GTP to thereby inhibit the binding between Ras•GTP and the effector proteins (B-Raf, and C-Raf).

Example 27: Construction of RGD10 Peptide-Fused Anti-Ras•GTP iMab RT11 and Analysis of the Ability to Bind to Ras•GTP As described in Example 15, anti-Ras•GTP iMab RT11 penetrates by binding to HSPG on the cell surface. Thus, it is required to impart tissue specificity to anti-Ras•GTP iMab RT11 for in vivo experiments. For this, an RGD10 peptide (DGARYCRGDCFDG; SEQ ID NO: 42) having specificity for integrin αvβ3 which is overexpressed in angiogenetic cells and various tumors was fused to the N-terminus of the light chain via a linker consisting of a total of 10 residues (GGGGSGGGGS) by a genetic engineering method. The RGD10 peptide will have an affinity for integrin, which is similar to that of a previous RGD4C peptide fused to RT4, and it has one disulfide bond in the peptide, and thus is expected to be more easily fused to the N-terminus of the antibody. Thus, the RGD10 peptide was fused to anti-Ras•GTP iMab RT11 by a genetic engineering method.

Figure 36:
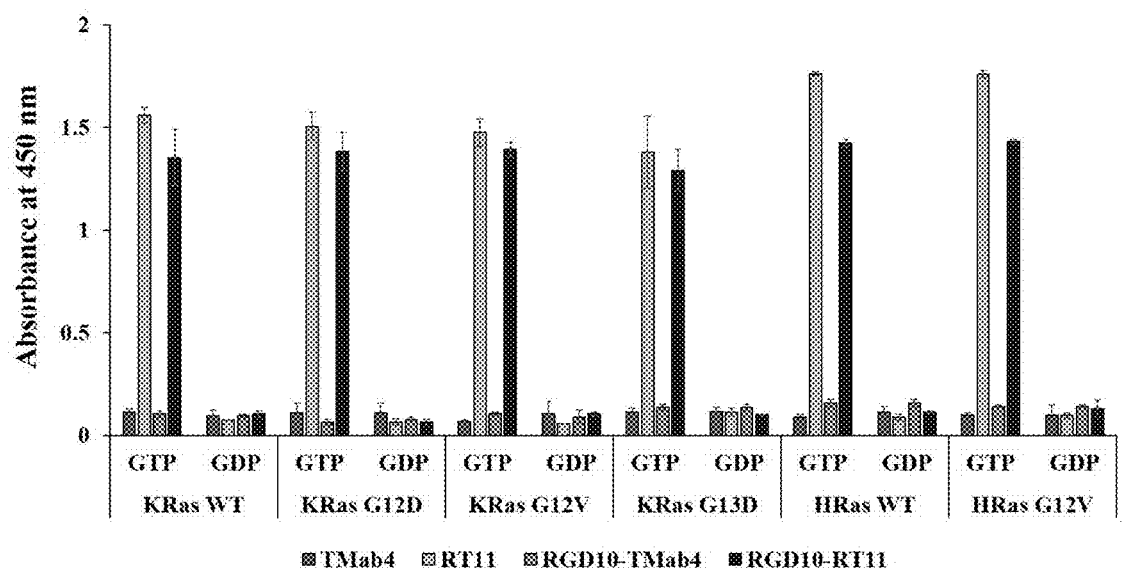
FIG. 36 shows the ELISA results obtained by measuring the affinities of the constructed RGD10 peptide-fused RT11 (RGD10-RT11) for a variety of GTP-bound and GDP-bound Ras mutants.

FIG. 36 shows the ELISA results obtained by measuring the affinities of the constructed RGD10 peptide-fused RT11 for a variety of GTP-bound and GDP-bound Ras mutants.

Specifically, according to the same method as described in Example 11, each of GTP-bound KRas G12D and GDP-bound Ras, which are target molecules, was incubated in a 96-well EIA/RIA plate (COSTAR Corning) at 37° C. for 1 hour, and then the plate was washed three times with 0.1%

TBST (0.1% Tween20, pH 7.4, 137 mM NaCl, 12 mM Tris, 2.7 mM KCl, 5 mM $MgCl_2$) (SIGMA) for 10 minutes. Next, each well of the plate was incubated with 4% TBSB (4% BSA, pH7.4, 137 mM NaCl, 12 mM Tris, 2.7 mM KCl, 10 mM $MgCl_2$) (SIGMA) for 1 hour, and then washed three times with 0.1% TBST for 10 minutes. Thereafter, each well was incubated with each of the anti-Ras•GTP iMab clones diluted in 4% TBSB at a concentration of 10 nM, after which each well was washed three times with 0.1% TBST for 10 minutes. As a marker antibody, goat alkaline phosphatase-conjugated anti-human mAb (SIGMA) was used. Each well was incubated with Ultra TMB-ELISA substrate solution (Thermo Scientific), and then the absorbance at 450 nm was measured.

As shown in FIG. 36, RGD10 peptide-fused RT11 (RGD10-RT11) showed the same affinity for GTP-bound Ras mutants.

Example 28: Evaluation of Cytotoxicity of RGD10-Fused Anti-Ras•GTP iMab RT11

Figure 37:
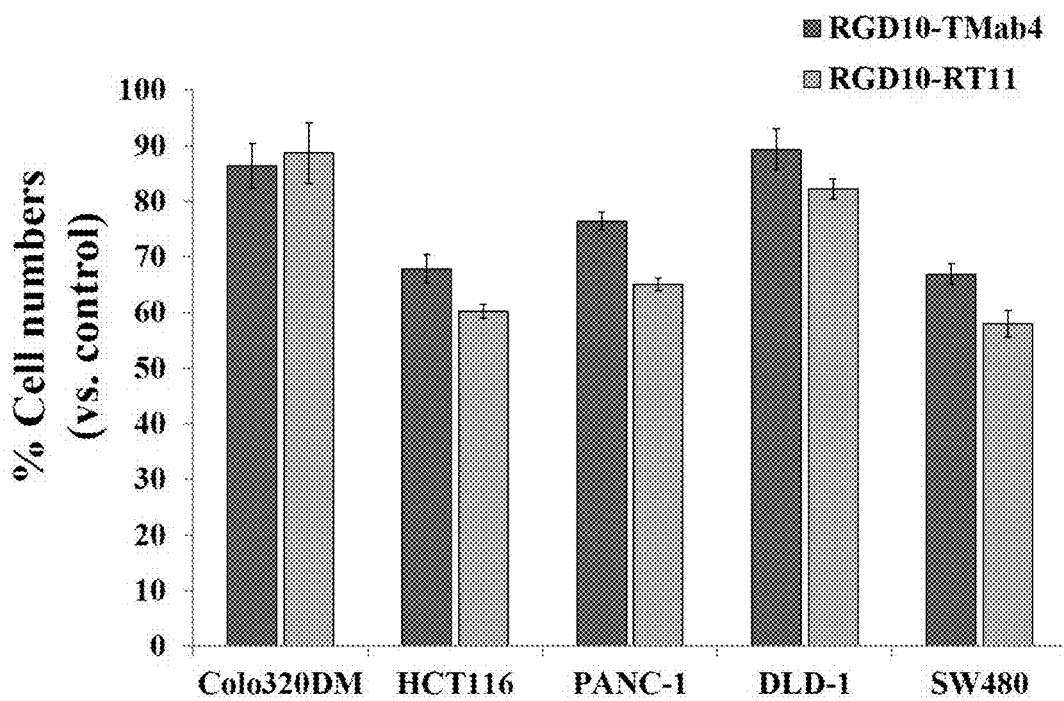
FIGS. 37 and 38 show the results obtained by treating Colo320DM, HCT116, PANC-1, SW480 and DLD-1 cell lines with RGD10-TMab4 and RGD10-RT11 and evaluating in vitro the inhibition of growth of the cells.
Figure 38:
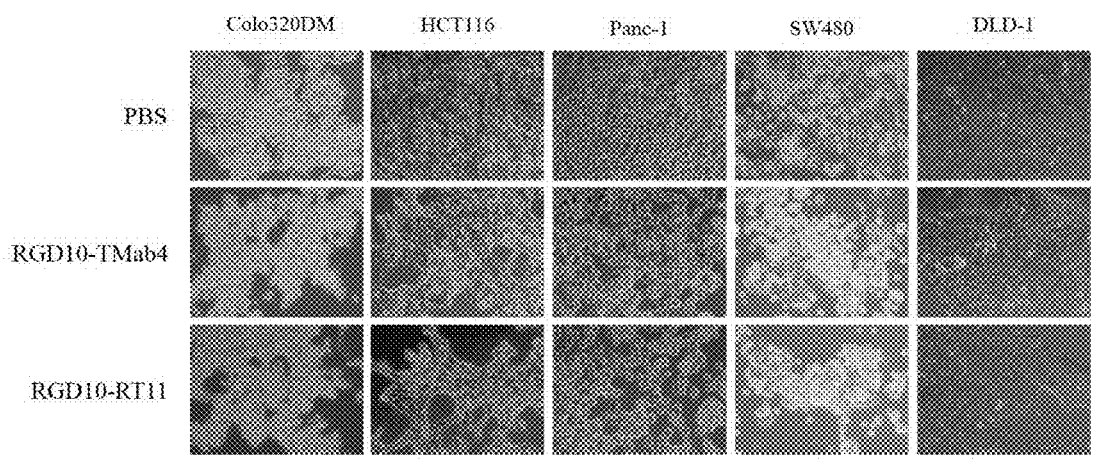

FIGS. 37 and 38 show the results obtained by treating Colo320DM, HCT116, PANC-1, SW480 and DLD-1 cell lines with RGD10-TMab4 and RGD10-RT11 and evaluating in vitro the inhibition of growth of the cells.

In order to evaluate in vitro whether RGD10-TMab4 and RGD-RT11 themselves have cytotoxicity, the inhibition of growth of cells was evaluated using human colorectal cancer Colo320DM cells as a Ras wild-type cell line and using human colorectal cancer cell lines (HCT116 (KRas G13D), SW480 (KRas G12V), DLD-1 (KRas G13D)) and a human pancreatic cancer cell line (PANC-1 (KRas G12D)).

Specifically, cells were added to each well of a 24-well plate at a density of $5 \times 10^3$ cells per well with 0.5 ml of 10% FBS-containing medium, and cultured for 12 hours under the conditions of 37° C. and 5% $CO_2$. Next, the cells were treated twice with 1 μM of each of RGD10-TMab4 and RGD10-RT11 for 72 hours each time and observed for a total of 144 hours, and then the number of viable cells was counted to determine the degree of growth of the cells.

As shown in FIG. 37, the comparison between RGD10-TMab4 and RGD10-RT11 indicated that the KRas mutant cell lines (HCT116, SW480, DLD-1, and PANC-1) showed a difference in cell growth of about 8-12%, whereas the Ras wild-type cell line showed no difference in cell growth. Thus, the comparison between RGD10-TMab4 and RGD10-RT11 indicated that RT11 can inhibit the growth of Ras-specific cells even when the RGD10 peptide is fused thereto.

Example 29: Examination of Whether RGD10-Fused Anti-Ras•GTP iMab RT11 Binds Specifically to Integrin αvβ3

Figure 39:
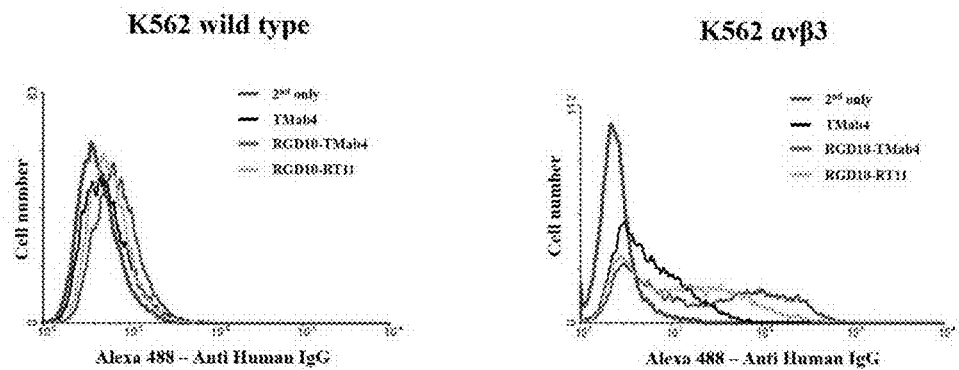
FIG. 39 shows the results of analysis performed to examine whether or not RGD10-TMab4 and RGD10-RT11 bind specifically to integrin αvβ3 on the cell surface.

FIG. 39 shows the results of analysis performed to examine whether or not RGD10-TMab4 and RGD10-RT11 bind specifically to integrin αvβ3 on the cell surface.

Specifically, each of a K562 cell line and a K562 integrin αvβ3-overexpressing cell line was added to 1.5 ml at a density of $2 \times 10^5$ cells, then washed twice with washing buffer (pH 7.4 PBS, 2% FBS). 100 nM of each of TMab4, RGD10-TMab4 and RGD10-RT11 100 nM was mixed with 300 IU/ml of heparin (Sigma), and the cells were incubated with the mixture at 4° C. for 1 hour. The cells were washed twice with washing buffer, and then stained with an Alexa488 (green fluorescence)-labeled antibody (Invitrogen) that specifically recognizes human IgG, at 4° for 1 hour. Next, the cells were washed twice with washing buffer, and analyzed by FACS.

As shown in FIG. 39, unlike TMab4, RGD10-TMAb4 and RGD10-RT11 did bind specifically to the K562 integrin αvβ3 cells. This suggests that the RGD10 peptide binds specifically to integrin αvβ3.

Example 30: Examination of Whether Anti-Ras•GTP iMab RT11 Binds Specifically to Intracellular Ras•GTP FIG. 40 shows the results of confocal microscopic observation performed to examine whether or not RGD10-RT11 is superimposed with an activated KRas G12V mutant in cells.

Specifically, a 24-well plate was coated with fibronectin (Sigma), and then 0.5 ml of a dilution of mCherry (red fluorescence) KRas G12V-expressing NIH3T3 cells were added to each well at a density of $2 \times 10^2$ cells per well and cultured for 12 hours under the conditions of 37° C. and 5% $CO_2$. Then, the cells were treated and incubated with 1 μM of each of RGD10-TMab4 and RGD10-RT11 for 12 hours under the conditions of 37° C. and 12 hours. Next, the cells were stained under the same conditions as described in Example 14, and were observed with a confocal microscope.

Figure 40:
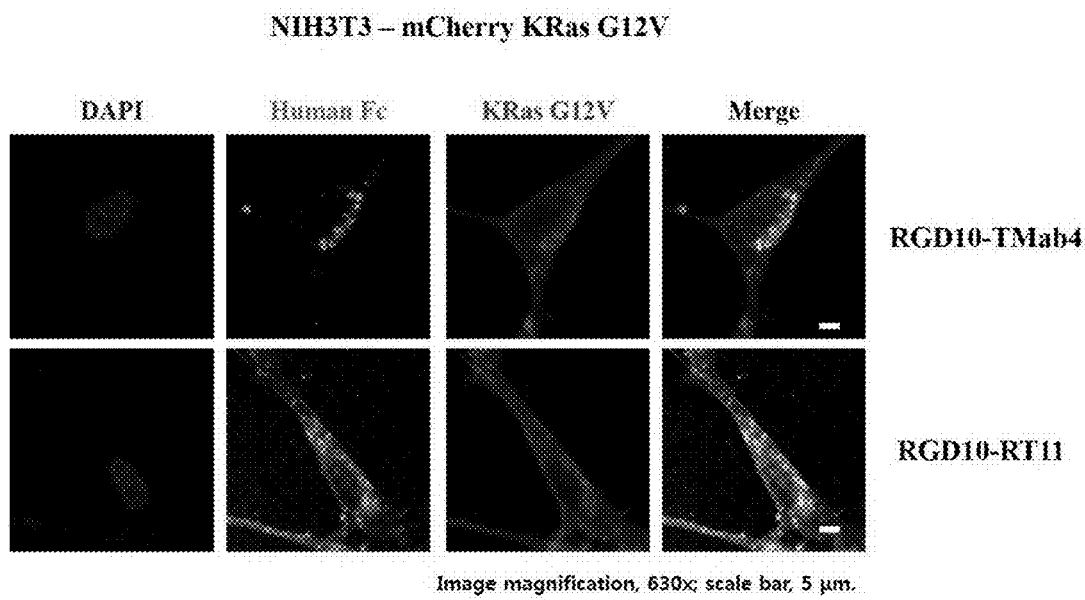
FIG. 40 shows the results of confocal microscopic observation performed to examine whether or not RGD10-RT11 is superimposed with an activated KRas G12V mutant in cells.

As shown in FIG. 40, green fluorescent RGD10-RT11 was superimposed with the cellular inner membrane in which red-fluorescent activated Ras was located, whereas RGD10-TMab was not superimposed.

Such experimental results indicate that RGD10-RT11 binds specifically to intracellular activated Ras.

The invention claimed is:

1. An anti-RAS antibody,
wherein the antibody comprises a heavy chain variable region (VH) that binds specifically to RAS-GTP comprising:
a VH CDR1, VH CDR2 and VH CDR3, respectively comprising the amino acid sequences selected from the group consisting of:
VHCDR1 SEQ ID NO: 11, VHCDR2 SEQ ID NO: 12, and VHCDR3 SEQ ID NO: 13;
VHCDR1 SEQ ID NO: 14, VHCDR2 SEQ ID NO: 15, and VHCDR3 SEQ ID NO: 16;
VHCDR1 SEQ ID NO: 17, VHCDR2 SEQ ID NO: 18, and VHCDR3 SEQ ID NO: 19;
VHCDR1 SEQ ID NO: 20, VHCDR2 SEQ ID NO: 21, and VHCDR3 SEQ ID NO: 22;
VHCDR1 SEQ ID NO: 23, VHCDR2 SEQ ID NO: 24, and VHCDR3 SEQ ID NO: 25; and
VHCDR1 SEQ ID NO: 26, VHCDR2 SEQ ID NO: 27, and VHCDR3 SEQ ID NO: 28; and
a light-chain variable region (VL) that penetrates the cell membrane comprising:
a VL CDR1, VL CDR2, and VL CDR3, respectively comprising the amino acid sequences selected from the group consisting of:
VLCDR1 SEQ ID NO: 32, VLCDR2 SEQ ID NO: 33, VHCDR3 SEQ ID NO: 34; and
VLCDR1 SEQ ID NO: 32, VLCDR2 SEQ ID NO: 33, VHCDR3 SEQ ID NO: 40;
wherein 2nd and 4th amino acids starting from the N-terminus of the light-chain variable region are respectively substituted with leucine (L) and methionine (M), (wherein the positions of the amino acids are numbered according to the Kabat numbering system).

2. The antibody of claim 1, wherein the antibody binds specifically to RAS-GTP in the cytosol of a cell.

3. The antibody of claim 1, wherein the 9th, 10th, 13th, 15th, 17th, 19th, 21st, 22nd, 42nd, 45th, 58th, 60th, 79th and 85th amino acids starting from the N-terminus of the light-chain variable region (VL) are serine (S), serine (S), alanine (A), valine (V), aspartic acid (D), valine (V), isoleucine (I), threonine (T), lysine (K), lysine (K), valine (V), serine (S), glutamine (Q) and threonine (T), respectively (wherein the positions of the amino acids are numbered according to the Kabat numbering system).

4. The antibody of claim 3, wherein the 89th and 91st amino acids starting from the N-terminus of the light-chain variable region (VL) are glutamine (Q) and tyrosine (Y), respectively (wherein the positions of the amino acids are numbered according to the Kabat numbering system).

5. The antibody of claim 1, wherein the heavy chain variable region (VH) comprises an amino acid sequence selected from the group consisting of SEQ ID NOs: 2 to 7.

6. The antibody of claim 5, wherein the antibody binds specifically to the RAS-GTP in the cytosol of a cell.

7. The antibody of claim 1, wherein the light-chain variable region (VL) comprises an amino acid sequence selected from the group consisting of SEQ ID NOs: 29, 30 and 31.

8. The antibody of claim 1, wherein the antibody is fused to a biologically active molecule selected from the group consisting of peptides, proteins, small-molecule drugs, nanoparticles and liposomes.

9. The antibody of claim 8, wherein the biologically active molecule is a peptide, wherein the peptide is RGD4C comprising an amino acid sequence as set forth in SEQ ID No: 41, or RGD4C comprising an amino acid sequence as set forth in SEQ ID No: 42.

10. A polynucleotide that encodes the antibody of claim 1.

11. The antibody of claim 1, wherein the antibody comprises a full-length heavy chain variable region (VH).

12. The antibody of claim 11, wherein the antibody is an intact immunoglobulin-type antibody.

13. The antibody of claim 11, wherein the antibody binds specifically to the RAS-GTP in the cytosol of a cell.

14. The antibody of claim 12, wherein the antibody binds specifically to the RAS-GTP in the cytosol of a cell.

* * * * *